United States Patent
Eickmeier et al.

(10) Patent No.: US 8,648,085 B2
(45) Date of Patent: Feb. 11, 2014

(54) 1, 5-DIHYDRO-PYRAZOLO (3, 4-D) PYRIMIDIN-4-ONE DERIVATIVES AND THEIR USE AS PDE9A MUDULATORS FOR THE TREATMENT OF CNS DISORDERS

(75) Inventors: Christian Eickmeier, Mittelbiberach (DE); Cornelia Dorner-Ciossek, Warthausen (DE); Dennis Fiegen, Biberach (DE); Thomas Fox, Biberach (DE); Klaus Fuchs, Mittelbiberach (DE); Riccardo Giovannini, Verona (IT); Niklas Heine, Biberach (DE); Martin Hendrix, Orinda, CA (US); Holger Rosenbrock, Mittelbiberach (DE); Gerhard Schaenzle, Biberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 529 days.

(21) Appl. No.: 12/744,750

(22) PCT Filed: Nov. 27, 2008

(86) PCT No.: PCT/EP2008/066350
§ 371 (c)(1),
(2), (4) Date: Oct. 7, 2010

(87) PCT Pub. No.: WO2009/068617
PCT Pub. Date: Jun. 4, 2009

(65) Prior Publication Data
US 2011/0015193 A1    Jan. 20, 2011

(30) Foreign Application Priority Data

Nov. 30, 2007  (EP) .................................. 07425764
Sep. 3, 2008   (EP) .................................. 08163548
Nov. 17, 2008  (EP) .................................. 08169282

(51) Int. Cl.
| C07D 487/04 | (2006.01) |
| A61K 31/519 | (2006.01) |
| A61P 25/28 | (2006.01) |
| A61P 3/04 | (2006.01) |
| A61P 3/10 | (2006.01) |
| A61P 25/16 | (2006.01) |

(52) U.S. Cl.
USPC ...... 514/262.1; 544/262; 544/118; 514/234.2

(58) Field of Classification Search
USPC ....................... 544/262; 514/262.1
See application file for complete search history.

(56) References Cited

U.S. PATENT DOCUMENTS

| 3,165,520 A | 1/1965 | Schmidt et al. |
| 3,169,965 A | 2/1965 | Schmidt et al. |

(Continued)

FOREIGN PATENT DOCUMENTS

| CA | 2090227 A1 | 3/1992 |
| CA | 1311201 C | 12/1992 |

(Continued)

OTHER PUBLICATIONS

Caligiuri et al. (Chemistry & Biology, 2005, vol. 12, pp. 1103-1115).*

(Continued)

*Primary Examiner* — Susanna Moore
(74) *Attorney, Agent, or Firm* — Michael P. Morris; Edward S. Lazer

(57) ABSTRACT

The invention relates to novel substituted pyrazolopyrimidines. Chemically, the compounds are characterized by general Formula (I): with $R^1$ being phenyl or pyridyl, any of which is substituted with 1 to 4, preferably 1 to 3 substituents X; X independently of each other being selected from $C_2-C_6$-alky$_1$ or Ci-$C_6$-alkoxy, where $C_2-C_6$-alkyl and $C_1-C_6$-alkoxy are at least dihalogenated up to perhalogenated. preferably with 2 to 6 halogen substituents, and the halogen atoms being selected from the group of fluoro, chloro and bromo, preferably fluoro; $R^2$ being phenyl or heteroaryl, where phenyl is substituted by 1 to 3 radicals and heteroaryl is optionally substituted by 1 to 3 radicals in each case independently of one another selected from the group of $C_1-C_6$-alkyl, $C_1-C_6$-alkoxy, hydroxycarbonyl, cyano, trifluoromethyl, amino, nitro, hydroxy, $C_1-C_6$-alkylamino, halogen, $C_6-C_{10}$-arylcarbonylamino, $C_1-C_6$-alkylcarbonylamino, $C_1-C_6$-alkylaminocarbonyl. $C_1-C_6$-alkoxycarbonyl, $C_6-C_{10}$-arylaminocarbonyl, heteroarylaminocarbonyl. heteroarylcarbonylamino, $C_1-C_6$-alkylsulphonyl-amino, $C_1-C_6$-alkylsulphonyl and $C_1-C_6$-alkylthio; The new compounds shall be used for the manufacture of medicaments, in particular medicaments for improving, perception, concentration, learning and/or memory in patients in need thereof.

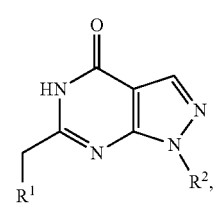

(I)

9 Claims, No Drawings

(56) References Cited

U.S. PATENT DOCUMENTS

| | | |
|---|---|---|
| 3,211,731 A | 10/1965 | Schmidt et al. |
| 3,244,328 A | 4/1966 | Brown |
| 3,732,225 A | 5/1973 | Breuer et al. |
| 3,847,908 A | 11/1974 | Breuer et al. |
| 3,884,906 A | 5/1975 | Van Der Meer et al. |
| 4,602,023 A | 7/1986 | Kiely et al. |
| 5,002,949 A | 3/1991 | Peseckis et al. |
| 5,041,449 A | 8/1991 | Belleau et al. |
| 5,047,407 A | 9/1991 | Belleau et al. |
| 5,053,499 A | 10/1991 | Kojima et al. |
| 5,113,855 A | 5/1992 | Newhouse |
| 5,201,308 A | 4/1993 | Newhouse |
| 5,239,992 A | 8/1993 | Bougamont et al. |
| 5,256,668 A | 10/1993 | Hsu et al. |
| 5,270,315 A | 12/1993 | Belleau et al. |
| 5,294,612 A | 3/1994 | Bacon et al. |
| 5,341,801 A | 8/1994 | Zechner |
| 5,466,806 A | 11/1995 | Belleau et al. |
| 5,503,144 A | 4/1996 | Bacon |
| 5,541,187 A | 7/1996 | Bacon et al. |
| 5,563,049 A | 10/1996 | Kojima et al. |
| 5,568,884 A | 10/1996 | Bruna |
| 5,634,900 A | 6/1997 | Makino et al. |
| 5,656,629 A | 8/1997 | Bacon et al. |
| 5,684,164 A | 11/1997 | Belleau et al. |
| 5,750,673 A | 5/1998 | Martin |
| 5,948,812 A | 9/1999 | Kraft |
| 5,969,116 A | 10/1999 | Martin |
| 5,969,499 A | 10/1999 | Shaffer |
| 5,977,118 A | 11/1999 | Bacon et al. |
| 5,977,332 A | 11/1999 | Martin |
| 6,100,037 A | 8/2000 | Phillips et al. |
| 6,174,884 B1 | 1/2001 | Haning et al. |
| 6,175,008 B1 | 1/2001 | Belleau et al. |
| 6,211,158 B1 | 4/2001 | Seela et al. |
| 6,225,315 B1 | 5/2001 | Ellis |
| 6,350,753 B1 | 2/2002 | Belleau et al. |
| 6,458,796 B1 | 10/2002 | Haning et al. |
| 6,479,463 B1 | 11/2002 | Wang et al. |
| 6,831,174 B2 | 12/2004 | Belleau et al. |
| 6,903,224 B2 | 6/2005 | Belleau et al. |
| 7,022,709 B2 | 4/2006 | Boss et al. |
| 7,067,507 B2 | 6/2006 | Pulley et al. |
| 7,122,693 B2 | 10/2006 | Belleau et al. |
| 7,375,213 B2 | 5/2008 | Deshpande et al. |
| 7,488,733 B2 | 2/2009 | Hendrix et al. |
| 7,488,766 B2 | 2/2009 | Peters et al. |
| 7,541,341 B2 | 6/2009 | Fushimi et al. |
| 7,579,449 B2 | 8/2009 | Eckhardt et al. |
| 7,615,558 B2 | 11/2009 | Hendrix et al. |
| 7,662,790 B2 | 2/2010 | Himmelsbach et al. |
| 7,683,160 B2 | 3/2010 | Eckhardt et al. |
| 7,687,469 B2 | 3/2010 | Eckhardt et al. |
| 7,708,011 B2 | 5/2010 | Hochrainer et al. |
| 7,713,938 B2 | 5/2010 | Himmelsbach et al. |
| 7,723,309 B2 | 5/2010 | Himmelsbach et al. |
| 7,737,156 B2 | 6/2010 | Boβ et al. |
| 7,745,414 B2 | 6/2010 | Eckhardt et al. |
| 7,772,191 B2 | 8/2010 | Eckhardt et al. |
| 7,772,378 B2 | 8/2010 | Himmelsbach et al. |
| 7,776,830 B2 | 8/2010 | Eckhardt et al. |
| 7,847,074 B2 | 12/2010 | Eckhardt et al. |
| 7,851,602 B2 | 12/2010 | Himmelsbach et al. |
| 7,858,587 B2 | 12/2010 | Eckhardt et al. |
| 7,870,856 B2 | 1/2011 | Boeck |
| 7,879,806 B2 | 2/2011 | Himmelsbach et al. |
| 7,879,807 B2 | 2/2011 | Himmelsbach et al. |
| 7,984,713 B2 | 7/2011 | Hochrainer et al. |
| 8,039,441 B2 | 10/2011 | Himmelsbach et al. |
| 8,039,477 B2 | 10/2011 | Hendrix et al. |
| 8,044,060 B2 | 10/2011 | Hendrix et al. |
| 8,088,769 B2 | 1/2012 | Hendrix et al. |
| 2001/0041797 A1 | 11/2001 | Belleau et al. |
| 2001/0044441 A1 | 11/2001 | Campbell et al. |
| 2002/0016348 A1 | 2/2002 | Simitchieva et al. |
| 2002/0074774 A1 | 6/2002 | Hsu et al. |
| 2002/0086160 A1 | 7/2002 | Qiu et al. |
| 2002/0100222 A1 | 8/2002 | Koenig et al. |
| 2002/0132754 A1 | 9/2002 | Boss et al. |
| 2002/0137903 A1 | 9/2002 | Ellsworth et al. |
| 2003/0064935 A1 | 4/2003 | Gougoutas |
| 2003/0087918 A1 | 5/2003 | Belleau et al. |
| 2003/0114390 A1 | 6/2003 | Washburn et al. |
| 2003/0195205 A1 | 10/2003 | DeNinno et al. |
| 2004/0185459 A1 | 9/2004 | Otsuka et al. |
| 2004/0187868 A1 | 9/2004 | Hochrainer et al. |
| 2004/0220186 A1 | 11/2004 | Bell et al. |
| 2004/0254201 A1 | 12/2004 | Belleau et al. |
| 2004/0266736 A1 | 12/2004 | Wunder et al. |
| 2005/0187168 A1 | 8/2005 | Eickelmann et al. |
| 2005/0209251 A1 | 9/2005 | Linker et al. |
| 2005/0233982 A1 | 10/2005 | Himmelsbach et al. |
| 2005/0263151 A1 | 12/2005 | Hochrainer et al. |
| 2006/0009400 A1 | 1/2006 | Eckhardt et al. |
| 2006/0025349 A1 | 2/2006 | Eckhardt et al. |
| 2006/0074031 A1 | 4/2006 | Eckhardt et al. |
| 2006/0100222 A1 | 5/2006 | Boss et al. |
| 2006/0106035 A1 | 5/2006 | Hendrix et al. |
| 2006/0111372 A1 | 5/2006 | Hendrix et al. |
| 2007/0037977 A1 | 2/2007 | Belleau et al. |
| 2007/0105876 A1 | 5/2007 | Hendrix et al. |
| 2007/0105881 A1 | 5/2007 | Hendrix et al. |
| 2007/0161662 A1 | 7/2007 | Hendrix et al. |
| 2007/0240713 A1 | 10/2007 | Boeck |
| 2007/0281940 A1 | 12/2007 | Dugi et al. |
| 2008/0255118 A1 | 10/2008 | Hendrix et al. |
| 2009/0023913 A1 | 1/2009 | Eckhardt et al. |
| 2009/0111838 A1 | 4/2009 | Hendrix et al. |
| 2009/0121919 A1 | 5/2009 | Kihara |
| 2009/0194105 A1 | 8/2009 | Besseler et al. |
| 2009/0235929 A1 | 9/2009 | Egen et al. |
| 2009/0318547 A1 | 12/2009 | Eckhardt et al. |
| 2009/0326215 A1 | 12/2009 | Eckhardt et al. |
| 2010/0024815 A1 | 2/2010 | Kladders |
| 2010/0035900 A1 | 2/2010 | Hendrix et al. |
| 2010/0069310 A1 | 3/2010 | Himmelsbach et al. |
| 2010/0081625 A1 | 4/2010 | Wienrich et al. |
| 2010/0093654 A1 | 4/2010 | Himmelsbach et al. |
| 2010/0099641 A1 | 4/2010 | Himmelsbach et al. |
| 2010/0179191 A1 | 7/2010 | Himmelsbach et al. |
| 2010/0209506 A1 | 8/2010 | Eisenreich |
| 2010/0210839 A1 | 8/2010 | Boss et al. |
| 2010/0240879 A1 | 9/2010 | Eckhardt et al. |
| 2010/0249392 A1 | 9/2010 | Eckhardt et al. |
| 2010/0298243 A1 | 11/2010 | Manuchehri et al. |
| 2010/0317847 A1 | 12/2010 | Eckhardt et al. |
| 2011/0014284 A1 | 1/2011 | Eisenreich et al. |
| 2011/0015193 A1 | 1/2011 | Eickmeier et al. |
| 2011/0046076 A1 | 2/2011 | Eickelmann et al. |
| 2011/0046087 A1 | 2/2011 | Eickelmann et al. |
| 2011/0065730 A1 | 3/2011 | Hendrix et al. |
| 2011/0065731 A1 | 3/2011 | Dugi et al. |
| 2011/0082137 A1 | 4/2011 | Giovannini et al. |
| 2011/0098240 A1 | 4/2011 | Dugi et al. |
| 2011/0178033 A1 | 7/2011 | Eckhardt et al. |
| 2011/0184000 A1 | 7/2011 | Giovannini et al. |
| 2011/0203586 A1 | 8/2011 | Egen et al. |
| 2011/0207735 A1 | 8/2011 | Hendrix et al. |
| 2011/0212960 A1 | 9/2011 | Heine et al. |
| 2011/0236477 A1 | 9/2011 | Schneider et al. |
| 2011/0237526 A1 | 9/2011 | Weber et al. |
| 2011/0237789 A1 | 9/2011 | Weber et al. |
| 2011/0294834 A1 | 12/2011 | Hendrix et al. |
| 2012/0010224 A1 | 1/2012 | Hendrix et al. |
| 2012/0115863 A1 | 5/2012 | Fuchs et al. |
| 2012/0165349 A1 | 6/2012 | Hendrix et al. |
| 2012/0202829 A1 | 8/2012 | Heine et al. |

FOREIGN PATENT DOCUMENTS

| | | |
|---|---|---|
| CA | 2283211 A1 | 9/1998 |
| CA | 2238211 A1 | 12/1998 |
| CA | 2357146 A1 | 7/2000 |
| CA | 2437240 A1 | 8/2002 |

(56) References Cited

FOREIGN PATENT DOCUMENTS

| | | |
|---|---|---|
| CA | 2438890 A1 | 9/2002 |
| CA | 2417631 A1 | 1/2003 |
| CA | 2466824 A1 | 5/2003 |
| CA | 2484997 A1 | 11/2003 |
| CA | 2 496 194 A1 | 3/2004 |
| CA | 2496292 A1 | 4/2004 |
| CA | 2496306 A1 | 4/2004 |
| CA | 2496308 A1 | 4/2004 |
| CA | 2 524 898 A1 | 11/2004 |
| CA | 2524900 A1 | 11/2004 |
| CA | 2539032 A1 | 3/2005 |
| CH | 396923 A | 8/1965 |
| CH | 396924 A | 8/1965 |
| CH | 396925 A | 8/1965 |
| CH | 396926 A | 8/1965 |
| CH | 396927 A | 8/1965 |
| CH | 398626 A | 3/1966 |
| DE | 1147234 B | 4/1963 |
| DE | 1149013 B | 5/1963 |
| DE | 1153023 B | 8/1963 |
| DE | 1156415 B | 10/1963 |
| DE | 2408906 A1 | 9/1974 |
| DE | 4004558 A1 | 9/1990 |
| DE | 4027391 A1 | 3/1992 |
| DE | 10156249 A1 | 5/2003 |
| DE | 10238722 A1 | 3/2004 |
| EP | 0130735 A1 | 1/1985 |
| EP | 0286028 A2 | 10/1988 |
| EP | 0496617 A1 | 7/1992 |
| EP | 0516510 A1 | 12/1992 |
| EP | 0546996 A2 | 6/1993 |
| EP | 0626387 A1 | 11/1994 |
| EP | 0679657 A2 | 11/1995 |
| EP | 0995751 A2 | 4/2000 |
| EP | 1460077 A1 | 9/2004 |
| GB | 937723 A | 9/1963 |
| GB | 937724 A | 9/1963 |
| GB | 937726 A | 9/1963 |
| GB | 973361 A | 10/1964 |
| JP | 2001513638 A | 9/2001 |
| JP | 2001514638 A | 9/2001 |
| JP | 2002523507 A | 7/2002 |
| JP | 2004536933 A | 12/2004 |
| JP | 2005531549 A | 10/2005 |
| JP | 2006501272 A | 1/2006 |
| JP | 2006503051 A | 1/2006 |
| WO | 9414802 A1 | 7/1994 |
| WO | 9417803 A1 | 8/1994 |
| WO | 9510506 A1 | 4/1995 |
| WO | 9628429 A1 | 9/1996 |
| WO | 9716456 A1 | 5/1997 |
| WO | 9746569 A2 | 12/1997 |
| WO | 9800434 A1 | 1/1998 |
| WO | 9810765 A1 | 3/1998 |
| WO | 9816184 A2 | 4/1998 |
| WO | 9840384 A1 | 9/1998 |
| WO | 9941253 A1 | 8/1999 |
| WO | 0018758 A1 | 4/2000 |
| WO | 0043394 A1 | 7/2000 |
| WO | 0160315 A2 | 8/2001 |
| WO | 0177075 A2 | 10/2001 |
| WO | 0206288 A1 | 1/2002 |
| WO | 0209713 A2 | 2/2002 |
| WO | 0216348 A1 | 2/2002 |
| WO | 02055082 A1 | 7/2002 |
| WO | 02057425 A2 | 7/2002 |
| WO | 02068423 A1 | 9/2002 |
| WO | 02074774 A1 | 9/2002 |
| WO | 02086160 A1 | 10/2002 |
| WO | 02098864 A1 | 12/2002 |
| WO | 03011923 A1 | 2/2003 |
| WO | 03011925 A1 | 2/2003 |
| WO | 03022859 A2 | 3/2003 |
| WO | 03031458 A1 | 4/2003 |
| WO | 03037432 A1 | 5/2003 |
| WO | 03037899 A1 | 5/2003 |
| WO | 03041725 A2 | 5/2003 |
| WO | 03072757 A2 | 9/2003 |
| WO | 03093269 A2 | 11/2003 |
| WO | 03099840 A1 | 12/2003 |
| WO | 2004002999 A2 | 1/2004 |
| WO | 2004/018474 A1 | 3/2004 |
| WO | 2004026286 A2 | 4/2004 |
| WO | 2004026876 A1 | 4/2004 |
| WO | 2004046331 A2 | 6/2004 |
| WO | 2004/099210 A1 | 11/2004 |
| WO | 2004096811 A1 | 11/2004 |
| WO | 2004099211 A1 | 11/2004 |
| WO | WO 2004099210 * | 11/2004 |
| WO | 2004108139 A2 | 12/2004 |
| WO | 2004113306 A1 | 12/2004 |
| WO | 2005021566 A2 | 3/2005 |
| WO | 2005051944 A1 | 6/2005 |
| WO | 2005068436 A1 | 7/2005 |
| WO | 2006076455 A2 | 7/2006 |
| WO | 2006084281 A1 | 8/2006 |
| WO | 2006091905 A1 | 8/2006 |
| WO | 2006125548 A1 | 11/2006 |
| WO | 2007025043 A2 | 3/2007 |
| WO | 2007046747 A1 | 4/2007 |
| WO | 2008005542 A2 | 1/2008 |
| WO | 2008049923 A1 | 5/2008 |
| WO | 2008055959 A1 | 5/2008 |
| WO | 2008100447 A2 | 8/2008 |
| WO | 2008104077 A1 | 9/2008 |
| WO | 2008139293 A1 | 11/2008 |
| WO | 2009068617 A1 | 6/2009 |
| WO | 2009121919 A1 | 10/2009 |
| WO | 2010026214 A1 | 3/2010 |
| WO | 2010092123 A1 | 8/2010 |
| WO | 2010092125 A1 | 8/2010 |
| WO | 2010112437 A1 | 10/2010 |
| WO | 2011018495 A1 | 2/2011 |

OTHER PUBLICATIONS

International Search Report for PCT/EP2008/066350 mailed Mar. 4, 2009.
Accessed on Dec. 18, 2008: wikipedia: "Amnesia", http://www.mentalhealth.org.uk/information/mental-health-a-z/dementia/, last accessed on Dec. 18, 2008.
Accessed on Jun. 30, 2008, Intelihealth: "Alzheimer's Disease," http://www.intelihealth.com/IH/ihtIH/WSIHW/8303/9117/195703.html?d=dmtHelathAZ.
Accessed on Sep. 22, 2009: Intelihealth: "Dementia," http://www.intelihealth.com/IH/ihtIH/WSIHW000/244798/00084.html.
Accessed on Sep. 22, 2009: Intelihealth: "Parkinson's Disease", http://www.intelihealth.com/IH/ihtIH?d=dmtHealthAZ&c=201957.
Andreeva, Svetlana G, et al; "Expression of cGMP-Specific Phosphodiesterase 9A . . . ", J. of Neuroscience, 2001, Vo. 21, No. 22, pp. 9068-9076.
Bagli, Jehan et al; Chemistry and Positive Inotropic Effect of Pelrinone and related Derivates. A Novel Class of 2-Methylpyrimidones as Inotropic Agents; Journal of Medicinal Chemistry (1988) vol. 31 pp. 814-823.
Barger, Steven, W; Role of Cyclic GMP in the Regulation of Neuronal Calcium and Survival by Secreted Forms of Beta-Amyloid Precursor; Journal of Neurochemistry (1995) vol. 64, No. 5, pp. 2087-2096.
Bernabeu, R., et al; Hippocampal cGMP and cAMP are Differentially Involved in Memory Processing of Inhibitors Avoidance Learning; Neuroreport (1996) vol. 7, No. 2 pp. 585-588.
Byrn, Stephen, R; Solid State Chemistry of Drugs (1999) vol. 2, No. 10, pp. 232-247.
Chem Abstracts Service, Database Accession No. ALB-H01677136, Database Chemcats, 2007, XP002556399.
Cheng, C. C. et al; Potential Purine Antagonists VII. Synthesis of 6-Alkylpyrazolo-[3,4-d]pyrimidinesn Potential Purine Antagonist VII; Gazz. Chim. Ital., (1958) vol. 23, pp. 191-200.

(56) References Cited

OTHER PUBLICATIONS

Ciba Geigy AG, "Nucleosides and oligonucleotides and 2'-ether groups," Data Supplied from the espacenet database, Publication Date: Nov. 30, 1994; English Abstract of EPO 626 387.
DeNinno et al. "The discovery of potent, selective, and orally bioavailable PDE9 . . . ", Bioorganic & Medicinal Chemistry Letters, 2009, vol. 19, pp. 2537-2541.
Doerwald et al., "Side reactions in organic synthesis," A Guide to Successful Synthesis Design, 2005, 4 pages.
Ebert et al., "Scopolamine model of demential: electroencephalogram findings and cognitive performance," Europ J of Clinical Investigation, 1998, vol. 28, No. 11, pp. 944-949.
Farlow, Martin, R; Pharmacokinetic Profiles of Currect Therapies for Alzheimer's Disease: Implications for Switching to Galantamine; Clinical Therapeutics (2001) vol. 23, Suppl. A, pp. A13-A-24.
Fawcett, Lindsay et al; "Molecular Cloning and Characterization of a Distinct Human . . . ", Proc. Natl. Acad. Science, 2000, vol. 97, No. 7, pp. 3702-3707.
Fischer, Douglas A., et al; "Isolation and Characterization of PDE9A, A Novel . . . ", J. of Biological Chemistry, 1998, vol. 273, No. 25, pp. 15559-15564.
Fisher, Douglas A, et al; "Isolation and Characterization of PDE8A, a Novel . . . ", Biochemical and Biophysical Research Communications, 1998, vol. 246, pp. 570-577.
Francis et al; Cortical Pyramidal Neurone Loss May Cause Glutamatergic Hypoativity and Cognitive Impairment in Alzheimer's Disease: investigative and Therapeutic Perspectives; Journal of Neurochemistry (1993) vol. 60, No. 5, pp. 1589-1604.
Francis, Paul T; "Glutamatergic Systems in Alzheimer's Disease" International Journal of Geriatic Psychiatry (2003) vol. 18, pp. S15-S21.
Francis, Sharron H., et al; "Characterization of a Novel cGMP Binding Protein form Rat Lung . . . ", J. of Biological Chemistry, vol. 255, No. 2, pp. 620-626, (1980).
Fujhishige et al; Cloning and Characterization of a Novel Human Phosphodiesterase That Hydrolyzes Both cAMP and cGMP (PDE10A); Journal of Bilogical Chemistry (1999) vol. 274, No. 26, pp. 18438-18445.
Gielen, Hieke et al; A Novel Approach to Amidines from Esters; Tetrahedron Letters (2002) vol. 43 pp. 419-421.
Gillespie et al; Characterization of a Bovine Cone Photoreceptor Phosphodiesterase Purified by Cyclic Cyclic Gmp-Sepharose Chromatography; J. of Biological Chemistry (1988) vol. 263, No. 17, pp. 8133-8141.
Gompper, Rudolf et al; Substituted Dithiocarboxylic Acids and Ketene Thioacetals; Institute for Organic Chemistry Technology (1962) vol. 95, pp. 2861-2870. German & English Translation.
Guipponi, Michel et al; Identification and Characterization of a Novel Cyclic Nucleotide Phosphodiesterase Gene (PDE9A) that Maps to 21q22.3: Alternative Splicing of mRNA Transcripts, Genomic Structure and Sequence; Hum Genet (1998) vol. 103, pp. 386-392.
Harb, A.-F. A., et al; Pyrazoles as Building Blocks in Heterocyclic Synthesis: Synthesis of Some Ne Substituted 1-Triazinylpyrazolo[3,4-d]pyrimidine and 1-Triazinylpyrazolo[3,4-b]pyridine Derivates; Chemical Papers (2005) vol. 59, No. 3, pp. 187-195.
Hendrix et al; "6-cyclymethyl-and 6-alkylmethyl-Substituted Pyrazolopyrimidines," Publication Date: Nov. 18, 2004, Data Supplied from the espacenet database Worlwide; Englisch Abstract of WO 2004099211.
Hendrix et al; "Use of Pyrazolopyrimidine Against Cardiovascular Disease," Publication Date: Nov. 30, 2006, Data Supplied from the espacenet database Worldwide; English Abstract or WO 20060125548.
Hetman, J. M., et al; Cloning and Characterization of PDE7B, a cAMP-Specific Phosphodiesterase; Proc, Natl. Acad. Science (2000) vol. 97, No. 1, pp. 472-476.
http://www.nlm.nih.gov/medlineplus/ency/article/000746.htm, last accessed Jul. 15, 2010.
Huettner et al; Primary Culture of Identified Neurons from the Visual Cortex of Postnatal Rats; Journal of Neuroscience (1986) vol. 6, No. 10, pp. 3044-3060.
Hung et al., "A high-yielding synthesis of monalkylhydrazines," Journal of Organic Chemistry, 1981, vol. 46, pp. 5413-5414.
International Search Report for PCT/EP2008/066350 dated Feb. 23, 2009.
International Search Report for PCT/EP2009/053907 dated May 26, 2009.
International Search Report for PCT/EP2009/061455 dated Mar. 17, 2011.
International Search Report for PCT/EP2010/054050 dated May 27, 2010.
International Search Report for PCT/EP2010/061735 dated Sep. 24, 2010.
International Search Report for PCT/EP2004/006477 dated Oct. 27, 2004.
International Search Report for PCT/EP2004/014872 dated May 19, 2005.
International Search Report of PCT/EP2003/08880 dated Apr. 16, 2004.
International Search Report of PCT/EP2003/08923 dated Dec. 15, 2003.
International Search Report of PCT/EP2003/08979 dated Nov. 25, 2003.
International Search Report of PCT/EP2004/004412 dated Jul. 14, 2004.
International Search Report of PCT/EP2004/004455 dated Sep. 17, 2004.
Loughney, Kate, et al; Isolation and Characterization of cDNAs Corresponding to Two human Calcium, Calmodulin-regulated, 3',5'-Cyclic Nucleotide Phosphodiesterases; The Journal of Biological Chemistry (1996) vol. 271, No. 2, pp. 796-806.
Loughney, Kate, et al; Isolation and Characterization of cDNAs Encoding PDE5A, a Human cGMP-Bing, cGMP-Specific 3',5'-cyclic Nucleotide Phosphodiesterase; Gene (1998) vol. 216, pp. 139-147.
Lugnier, Claire; Cyclic Nucleotide Phosphodiesterase (PDE) Superfamily: A New Target for the Development of Specific Therapeutic Agents; Pharmacology & Therapeutics; (2006) vol. 109, pp. 366-398.
Markwalder, J. A. et al; Synthesis and Biological Evaluation of 1-Aryl-4,5-dihydro-1H-pyrazolo[3,4-d]pyrimidin-4-one Inhibitors of Cyclin-Dependent Kinases; J. of Med Chemistry (2004) vol. 47, pp. 5894-5911.
Martins, Timothy, J., et al; Purification and Characterization of a Cyclic GMP-stimulated Cyclic Nucleotide Phosphodiesterase from Bovine Tissues; The Journal of Biological Chemistry (1982) vol. 257, No. 4, pp. 1973-1979.
Merriam-Webster's Collegiate Dictionary, published 1998 by Merriam-Webster Inc. p. 924.
Miki, Takashi, et al; Characterization of the cDNA and Gene Encoding Human PDE3B, the cGIP1 Isoform of the Human Cyclic GMP-Inhibited Cyclic Nucleotide Phosphodiesterase Family; Genomics (1996) vol. 36, pp. 476-485.
Miyashita, A., et al; Studies on Pyrazolo[3,4-d]pyrimidine Derivatives XVIII Facile Preparation of 1H-Pyrazolo[3,4-d]Pyrimidin-4(5H)-Ones; Heterocycles (1990) vol. 31, No. 7, pp. 1309-1314.
Murashima, Seiko., et al; Characterization of Particulate Cyclic Nucleotide Phosphodiesterases from Bovine Brain: Purification of a Distinct cGMP-Stimulated Isoenzyme; Biochemistry (1990) vol. 29, No. 22, pp. 5285-5292.
Obernolte, Rena, et al; The cDNA of a Human Lymphocyte Cyclic AMP Phosphodiesterase (PDE IV) Reveals a Multigene Family; Gene (1993) vol. 129, pp. 239-247.
Podraza, Kenneth F.; Reductive Cyclization of Ketoesters Utilizing Sodium Cyanoborohydride: Synthesis of ?- and ?-Lactones; J. Heterocyclic Chem (1987) vol. 24. pp. 293.
Prickaerts et al; Possible Role of Nitric Oxide-Cyclic GMP Pathway in Object Recognition Memory: Effects of 7 Nitroindazole and Zaprinast; Europ J of Pharmacology (1997) vol. 337, No. 2-3, pp. 125-136.

(56) References Cited

OTHER PUBLICATIONS

Prickaerts, J. et al; Effects of Two Selective Phosphodiesterase Type 5 Inhibitors, Sildenafil and Vardenafil, on Object Recognition Memory and Hippocampal Cyclic GMP Levels in the Rat; Neuroscience (2002) vol. 113, No. 2, pp. 351-361.
Puzzo, Daniela, et al; Amyloid-b Peptide Inhibits Activation of the Nitric Oxide/cGMP/cAMP-Responsive Element-Binding Protein Pathway During Hippocampal Synaptic Plasticity; The Journal of Neuroscience (2005) vol. 25, No. 29, pp. 6887-6897.
Reddy, K. Hemender et al; Versatile Synthesis of 6-Alkyl/Aryl-1H-Pyrazolo[3,4-d]Pyrimidin-4[5H]-Ones; Indian Journal of Chemistry (1992) vol. 31B, pp. 163-166.
Reid I. A.; Role of Phosphodiesterase Isozymes in the Control of Renin Secretion: Effects of Selective Enzyme Inhibitors; Current Pharmaceutical Design (1999) vol. 5, No. 9, pp. 725-735.
Related U.S. Appl. No. 12/855,129, filed Aug. 12, 2010.
Related U.S. Appl. No. 12/935,686, filed Sep. 30, 2010.
Related U.S. Appl. No. 13/062,625, filed Mar. 7, 2011.
Related U.S. Appl. No. 13/099,064, filed May 2, 2011.
Reymann, Klaus, et al; The Late Maintenance of Hippocampal LTP: Requirements, Phases, 'Synaptic Tagging', 'Late-Associativity' and Implications; Neuropharmacology (2007) vol. 52, pp. 24-40.
Roenn, Magnus et al; Palladium (II)-Catalyzed Cyclization Using Molecular Oxygen as Reoxidant; Tetrahedron Letters (1995) vol. 36, No. 42, pp. 7749-7752.
Rosman, Guy, J., et al; Isolation and Characterization of Human cDNSs Encoding a cGMP-Stimulated 3',5'-Cyclic Nucleotide Phosphodiesterase; Gene (1997) vol. 191, pp. 89-95.
Schmidt, Richard, R. et al; Pyrazolo[3, 4-d]Pyrimidin-Nucleoside; Chemische Berichte (1977) vol. 110, pp. 2445-2455.
Schmidt, von P., et al; Heilmittelchemische Studien in der Heterocyclischen Reihe; Helvetica Chimica Acta (1962) vol. 62, No. 189, pp. 1620-1627.
Schousboe, Arne et al; Role of Ca++ and Other Second Messengers in Excitatory Amino Acid Receptor Mediated Neuogeneration: Clinical Perspective; Clinical Neuroscience (1997) vol. 4, pp. 194-198.
Skipper, Howard, E., et al; Structure-Activity Relationships Observed on Screening a Series of Pyrazolopyrimidines Against Experimental Neoplasms; Cancer Research (1957) vol. 17, pp. 579-596.
Soderling, Scott, H. et al; Identification and Characterization of a Novel Family of Cyclic Nucleotide Phosphodiesterases; The Journal of Biological Chemistry (1998) vol. 273, No. 25, pp. 15553-15558.
Soderling, Scott, H. et al; Regulation of cAMP and cGMP signalling: New Phosphodiesterases and New Functions; Current Opinion in Cell Biology (2000) vol. 12, pp. 174-179.
Thomson Innovation Record View, Publication Date: Apr. 18, 1963; English Abstract of DE 1147234B.
Thomson Innovation Record View, Publication Date: Aug. 15, 1965; English Abstract of CH 396 923.
Thomson Innovation Record View, Publication Date: May 22, 1963; English Abstract of DE 1149013B.
Timberlake, J.W. et al; Preparative Procedures: Chemistry of Hydrazo-, Azo-, and Azoxy Groups; Patai (1975) Chapter 4, pp. 69-107.
U.S. Appl. No. 12/545,175, filed Aug. 21, 2009, Inventor: Matthias Eckhardt.
U.S. Appl. No. 12/892,310, filed Sep. 28, 2010. Inventor: Dirk Weber.
U.S. Appl. No. 12/892,326, filed Sep. 28, 2010. Inventor: Dirk Weber.
U.S. Appl. No. 12/894,385, filed Sep. 30, 2010. Inventor: Peter Schneider.
U.S. Appl. No. 13/079,424, filed Apr. 4, 2011. Inventor: Matthias Eckhardt.
U.S. Appl. No. 13/369,596, filed Feb. 9, 2012. Inventor: Niklas Heine.
U.S. Appl. No. 13/369,623, filed Feb. 9, 2012. Inventor: Niklas Heine.
Ugarkar, Bheemarao, et al; Synthesis and antiviral/Antitumor Activities of Certain Pyrazolo[3,4-d]pyrimidine-4(5H)-selone Nucleosides and Related compounds; Journal of Medicinal Chemistry (1984) vol. 27, No. 8, pp. 1026-1030.
Ulrich, Joachim; Crystallization; Kirk-Othmer Encyclopedia of Chem Techn (2002) 7 pages.
Van Der Staay, F. Josef., et al; The Novel Selective PDE9 Inhibitor BAY 73/6691 Improves Learning and Memory in Rodents; Neuropharmacology (2008) vol. 55, pp. 908-916.
Van Staveren, W. C. G., et al; Cloning and localization of the cGMP-specific Phosphodiesterase Type 9 in the Rat Brain; Journal of Neurocytology (2002) vol. 31, pp. 729-741.
Vippagunta, Sudha, R., et al; Crystalline Solids; Advanced Drug Delivery Reviews (2001) vol. 48, pp. 3-26.
Wang, Huanchen, et al; Insight Into Binding of Phosphodiesterase-9-A Selective Inhibitors by Crystal Structures and Mutagenesis; Journal of Medicinal Chemistry (2009) pp. 1-6.
Wang, Peng., et al; Identification and Characterization of a New Human Type 9 cGMP-specific Phosphodiesterase-Splice Variant (PDE9A5) Different Tissue Distribution and Subcellular Localization of PDE9A Variants; Gene (2003) vol. 314, pp. 15-27.
Weeber, Edwin, et al; Molecular Genetics of Human Cognition; Molecular Interventions (2002) vol. 2, No. 6, pp. 376-391.
Wei, Ji-Ye, et al; Molecular and Pharmacological Analysis of Cyclic Nucloeotide-Gated Channel Function in the Central Nervous System; Progress in Neurobiology (1998) vol. 56, pp. 37-64.
West, Anthony, R; Solid Solutions; Department of Chemistry, Univesity of Aberdeen (1988) vol. 10 3 pages.
Wunder, Frank et al; Characterization of the First Potent and Selective PDE9 Inhibitor Using a cGMP Reporter Cell Line; Molecular Pharmacology (2005) vol. 68, No. 6 pp. 1775-1781.

* cited by examiner

1,5-DIHYDRO-PYRAZOLO (3, 4-D) PYRIMIDIN-4-ONE DERIVATIVES AND THEIR USE AS PDE9A MUDULATORS FOR THE TREATMENT OF CNS DISORDERS

This application is the national phase entry under 35 U.S.C. §371 of International Application No. PCT/EP2008/066350, filed Nov. 27, 2008, which claims priority to European Patent Application No. 07425764.3, filed Nov. 30, 2007; European Patent Application No. 08163548.4, filed Sep. 3, 2008 and European Patent Application 08169282.4 filed Nov. 17, 2008, which are hereby incorporated by reference in their entireties.

The invention relates to novel substituted pyrazolopyrimidines. The new compounds shall be used for the manufacture of medicaments, in particular medicaments for improving perception, concentration, learning and/or memory in patients in need thereof. E.g. for the prophylaxis and treatment of Alzheimer Disease.

Chemically, the compounds are characterised as 6-aryl- or heteroarylmethyl-substituted pyrazolopyrimidines (more specific 6-benzyl or pyridyl-methyl-pyrazolopyrimidinones) having at least one alkyl or alkoxy residue at the aryl or heteroaryl moiety which in addition may be several fold substituted. Further aspects of the present invention refer to a process for the manufacture of the compounds and their use for producing medicaments.

BACKGROUND OF THE INVENTION

The inhibition of phosphodiesterase 9A (PDE9A) is one of the current concepts to find new access paths to the treatment of cognitive impairments due to CNS disorders like Alzheimer's Disease. With the present invention, new compounds are presented that follow this concept.

Phosphodiesterase 9A is one member of the wide family of phosphordiesterases. These kinds of enzymes modulate the levels of the cyclic nucleotides 5'-3' cyclic adenosine monophosphate (cAMP) and 5'-3' cyclic guanosine monophosphate (cGMP). These cyclic nucleotides (cAMP and cGMP) are important second messengers and therefore play a central role in cellular signal transduction cascades. Each of them reactivates inter alia, but not exclusively, protein kinases. The protein kinase activated by cAMP is called protein kinase A (PKA), and the protein kinase activated by cGMP is called protein kinase G (PKG). Activated PKA and PKG are able in turn to phosphorylate a number of cellular effector proteins (e.g. ion channels, G-protein-coupled receptors, structural proteins, transcription factors). It is possible in this way for the second messengers cAMP and cGMP to control a wide variety of physiological processes in a wide variety of organs. However, the cyclic nucleotides are also able to act directly on effector molecules. Thus, it is known, for example, that cGMP is able to act directly on ion channels and thus is able to influence the cellular ion concentration (review in: Wei et al., *Prog. Neurobiol.*, 1998, 56, 37-64). The phosphodiesterases (PDE) are a control mechanism for controlling the activity of cAMP and cGMP and thus in turn for these physiological processes. PDEs hydrolyse the cyclic monophosphates to the inactive monophosphates AMP and GMP. Currently, 11 PDE families have been defined on the basis of the sequence homology of the corresponding genes. Individual PDE genes within a family are differentiated by letters (e.g. PDE1A and PDE1B). If different splice variants within a gene also occur, this is then indicated by an additional numbering after the letters (e.g. PDE1A1).

Human PDE9A was cloned and sequenced in 1998. The amino acid identity with other PDEs does not exceed 34% (PDE8A) and is never less than 28% (PDE5A). With a Michaelis-Menten constant (Km) of 170 nM, PDE9A has high affinity for cGMP. In addition, PDE9A is selective for cGMP (Km for cAMP=230 [mu]M). PDE9A has no cGMP binding domain, suggesting that the enzyme activity is not regulated by cGMP. It was shown in a Western blot analysis that PDE9A is expressed in humans inter alia in testes, brain, small intestine, skeletal muscle, heart, lung, thymus and spleen. The highest expression was found in the brain, small intestine, kidney, prostate, colon, and spleen (Fisher et al., *J. Biol. Chem.*, 1998, 273 (25), 15559-15564; Wang et al., *Gene*, 2003, 314, 15-27). The gene for human PDE9A is located on chromosome 21q22.3 and comprises 21 exons. To date, 4 alternative splice variants of PDE9A have been identified (Guipponi et al., *Hum. Genet.*, 1998, 103, 386-392). Classical PDE inhibitors do not inhibit human PDE9A. Thus, IBMX, dipyridamole, SKF94120, rolipram and vinpocetine show no inhibition on the isolated enzyme in concentrations of up to 100 [mu]M. An IC50 of 35 [mu]M has been demonstrated for zaprinast (Fisher et al., *J. Biol. Chem.*, 1998, 273 (25), 15559-15564).

Murine PDE9A was cloned and sequenced in 1998 by Soderling et al. (*J. Biol. Chem.*, 1998, 273 (19), 15553-15558). This has, like the human form, high affinity for cGMP with a Km of 70 nM. Particularly high expression was found in the mouse kidney, brain, lung and liver. Murine PDE9A is not inhibited by IBMX in concentrations below 200 [mu]M either; the IC50 for zaprinast is 29 [mu]M (Soderling et al., *J. Biol. Chem.*, 1998, 273 (19), 15553-15558). It has been found that PDE9A is strongly expressed in some regions of the rat brain. These include olfactory bulb, hippocampus, cortex, basal ganglia and basal forebrain (Andreeva et al., *J. Neurosci.*, 2001, 21 (22), 9068-9076). The hippocampus, cortex and basal forebrain in particular play an important role in learning and memory processes. As already mentioned above, PDE9A is distinguished by having particularly high affinity for cGMP. PDE9A is therefore active even at low physiological concentrations, in contrast to PDE2A (Km=10 [mu]M; Martins et al., *J. Biol. Chem.*, 1982, 257, 1973-1979), PDE5A (Km=4 [mu]M; Francis et al., *J. Biol. Chem.*, 1980, 255, 620-626), PDE6A (Km=17 [mu]M; Gillespie and Beavo, *J. Biol. Chem.*, 1988, 263 (17), 8133-8141) and PDE11A (Km=0.52 [mu]M; Fawcett et al., *Proc. Nat. Acad. Sci.*, 2000, 97 (7), 3702-3707). In contrast to PDE2A (Murashima et al., *Biochemistry*, 1990, 29, 5285-5292), the catalytic activity of PDE9A is not increased by cGMP because it has no GAF domain (cGMP-binding domain via which the PDE activity is allosterically increased) (Beavo et al., *Current Opinion in Cell Biology*, 2000, 12, 174-179). PDE9A inhibitors may therefore lead to an increase in the baseline cGMP concentration.

WO 98/40384 discloses pyrazolopyrimidines which are PDE1, 2 and 5 inhibitors and can be employed for the treatment of cardiovascular and cerebrovascular disorders and disorders of the urogenital system.

CH 396 924, CH 396 925, CH 396 926, CH 396 927, DE 1 147 234, DE 1 149 013, GB 937,726 describe pyrazolopyrimidines which have a coronary-dilating effect and which can be employed for the treatment of disturbances of myocardial blood flow.

U.S. Pat. No. 3,732,225 describes pyrazolopyrimidines which have an antiinflammatory and blood glucose-lowering effect.

DE 2 408 906 describes styrylpyrazolopyrimidines which can be employed as antimicrobial and antiinflammatory agents for the treatment of, for example, oedema.

WO04099210 discloses novel 6-arylmethyl-substituted pyrazolopyrimidines which lack having at least one alkyl or alkoxy residue at the aryl moiety which is several fold substituted by halogen.

ASPECTS OF THE INVENTION

It is an aspect of the present invention to provide compounds that effectively modulate PDE9A for the purpose of the development of a medicament, in particular in view of diseases, the treatment of which is accessible via PDE9A modulation.

It is another aspect of the present invention to provide compounds that are useful for the manufacture of a medicament for the treatment of CNS disorders.

It is an aspect of one embodiment of the present invention to provide compounds which show a good safety profile.

Accordingly, it will be understood that another objective of the present invention is to provide compounds that inhibit PDE9A in a selective manner.

Yet another objective is to provide such a medicament not only for treatment but also for prevention or modification of the corresponding disease.

DETAILED DESCRIPTION OF THE PRESENT INVENTION

The compounds of the present invention are characterised by general formula I:

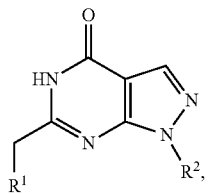

(I)

with:
$R^1$: the following substitution options $R^{1.i}$ for $R^1$ in the order of preference, ascending from preferably to most preferably are defined:
$R^{1.1}$: $R^1$ being phenyl or pyridyl, preferably phenyl, any of which is substituted with 1 to 4, preferably 1 to 3 substituents independently selected from X,
and with the option that each of phenyl or pyridyl in addition may be substituted by up to 3 radicals independently of one another selected from the group of $C_1$-$C_6$-alkyl, $C_1$-$C_6$-alkoxy, hydroxycarbonyl, cyano, trifluoromethyl, amino, nitro, hydroxy, $C_1$-$C_6$-alkylamino, halogen, $C_6$-$C_{10}$-arylcarbonylamino, $C_1$-$C_6$-alkylcarbonylamino, $C_1$-$C_6$-alkylaminocarbonyl, $C_1$-$C_6$-alkoxycarbonyl, $C_6$-$C_{10}$-arylaminocarbonyl, heteroarylaminocarbonyl, heteroarylcarbonylamino, $C_1$-$C_6$-alkylsulphonylamino, $C_1$-$C_6$-alkylsulphonyl, $C_1$-$C_6$-alkylthio,
where each of $C_1$-$C_6$-alkyl, $C_1$-$C_6$-alkoxy, $C_1$-$C_6$-alkylamino, $C_6$-$C_{10}$-arylcarbonylamino, $C_1$-$C_6$-alkylcarbonylamino, $C_1$-$C_6$-alkylaminocarbonyl, $C_1$-$C_6$-alkoxycarbonyl, $C_6$-$C_{10}$-arylaminocarbonyl, heteroarylaminocarbonyl, heteroarylcarbonylamino, $C_1$-$C_6$-alkylsulphonylamino, $C_1$-$C_6$-alkylsulphonyl and $C_1$-$C_6$-alkylthio are optionally substituted by 1 to 3 radicals independently of one another selected from the group of hydroxy, cyano, halogen, hydroxycarbonyl and a group of the formula —$NR^3R^4$,
with X (—independently of each other in case of more than one X—) being $C_2$-$C_6$-alkyl or $C_1$-$C_6$-alkoxy; each of which are at least dihalogenated up to perhalogenated and the halogen atoms being selected from the group of fluoro, chloro and bromo, preferably fluoro. Preferred are substitution patterns in that at least the C-atom which constitutes the beta position with respect to the link to the phenyl or pyridyl is at least one fold or more preferred at least twofold halogenated. The beta position is the position next to the O-atom in case of $C_1$-$C_6$-alkoxy and in case of $C_2$-$C_6$-alkyl the C-atom next to the C-atom that is linked to the phenyl or pyridyl. For each embodiment of the present invention X preferably is $C_1$-alkyl-O or $C_2$-alkyl substituted as defined hereinbefore.
Preferably at least one X is in the ortho position to the C-atom of the phenyl-ring, the pyridylring respectively by which $R^1$ is attached to the methylene group which links $R^1$ with the pyrazolopyrimidine group of the of formula I.
$R^{1.2}$: $R^1$ being phenyl or pyridyl, preferably phenyl, any of which is substituted with 1 to 4, preferably 1 to 3 substituents independently selected from X, where X is substituted by at least 2, preferably 2 to 6 halogen atoms, selected from the group of fluoro, chloro and bromo, preferably fluoro substitutents
and with the option that each of phenyl or pyridyl in addition may be substituted by up to 3 radicals independently of one another selected from the group of $C_1$-$C_6$-alkyl, $C_1$-$C_6$-alkoxy, cyano, trifluoromethyl, nitro, halogen, $C_6$-$C_{10}$-arylcarbonylamino, $C_1$-$C_6$-alkylcarbonylamino, $C_1$-$C_6$-alkylaminocarbonyl, $C_6$-$C_{10}$-arylaminocarbonyl, heteroarylaminocarbonyl, heteroarylcarbonylamino, $C_1$-$C_6$-alkylsulphonylamino, $C_1$-$C_6$-alkylsulphonyl, $C_1$-$C_6$-alkylthio,
where each of $C_1$-$C_6$-alkyl, $C_1$-$C_6$-alkoxy, $C_6$-$C_{10}$-arylcarbonylamino, $C_1$-$C_6$-alkylcarbonylamino, $C_1$-$C_6$-alkylaminocarbonyl, $C_6$-$C_{10}$-arylaminocarbonyl, heteroarylaminocarbonyl, heteroarylcarbonylamino, $C_1$-$C_6$-alkylsulphonylamino, $C_1$-$C_6$-alkylsulphonyl and $C_1$-$C_6$-alkylthio are optionally substituted by 1 to 3 radicals independently of one another selected from the group of hydroxy, cyano, halogen, and a group of the formula —$NR^3R^4$,
with X (—independently of each other in case of more than one X—) being $C_2$-$C_6$-alkyl or $C_1$-$C_6$-alkoxy; each of which are at least dihalogenated up to perhalogenated and the halogen atoms being selected from the group of fluoro, chloro and bromo, preferably fluoro. Preferred are substitution patterns in that at least the C-atom which constitutes the beta position with respect to the link to the phenyl or pyridyl is at least one fold or more preferred at least twofold halogenated. The beta position is the position next to the O-atom in case of $C_1$-$C_6$-alkoxy and in case of $C_2$-$C_6$-alkyl the C-atom next to the C-atom that is linked to the phenyl or pyridyl. For each embodiment of the present invention X preferably is $C_1$-alkyl-O or $C_2$-alkyl substituted as defined hereinbefore.
Preferably at least one X is in the ortho position to the C-atom of the phenyl-ring or the pyridylring respectively by which $R^1$ is attached to the methylene group which links $R^1$ with the pyrazolopyrimidine group of the of formula I.
$R^{1.3}$: $R^1$ being phenyl or pyridyl, preferably phenyl, any of which is substituted with 1 to 4, preferably 1 to 3 substituents independently selected from X, where X is substituted by at least 2, preferably 2 to 6 halogen atoms, selected from the group of fluoro, chloro and bromo, preferably fluoro substitutents and with the option that each of phenyl or pyridyl in addition may be substituted by up to 3 radicals independently of one another selected from the group of $C_1$-$C_6$-alkyl, trifluoromethyl, halogen, with X (—independently of each other in case of more than one X—) being $C_2$-$C_6$-alkyl or $C_1$-$C_6$-alkoxy; each of which are at least dihalogenated up to perhalogenated and the halogen atoms being selected from the group of fluoro, chloro and bromo, preferably fluoro. Preferred are substitution patterns in that at least the C-atom which constitutes the beta position with respect to the link to the phenyl or pyridyl is at least one fold or more preferred at least twofold halogenated. The beta position is the position next to the O-atom in case of $C_1$-$C_6$-alkoxy and in case of $C_2$-$C_6$-alkyl the C-atom next to the C-atom that is linked to the phenyl or pyridyl. For each embodiment of the present invention X preferably is $C_1$-alkyl-O or $C_2$-alkyl substituted as defined hereinbefore.

Preferably at least one X is in the ortho position to the C-atom of the phenyl-ring or the pyridylring respectively by which $R^1$ is attached to the methylene group which links R1 with the pyrazolopyrimidine group of the of formula I.

In another embodiment of the invention, $R^1$ being $R^{1.i.a}$ with i as being defined above (i.e. for $R^{1.i}$=$R^{1.1}$, $R^{1.2}$, $R^{1.3}$):

$R^{1.1.a}$: $R^1$ being $R^{1.1}$ with X being $C_2$-$C_6$-alkyl; more preferably $C_2$-alkyl, being substituted by at least 2 halogen atoms, being selected from the group of fluoro, chloro and bromo, preferably fluoro. Preferably the beta position to the link between X and phenyl or pyridyl is at least twofold substituted, the term beta position is as defined for the same context under $R^{1.1}$;

$R^{1.2.a}$: $R^1$ being $R^{1.2}$ with X being $C_2$-$C_6$-alkyl; more preferably $C_2$-alkyl, being substituted by at least 2 halogen atoms, being selected from the group of fluoro, chloro and bromo, preferably fluoro. Preferably the beta position to the link between X and phenyl or pyridyl is at least twofold substituted;

$R^{1.3.a}$: $R^1$ being $R^{1.3}$ with X being $C_2$-$C_6$-alkyl; more preferably $C_2$-alkyl, being substituted by at least 2 halogen atoms, being selected from the group of fluoro, chloro and bromo, preferably fluoro. Preferably the beta position to the link between X and phenyl or pyridyl is at least twofold substituted;

Preferably in any of the embodiments $R^{1.1.a}$, $R^{1.2.a}$, $R^{1.3.a}$ at least one X is in the ortho position to the C-atom of the phenyl-ring or the pyridylring respectively by which $R^1$ is attached to the methylene group which links R1 with the pyrazolopyrimidine group of the of formula I.

In another embodiment of the invention, $R^1$ being $R^{1.i.b}$ with i as being defined above (i.e. for $R^{1.i}$=$R^{1.1}$, $R^{1.2}$, $R^{1.3}$):

$R^{1.1.b}$: $R^1$ being $R^{1.1}$ with X being $C_1$-$C_6$-alkoxy; more preferably $C_1$-alkoxy, being substituted by at least 2 halogen atoms, being selected from the group of fluoro, chloro and bromo, preferably fluoro. Preferably the beta position to the link between X and phenyl or pyridyl is at least twofold substituted;

$R^{1.2.b}$: $R^1$ being $R^{1.2}$ with X being $C_1$-$C_6$-alkoxy; more preferably $C_1$-alkoxy, being substituted by at least 2 halogen atoms, being selected from the group of fluoro, chloro and bromo, preferably fluoro. Preferably the beta position to the link between X and phenyl or pyridyl is at least twofold substituted;

$R^{1.3.b}$: $R^1$ being $R^{1.3}$ with X being $C_1$-$C_6$-alkoxy; more preferably $C_1$-alkoxy, being substituted by at least 2 halogen atoms, being selected from the group of fluoro, chloro and bromo, preferably fluoro. Preferably the beta position to the link between X and phenyl or pyridyl is at least twofold substituted;

$R^{1.4.b}$: $R^1$ being phenyl or pyridyl, preferably phenyl, any of which is substituted with 1 to 3X being $C_1$-$C_6$-alkoxy, substituted by at least 2, preferably 2 to 6 halogen atoms, selected from the group of fluoro, chloro and bromo, preferably fluoro substitutents, whereby at least twofold halogenation at the position next to the O-atom is preferred, and with the option that each of phenyl or pyridyl in addition may be substituted by up to 3 radicals independently of one another selected from the group of $C_1$-$C_6$-alkyl, trifluoromethyl, halogen, $R^{1.5.b}$: $R^1$ being 2-trifluoromethoxyphen-1-yl.

Preferably in any of the embodiments $R^{1.1.b}$, $R^{1.2.b}$, $R^{1.3.b}$, $R^{1.4.b}$ at least one X is in the ortho position to the C-atom of the phenyl-ring, the pyridylring respectively by which $R^1$ is attached to the methylene group which links $R^1$ with the pyrazolopyrimidine group of the of formula I.

For all substitution patterns $R^{1.1}$, $R^{1.2}$, $R^{1.3}$, $R^{1.1.a}$, $R^{1.2.a}$, $R^{1.3.a}$, $R^{1.1.b}$, $R^{1.2.b}$, $R^{1.3.b}$, $R^{1.4.b}$ the preferred substitution pattern at the 1 to 3 mandatory substituents X being $C_2$-$C_6$-alkyl or $C_1$-$C_6$-alkoxy respectively, whatever is appropriate, preferably are at least 2, more preferably 3 fluoro substituents. The preferred position for these halogen substituents are the alpha or the beta position, more preferably at least the beta position of the $C_2$-$C_6$-alkyl residue or the beta position of the $C_1$-$C_6$-alkoxy residue, more preferably only the beta position. Whenever X is $C_1$-$C_6$-alkoxy trifluoromethoxy is preferred. Whenever X is $C_2$-$C_6$-alkyl 2,2,2-trifluoreth-1-yl or 1,2,2,2-tetrafluoreth-1-yl or 1,1,2,2,2-pentafluoreth-1-yl is preferred, more preferred 2,2,2-trifluoreth-1-yl.

For the embodiments with $R^{1.1}$, $R^{1.2}$, $R^{1.3}$, $R^{1.1.b}$, $R^{1.2.b}$, $R^{1.3.b}$, $R^{1.4.b}$ most preferred X is 1 substituent being trifluoromethoxy.

For the embodiments with $R^{1.1.a}$, $R^{1.2.a}$, $R^{1.3.a}$ most preferred X is 1 substituent being 2,2,2-trifluoreth-1-yl or 1,2,2,2-tetrafluoreth-1-yl or 1,1,2,2,2-pentafluoreth-1-yl 2,2,2-trifluoreth-1-yl.

In all options for $R^1$ ($R^{1.1}$, $R^{1.2}$, $R^{1.3}$, $R^{1.1.a}$, $R^{1.2.a}$, $R^{1.3.a}$, $R^{1.1.b}$, $R^{1.2.b}$, $R^{1.3.b}$, $R^{1.4.b}$) phenyl is preferred over pyridyl, with the substitution pattern as outlined above.

In all options for $R^1$ defined by $R^{1.1}$, $R^{1.2}$, $R^{1.3}$, $R^{1.1.a}$, $R^{1.2.a}$, $R^{1.3.a}$, $R^{1.1.b}$, $R^{1.2.b}$, $R^{1.3.b}$ $R^{1.4.b}$ at least one X preferably is in the ortho position to the C-atom of the phenyl-ring or the pyridylring respectively by which $R^1$ is attached to the methylene group which links $R^1$ with the pyrazolopyrimidine group of the of formula I. For the embodiment $R^{1.5.b}$ X is trifluoromethyl in ortho position of the phenyl. As outlined in the definition of the embodiments for $R^1$ defined by $R^{1.1}$, $R^{1.2}$, $R^{1.3}$, $R^{1.1.a}$, $R^{1.2.a}$, $R^{1.3.a}$, $R^{1.1.b}$, $R^{1.2.b}$, $R^{1.3.b}$, $R^{1.4.b}$ X can be present 1, 2, 3 or 4 times. Preferably X is present 1, 2 or 3 times, more preferably 1 or 2 times, more preferably 1 time.

In all options for $R^1$ defined by $R^{1.1}$, $R^{1.2}$, $R^{1.3}$ X being $C_1$-$C_6$-alkoxy is preferred over X being $C_2$-$C_6$-alkyl. Accordingly, any of the options $R^{1.i.b}$ is preferred over any options of $R^{1.i.a}$.

$R^2$: the following substitution options $R^{2.j}$ for $R^2$ in the order of preference, ascending from preferably to most preferably are defined:

$R^{2.1}$ $R^2$ being phenyl or heteroaryl, where phenyl is substituted by 1 to 3 radicals and heteroaryl is optionally substituted by 1 to 3 radicals in each case independently of one another selected from the group of $C_1$-$C_6$-alkyl, $C_1$-$C_6$- alkoxy, hydroxycarbonyl, cyano, trifluoromethyl, amino, nitro, hydroxy, $C_1$-$C_6$-alkylamino, halogen, $C_6$-$C_{10}$-arylcarbonylamino, $C_1$-$C_6$-alkylcarbonylamino, $C_1$-$C_6$-alkylaminocarbonyl, $C_1$-$C_6$-alkoxycarbonyl, $C_6$-$C_{10}$-arylaminocarbonyl, heteroarylaminocarbonyl, heteroarylcarbonylamino, $C_1$-$C_6$-alkylsulphonyl-amino, $C_1$-$C_6$-alkylsulphonyl and $C_1$-$C_6$-alkylthio, where each of $C_1$-$C_6$-alkyl, $C_1$-$C_6$-alkoxy, $C_1$-$C_6$-alkylamino, $C_6$-$C_{10}$-arylcarbonylamino, $C_1$-$C_6$-alkylcarbonylamino, $C_1$-$C_6$-alkylaminocarbonyl, $C_1$-$C_6$-alkoxycarbonyl, $C_6$-$C_{10}$-arylaminocarbonyl, heteroarylaminocarbonyl, heteroarylcarbonylamino, $C_1$-$C_6$-alkylsulphonylamino, $C_1$-$C_6$-alkylsulphonyl and $C_1$-$C_6$-alkylthio are optionally substituted by one to three radicals independently of one another selected from the group of hydroxy, cyano, halogen, hydroxycarbonyl and a group of the formula —$NR^3R^4$, $R^{2.2}$ $R^2$ being phenyl or heteroaryl, where phenyl is substituted by 1 to 3 radicals and heteroaryl is optionally substituted by 1 to 3 radicals in each case independently of one another selected from the group of $C_1$-$C_6$-alkyl, $C_1$-$C_6$-alkoxy, hydroxycarbonyl, cyano, trifluoromethyl, amino, nitro, hydroxy, $C_1$-$C_6$-alkylamino, halogen, $C_1$-$C_6$-alkylcarbonylamino, $C_1$-$C_6$-alkylaminocarbonyl, $C_1$-$C_6$-alkylsulphonylamino, $C_1$-$C_6$-alkylsulphonyl and $C_1$-$C_6$-alkylthio, where each of $C_1$-$C_6$-alkyl, $C_1$-$C_6$-alkoxy, $C_1$-$C_6$-alkylamino, $C_6$-$C_{10}$-arylcarbonylamino, $C_1$-$C_6$-alkylcarbonylamino, $C_1$-$C_6$-alkylaminocarbonyl, $C_1$-$C_6$-alkylsulphonylamino, $C_1$-$C_6$-alkylsulphonyl and $C_1$-$C_6$-alkylthio are optionally substituted by one to three radicals independently of one another selected from the group of hydroxy, cyano, halogen, and a group of the formula $NR^3R^4$, In another embodiment $R^{2.2.a}$ $R^2$ is defined as for $R^{2.2}$ but without hydroxycarbonyl.

$R^{2.3}$ $R^2$ being phenyl or pyridyl, preferably phenyl or 3-pyridyl, where phenyl is substituted by 1 to 3 radicals and pyridyl is optionally substituted by 1 to 3 radicals in each case independently of one another selected from the group of $C_1$-$C_6$-alkyl, $C_1$-$C_6$-alkoxy, trifluoromethyl, halogen and $C_1$-$C_6$-alkylthio, where $C_1$-$C_6$-alkyl, $C_1$-$C_6$-alkoxy and $C_1$-$C_6$-alkylthio, are optionally substituted by one to three halogen radicals, For all substitution patterns according to $R^{2.1}$, $R^{2.2}$, $R^{2.3}$ the preferred substitution pattern at phenyl and heteroaryl is one or two radical(s). Heteroaryl preferably is pyridyl (2-, 3-, 4-pyridyl) optionally having one or two radical(s).

For all substitution patterns according to $R^{2.1}$, $R^{2.2}$, $R^{2.3}$ the preferred heteroaryl is pyridyl, more preferably 3-pyridyl.

$R^3$: $R^3$ having the following substitution option $R^{3.1}$:

$R^{3.1}$ $R^3$ being hydrogen or $C_1$-$C_6$-alkyl, $R^4$: $R^4$ having the following substitution option $R^{4.1}$:

$R^{4.1}$ $R^4$ being hydrogen or $C_1$-$C_6$-alkyl, or $R^3$ and $R^4$ together with the nitrogen atom to which they are bonded are defined as (abbreviation for this kind of definition=$R^{3+4}$, specifically $R^{3+4.1}$):

$R^{3+4.1}$: $R^3$ and $R^4$ together with the nitrogen atom to which they are bonded are 5- to 8-membered heterocyclyl.

Each of the letters or indexes i, j respectively in $R^{1.i}$ and $R^{2.j}$ is an index standing for 1, 2, 3, etc.

Specific embodiments according to the present invention are represented by each element of the following matrix I, matrix II and matrix III. The present invention includes each embodiment of matrix I, matrix II and matrix III, more preferably each embodiment of matrix II and matrix III and more preferably each embodiment of matrix III. The preference of the embodiments for each matrix ascends from the first line to the last line. This means that the embodiment, which is presented by the matrix III, last row (i.e. ($R^{1.5.b}$ $R^{2.3}$)) is the most preferred embodiment.

Each matrix is represented by two columns, one providing the number for an embodiment of the present invention and the other one describing said embodiment.

| matrix I: | |
|---|---|
| No. | embodiment |
| I-1 | $R^{1.1}$ $R^{2.1}$ $R^{3.1}$ $R^{4.1}$ |
| I-2 | $R^{1.1}$ $R^{2.1}$ $R^{3+4.1}$ |
| I-3 | $R^{1.1}$ $R^{2.2}$ $R^{3.1}$ $R^{4.1}$ |
| I-4 | $R^{1.1}$ $R^{2.2}$ $R^{3+4.1}$ |
| I-5 | $R^{1.1}$ $R^{2.3}$ $R^{3.1}$ $R^{4.1}$ |
| I-6 | $R^{1.1}$ $R^{2.3}$ $R^{3+4.1}$ |
| I-7 | $R^{1.2}$ $R^{2.1}$ $R^{3.1}$ $R^{4.1}$ |
| I-8 | $R^{1.2}$ $R^{2.1}$ $R^{3+4.1}$ |
| I-9 | $R^{1.2}$ $R^{2.2}$ $R^{3.1}$ $R^{4.1}$ |
| I-10 | $R^{1.2}$ $R^{2.2}$ $R^{3+4.1}$ |
| I-11 | $R^{1.2}$ $R^{2.3}$ $R^{3.1}$ $R^{4.1}$ |
| I-12 | $R^{1.2}$ $R^{2.3}$ $R^{3+4.1}$ |
| I-13 | $R^{1.3}$ $R^{2.1}$ $R^{3.1}$ $R^{4.1}$ |
| I-14 | $R^{1.3}$ $R^{2.1}$ $R^{3+4.1}$ |
| I-15 | $R^{1.3}$ $R^{2.2}$ $R^{3.1}$ $R^{4.1}$ |
| I-16 | $R^{1.3}$ $R^{2.2}$ $R^{3+4.1}$ |
| I-17 | $R^{1.3}$ $R^{2.3}$ |

| matrix II: | |
|---|---|
| No. | embodiment |
| II-1 | $R^{1.1.a}$ $R^{2.1}$ $R^{3.1}$ $R^{4.1}$ |
| II-2 | $R^{1.1.a}$ $R^{2.1}$ $R^{3+4.1}$ |
| II-3 | $R^{1.1.a}$ $R^{2.2}$ $R^{3.1}$ $R^{4.1}$ |
| II-4 | $R^{1.1.a}$ $R^{2.2}$ $R^{3+4.1}$ |
| II-5 | $R^{1.1.a}$ $R^{2.3}$ $R^{3.1}$ $R^{4.1}$ |
| II-6 | $R^{1.1.a}$ $R^{2.3}$ $R^{3+4.1}$ |
| II-7 | $R^{1.2.a}$ $R^{2.1}$ $R^{3.1}$ $R^{4.1}$ |
| II-8 | $R^{1.2.a}$ $R^{2.1}$ $R^{3+4.1}$ |
| II-9 | $R^{1.2.a}$ $R^{2.2}$ $R^{3.1}$ $R^{4.1}$ |
| II-10 | $R^{1.2.a}$ $R^{2.2}$ $R^{3+4.1}$ |
| II-11 | $R^{1.2.a}$ $R^{2.3}$ $R^{3.1}$ $R^{4.1}$ |
| II-12 | $R^{1.2.a}$ $R^{2.3}$ $R^{3+4.1}$ |
| II-13 | $R^{1.3.a}$ $R^{2.1}$ $R^{3.1}$ $R^{4.1}$ |
| II-14 | $R^{1.3.a}$ $R^{2.1}$ $R^{3+4.1}$ |
| II-15 | $R^{1.3.a}$ $R^{2.2}$ $R^{3.1}$ $R^{4.1}$ |
| II-16 | $R^{1.3.a}$ $R^{2.2}$ $R^{3+4.1}$ |
| II-17 | $R^{1.3.a}$ $R^{2.3}$ |

| matrix III | |
|---|---|
| No. | embodiment |
| III-1 | $R^{1.1.b}$ $R^{2.1}$ $R^{3.1}$ $R^{4.1}$ |
| III-2 | $R^{1.1.b}$ $R^{2.1}$ $R^{3+4.1}$ |
| III-3 | $R^{1.1.b}$ $R^{2.2}$ $R^{3.1}$ $R^{4.1}$ |
| III-4 | $R^{1.1.b}$ $R^{2.2}$ $R^{3+4.1}$ |
| III-5 | $R^{1.1.b}$ $R^{2.3}$ $R^{3.1}$ $R^{4.1}$ |
| III-6 | $R^{1.1.b}$ $R^{2.3}$ $R^{3+4.1}$ |
| III-7 | $R^{1.2.b}$ $R^{2.1}$ $R^{3.1}$ $R^{4.1}$ |
| III-8 | $R^{1.2.b}$ $R^{2.1}$ $R^{3+4.1}$ |
| III-9 | $R^{1.2.b}$ $R^{2.2}$ $R^{3.1}$ $R^{4.1}$ |
| III-10 | $R^{1.2.b}$ $R^{2.2}$ $R^{3+4.1}$ |
| III-11 | $R^{1.2.b}$ $R^{2.3}$ $R^{3.1}$ $R^{4.1}$ |
| III-12 | $R^{1.2.b}$ $R^{2.3}$ $R^{3+4.1}$ |

-continued matrix III

| No. | embodiment |
|---|---|
| III-13 | $R^{1.3.b} R^{2.1} R^{3.1} R^{4.1}$ |
| III-14 | $R^{1.3.b} R^{2.1} R^{3+4.1}$ |
| III-15 | $R^{1.3.b} R^{2.2} R^{3.1} R^{4.1}$ |
| III-16 | $R^{1.3.b} R^{2.2} R^{3+4.1}$ |
| III-17 | $R^{1.3.b} R^{2.3}$ |
| III-18 | $R^{1.4.b} R^{2.1} R^{3.1} R^{4.1}$ |
| III-19 | $R^{1.4.b} R^{2.1} R^{3+4.1}$ |
| III-20 | $R^{1.4.b} R^{2.2} R^{3.1} R^{4.1}$ |
| III-21 | $R^{1.4.b} R^{2.2} R^{3+4.1}$ |
| III-22 | $R^{1.4.b} R^{2.3}$ |
| III-23 | $R^{1.5.b} R^{2.1} R^{3.1} R^{4.1}$ |
| III-24 | $R^{1.5.b} R^{2.1} R^{3+4.1}$ |
| III-25 | $R^{1.5.b} R^{2.2} R^{3.1} R^{4.1}$ |
| III-26 | $R^{1.5.b} R^{2.2} R^{3+4.1}$ |
| III-27 | $R^{1.5.b} R^{2.3}$ |

In any of these embodiments $R^{2.2}$ may be replaced by $R^{2.2.a}$.

For each embodiment according to any of the matrixes I, II or III (i.e. I-1, I-2, I-3, I-4, I-5, I-6, I-7, I-8, I-9, I-10, I-11, I-12, I-13, I-14, I-15, I-16, I-17, II-1, II-2, II-3, II-4, II-5, II-6, II-7, II-8, II-9, II-10, II-11, II-12, II-13, II-14, II-15, II-16, II-17, III-1, III-2, III-3, III-4, III-5, III-6, III-7, III-8, III-9, III-10, III-11, III-12, III-13, III-14, III-15, III-16, III-17, III-18, III-19, III-20, III-21, III-22, III-23, III-24, III-25, III-26, III-27) the definitions and preferences for each substituent as outlined above shall apply, exemplified with a non-limiting character as:

For each substitution pattern for $R^1$ the preferred number of halogen substituents at the 1 to 3 mandatory substituents X (=$C_2$-$C_6$-alkyl or $C_1$-$C_6$-alkoxy respectively, whatever is appropriate,) preferably are 2 to 6. More preferably the number is at least 2, more preferably 3 fluoro substituents. The preferred position for these halogen substituents are the alpha or more preferred the beta position of the $C_2$-$C_6$-alkyl residue or the beta position of the $C_1$-$C_6$-alkoxy residue (in particular it is referred to $R^{1.1}$, $R^{1.2}$, $R^{1.3}$, $R^{1.1.a}$, $R^{1.2.a}$, $R^{1.3.a}$, $R^{1.1.b}$, $R^{1.2.b}$, $R^{1.3.b}$, $R^{1.4.b}$). Whenever X is $C_1$-$C_6$-alkoxy trifluoromethoxy is preferred. Whenever X is $C_2$-$C_6$-alkyl 2,2,2-trifluoreth-1-yl or 1,2,2,2-tetrafluoreth-1-yl or 1,1,2,2,2-pentafluoreth-1-yl is preferred, more preferred 2,2,2-trifluoreth-1-yl. For the embodiments with $R^{1.1}$, $R^{1.2}$, $R^{1.3}$, $R^{1.1.b}$, $R^{1.2.b}$, $R^{1.3.b}$, $R^{1.4.b}$ most preferred X is 1 substituent being trifluoromethoxy. For the embodiments with $R^{1.1.a}$, $R^{1.2.a}$, $R^{1.3.a}$ most preferred X is 1 substituent being 2,2,2-trifluoreth-1-yl or 1,2,2,2-tetrafluoreth-1-yl or 1,1,2,2,2-pentafluoreth-1-yl 2,2,2-trifluoreth-1-yl.

Most preferred X is 1 (one) trifluoromethoxy substituent such as outlined for $R^{1.5.b}$.

In each option for $R^1$ (i.e. $R^{1.1}$, $R^{1.2}$, $R^{1.3}$, $R^{1.1.a}$, $R^{1.2.a}$, $R^{1.3.a}$, $R^{1.1.b}$, $R^{1.2.b}$, $R^{1.3.b}$, $R^{1.4.b}$) at least one X preferably is in the ortho position to the C-atom of the phenyl-ring—the pyridylring respectively—by which $R^1$ is attached to the methylene group which links $R^1$ with the pyrazolopyrimidine group of the of formula I, e.g. $R^{1.5.b}$.

In each option for $R^1$ (i.e. $R^{1.1}$, $R^{1.2}$, $R^{1.3}$, $R^{1.1.a}$, $R^{1.2.a}$, $R^{1.3.a}$, $R^{1.1.b}$, $R^{1.2.b}$, $R^{1.3.b}$, $R^{1.4.b}$) phenyl is preferred over pyridyl, with the substitution pattern as outlined above, e.g. $R^{1.5.b}$.

For each of $R^{2.1}$, $R^{2.2}$, $R^{2.3}$ the preferred substitution pattern at phenyl and heteroaryl is 1 or 2 radical(s). Heteroaryl preferably is pyridyl.

For the purposes of the present invention, the substituents have the following meaning, unless specified otherwise:

$C_1$-$C_6$-Alkoxy is a straight-chain or branched alkoxy radical having 1 to 6, preferably 1 to 4, particularly preferably having 1 to 3 carbon atoms. Preferred examples include methoxy, ethoxy, n-propoxy, isopropoxy, tert-butoxy, n-pentoxy and n-hexoxy.

$C_1$-$C_6$-Alkoxycarbonyl: $C_{1-6}$-Alkoxy is as defined for $C_{1-6}$-alkoxy.

$C_1$-$C_6$-Alkyl is a straight-chain or branched alkyl radical having 1 to 6, preferably 1 to 4, particularly preferably 1 to 3, carbon atoms. Preferred examples include methyl, ethyl, n-propyl, isopropyl, tert-butyl, n-pentyl and n-hexyl.

$C_1$-$C_6$-Alkylamino is a straight-chain or branched mono- or dialkylamino radical the alkyl group(s) therein having 1 to 6, preferably 1 to 4 and particularly preferably having 1 to 3 carbon atoms. Preferred examples include methylamino, ethylamino, n-propylamino, isopropylamino, tert-butylamino, n-pentylamino and n-hexylamino, dimethylamino, diethylamino, di-n-propylamino, diisopropylamino, di-t-butylamino, di-n-pentylamino, di-n-hexylamino, ethylmethylamino, isopropylmethylamino, n-butylethylamino and n-hexyl-i-pentylamino. In the context of the present invention it is understood that for each time this term is used, it shall be understood that this substituent may be mono-alkylamino (=$C_{1-6}$-Alkyl-NH—) and/or dialkylamino (=N—$C_{1-6}$-Alkyl-N($C_{1-6}$-Alkyl)'-amino-). In the dialkyl-variation thereof, the two alkyl groups may be the same or different ones.

$C_1$-$C_6$-Alkylaminocarbonyl is a mono- or dialkylamino radical linked via a carbonyl group, where in the dialkyl variation thereof the alkyl radicals may be identical or different. The alkyl group(s) may be straight-chain or branched and each comprise 1 to 6, preferably 1 to 4 and particularly preferably 1 to 3 carbon atoms. In the context of the present invention it is understood that for each time this term is used, it shall be understood that this substituent may be mono-alkylaminocarbonyl (=$C_{1-6}$-Alkyl-NH—CO—) and/or dialkylamino. (=N—$C_{1-6}$-Alkyl-N—($C_{1-6}$-Alkyl)'-N—CO—). In the dialkyl-variation thereof, the two alkyl groups may be the same or different ones. Preferred examples include methylaminocarbonyl, ethylaminocarbonyl, n-propylaminocarbonyl, isopropylaminocarbonyl, tert-butylaminocarbonyl, n-pentylaminocarbonyl, n-hexylaminocarbonyl, dimethylaminocarbonyl, diethylaminocarbonyl, di-n-propylaminocarbonyl, diisopropylaminocarbonyl, di-t-butylamino-carbonyl, di-n-pentylaminocarbonyl, di-n-hexylaminocarbonyl, ethylmethylaminocarbonyl, isopropylmethylaminocarbonyl, n-butylethylaminocarbonyl and n-hexyl-i-pentylaminocarbonyl. A further possibility in the case of a dialkylaminocarbonyl radical is for the two alkyl radicals to form together with the nitrogen atom to which they are bonded a 5- to 8-membered heterocyclyl. With regard to heterocyclyl it is referred to the definition said term. Preferred heterocyclyl in this context are morpholinyl and piperidinyl, more preferably morpholinyl.

$C_1$-$C_6$-Alkylcarbonylamino is an alkylcarbonyl radical linked via an amino group, where the alkyl radical may be straight-chain or branched and comprises 1 to 6, preferably 1 to 4 and particularly preferably 1 to 3, carbon atoms. Preferred examples include methylcarbonylamino, ethylcarbonylamino, n-propylcarbonylamino, isopropylcarbonylamino, tert-butylcarbonylamino, n-pentylcarbonylamino and n-hexylcarbonylamino.

$C_1$-$C_6$-Alkylsulphonyl: The term $C_1$-$C_6$-alkyl stands for a straight-chain or branched alkyl-group linked via a sulphonyl ($SO_2$) radical to the phenyl or pyridyl. The $C_1$-$C_6$-alkyl having 1 to 6, preferably 1 to 4 and particularly preferably having 1 to 3, carbon atoms. Preferred examples include methylsulphonyl, ethylsulphonyl, n-propylsulphonyl, isopropylsulphonyl, tert-butylsulphonyl, n-pentylsulphonyl and n-hexylsulphonyl.

$C_1$-$C_6$-Alkylsulphonylamino is a $C_1$-$C_6$-Alkylsulphonyl linked via an Aminogroup to the phenyl or pyridyl. For $C_1$-$C_6$-Alkylsulphonyl see the corresponding definition. Preferred examples include methylsulphonylamino, ethylsulphonylamino, n-propylsulphonylamino, isopropyl-sulphonylamino, tert-butylsulphonylamino, n-pentylsulphonylamino and n-hexylsulphonylamino.

$C_1$-$C_6$-Alkylthio: The term $C_1$-$C_6$-alkyl stands for a straight-chain or branched alkyl-group linked via a sulphur (—S—) radical to the phenyl or pyridyl. The $C_1$-$C_6$-alkyl group having 1 to 6, preferably 1 to 4 and particularly preferably having 1 to 3, carbon atoms. Preferred examples include methylthio, ethylthio, n-propylthio, isopropylthio, tert-butylthio, n-pentylthio and n-hexylthio.

$C_6$-$C_{10}$-Arylaminocarbonyl is an arylamino radical linked via a carbonyl group. Preferred examples include phenylaminocarbonyl and naphthylaminocarbonyl.

$C_6$-$C_{10}$-Arylcarbonylamino is an arylcarbonyl radical linked via an amino group. Preferred examples include phenylcarbonylamino and naphthylcarbonylamino.

Halogen is fluorine, chlorine, bromine and iodine. Fluorine, chlorine, bromine are preferred, and fluorine and chlorine are particularly preferred.

Heteroaryl is an aromatic, mono- or bicyclic radical having 5 to 10 ring atoms and up to 5 heteroatoms from the series S, O and/or N. 5- to 6-membered heteroaryls having up to 4 heteroatoms are preferred. The heteroaryl radical may be bonded via a carbon or nitrogen atom. Preferred examples include thienyl, furyl, pyrrolyl, thiazolyl, oxazolyl, imidazolyl, tetrazolyl, pyridyl, pyrimidinyl, pyridazinyl, indolyl, indazolyl, benzofuranyl, benzothiophenyl, quinolinyl and isoquinolinyl.

6-membered heteroaryl is an aromatic radical having 6 ring atoms and up to 2 nitrogen atoms. The heteroaryl radical is bonded via a carbon atom. Preferred examples include pyridyl, pyrimidinyl, pyridazinyl and pyrazinyl.

Heteroarylaminocarbonyl is a heteroarylamino radical linked via a carbonyl group. For heteroaryl see the corresponding definition. Preferred examples include thienylaminocarbonyl, furylaminocarbonyl, pyrrolylaminocarbonyl, thiazolylaminocarbonyl, oxazolylaminocarbonyl, imidazolylaminocarbonyl, tetrazolylaminocarbonyl, pyridylaminocarbonyl, pyrimidinylaminocarbonyl, pyridazinylaminocarbonyl, indolylaminocarbonyl, indazolylaminocarbonyl, benzofuranylaminocarbonyl, benzothiophenylaminocarbonyl, quinolinylaminocarbonyl and isoquinolinylaminocarbonyl.

Heteroarylcarbonylamino is a heteroarylcarbonyl radical linked via an amino group. For heteroaryl see the corresponding definition. Preferred examples include thienylcarbonylamino, furylcarbonylamino, pyrrolylcarbonylamino, thiazolylcarbonylamino, oxazolylcarbonylamino, imidazolylcarbonylamino, tetrazolylcarbonylamino, pyridylcarbonylamino, pyrimidinylcarbonylamino, pyridazinylcarbonylamino, indolylcarbonylamino, indazolylcarbonylamino, benzofuranylcarbonylamino, benzothiophenylcarbonylamino, quinolinylcarbonylamino and isoquinolinylcarbonylamino.

5- to 8-membered heterocyclyl is a mono- or polycyclic heterocyclic radical having 5 to 8 ring atoms and up to 3, preferably 2, heteroatoms or hetero groups from the series N, O, S, SO, $SO_2$. Mono- or bicyclic heterocyclyl is preferred. Monocyclic heterocyclyl is particularly preferred. N and O are preferred as heteroatoms. The heterocyclyl radicals may be saturated or partially unsaturated. Saturated heterocyclyl radicals are preferred. 5- to 7-membered heterocyclyl radicals are particularly preferred. Preferred examples include oxetan-3-yl, pyrrolidin-2-yl, pyrrolidin-3-yl, pyrrolinyl, tetrahydrofuranyl, tetrahydrothienyl, pyranyl, piperidinyl, thiopyranyl, morpholinyl, perhydroazepinyl. More preferred is morpholinyl.

When radicals in the compounds of the invention are optionally substituted, unless otherwise specified substitution by up to three identical or different substituents is preferred.

The term "compound" is understood in the chemical meaning as understood by the scientific chemical community.

It will be evident for the person skilled in the art, that some of the embodiments of the compounds of the invention may appear in tautomeric form(s) or stereoisomeric form(s) (enantiomers, diastereomers, racemates, mixtures thereof, etc.), which for example may exist in dependency of the substitution pattern. A stereochemically pure constituent can be isolated in a known manner from such mixtures of enantiomers and/or diastereomers.

Some embodiments of the compounds of the invention also may be transferred into physiologically acceptable salts.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

Such physiologically acceptable salts of the compounds of the present invention include salts with mineral acids, carboxylic acids and sulphonic acids, e.g. salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, malic acid, citric acid, fumaric acid, maleic acid and benzoic acid, e.g. in the form of acid addition salts.

Physiologically acceptable salts of such embodiments of the present invention also may include salts with conventional bases such as, by way of example and preferably, alkali metal salts (e.g. sodium and potassium salts), alkaline earth metal salts (e.g. calcium and magnesium salts) and ammonia, organic amines having 1 to 16 C atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, dehydroabietylamine, arginine, lysine, ethylenediamine and methylpiperidine.

Some embodiments of compounds of the present invention may form solvates. For the purposes of the invention the term "solvates" refers to those forms of the compounds which form, in the solid or liquid state, a complex with solvent molecules. Hydrates are a specific form of solvates in which the coordination takes place with water. Typically a solvate is a crystalline complex of host molecules (compound molecules) and solvent molecules. The molecules of the solvent are incorporated into the host lattice. The solvent molecules may—but need not—be linked to the host molecule by coordination. Solvates also may be formed by salt forms of the compounds of the present invention. Most interesting pharmaceutically acceptable solvates include hydrates or solvates with ethanol.

A derivative of a compound according to the invention which shares the same pharmacophoric group or groups and which thus provides a bioequivalent pharmacological effect may be considered a subgeneric form of said compound according to the invention.

The compounds of the present invention may be made in accordance with the outline of WO04099210 (in particular page 9, last paragraph to page 14, line 8, incorporated by reference). Specific procedures can be taken from the experimental part thereof.

A specific and independent embodiment EA according to the present invention refers to a compound, characterised by general formula I:

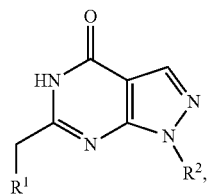

(I)

with
$R^1$
being phenyl or pyridyl, any of which is substituted with 1 to 4, preferably 1 to 3 substituents X;
and with the option that each of phenyl or pyridyl in addition may be substituted by up to 3 radicals independently of one another selected from the group of $C_1$-$C_6$-alkyl, $C_1$-$C_6$-alkoxy, hydroxycarbonyl, cyano, trifluoromethyl, amino, nitro, hydroxy, $C_1$-$C_6$-alkylamino, halogen, $C_6$-$C_{10}$-arylcarbonylamino, $C_1$-$C_6$-alkylcarbonylamino, $C_1$-$C_6$-alkylaminocarbonyl, $C_1$-$C_6$-alkoxycarbonyl, $C_6$-$C_{10}$-arylaminocarbonyl, heteroarylaminocarbonyl, heteroarylcarbonylamino, $C_1$-$C_6$-alkylsulphonylamino, $C_1$-$C_6$-alkylsulphonyl, $C_1$-$C_6$-alkylthio,
where each of $C_1$-$C_6$-alkyl, $C_1$-$C_6$-alkoxy, $C_1$-$C_6$-alkylamino, $C_6$-$C_{10}$-arylcarbonylamino, $C_1$-$C_6$-alkylcarbonylamino, $C_1$-$C_6$-alkylaminocarbonyl, $C_1$-$C_6$-alkoxycarbonyl, $C_6$-$C_{10}$-arylaminocarbonyl, heteroarylaminocarbonyl, heteroarylcarbonylamino, $C_1$-$C_6$-alkylsulphonylamino, $C_1$-$C_6$-alkylsulphonyl and $C_1$-$C_6$-alkylthio are optionally substituted by 1 to 3 radicals independently of one another selected from the group of hydroxy, cyano, halogen, hydroxycarbonyl and a group of the formula —$NR^3R^4$,
X
independently of each other being selected from $C_2$-$C_6$-alkyl or $C_1$-$C_6$-alkoxy, where $C_2$-$C_6$-alkyl and $C_1$-$C_6$-alkoxy are at least dihalogenated up to perhalogenated and the halogen atoms being selected from the group of fluoro, chloro and bromo, preferably fluoro, whereby at least the C-atom which constitutes the beta position with respect to the link to the phenyl or pyridyl is at least one fold or more preferably at least twofold halogenated;
$R^2$
being phenyl or heteroaryl, where phenyl is substituted by 1 to 3 radicals and heteroaryl is optionally substituted by 1 to 3 radicals in each case independently of one another selected from the group of $C_1$-$C_6$-alkyl, $C_1$-$C_6$-alkoxy, hydroxycarbonyl, cyano, trifluoromethyl, amino, nitro, hydroxy, $C_1$-$C_6$-alkylamino, halogen, $C_6$-$C_{10}$-arylcarbonylamino, $C_1$-$C_6$-alkylcarbonylamino, $C_1$-$C_6$-alkylaminocarbonyl, $C_1$-$C_6$-alkoxycarbonyl, $C_6$-$C_{10}$-arylaminocarbonyl, heteroarylaminocarbonyl, heteroarylcarbonylamino, $C_1$-$C_6$-alkylsulphonylamino, $C_1$-$C_6$-alkylsulphonyl and $C_1$-$C_6$-alkylthio,
where each of $C_1$-$C_6$-alkyl, $C_1$-$C_6$-alkoxy, $C_1$-$C_6$-alkylamino, $C_6$-$C_{10}$-arylcarbonylamino, $C_1$-$C_6$-alkylcarbonylamino, $C_1$-$C_6$-alkylaminocarbonyl, $C_1$-$C_6$-alkoxycarbonyl, $C_6$-$C_{10}$-arylaminocarbonyl, heteroarylaminocarbonyl, heteroarylcarbonylamino, $C_1$-$C_6$-alkylsulphonylamino, $C_1$-$C_6$-alkylsulphonyl and $C_1$-$C_6$-alkylthio are optionally substituted by one to three radicals independently of one another selected from the group of hydroxy, cyano, halogen, hydroxycarbonyl and a group of the formula —$NR^3R^4$,
$R^3$
being hydrogen or $C_1$-$C_6$-alkyl,
and $R^4$
being hydrogen or $C_1$-$C_6$-alkyl,
or $R^3$ and $R^4$ together with the nitrogen atom to which they are bonded are 5- to 8-membered heterocyclyl
and/or pharmaceutically acceptable salts thereof and/or solvates thereof.

Yet a specific and independent embodiment EB according to the present invention refers to a compound characterised by general formula I:

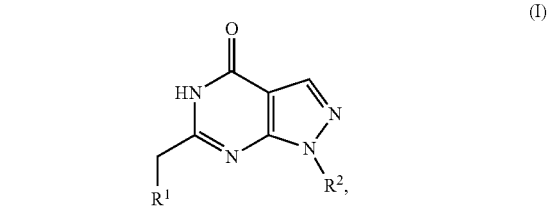

(I)

with
$R^1$
being phenyl or pyridyl, any of which is substituted with 1 to 3 substituents X;
and with the option that each of phenyl or pyridyl in addition may be substituted by up to 3 radicals independently of one another selected from the group of $C_1$-$C_6$-alkyl, $C_1$-$C_6$-alkoxy, cyano, trifluoromethyl, nitro, halogen, $C_6$-$C_{10}$-arylcarbonylamino, $C_1$-$C_6$-alkylcarbonylamino, $C_1$-$C_6$-alkylaminocarbonyl, $C_6$-$C_{10}$-arylaminocarbonyl, heteroarylaminocarbonyl, heteroarylcarbonylamino, $C_1$-$C_6$-alkylsulphonylamino, $C_1$-$C_6$-alkylsulphonyl, $C_1$-$C_6$-alkylthio,
where each of $C_1$-$C_6$-alkyl, $C_1$-$C_6$-alkoxy, $C_6$-$C_{10}$-arylcarbonylamino, $C_1$-$C_6$-alkylcarbonylamino, $C_1$-$C_6$-alkylaminocarbonyl, $C_6$-$C_{10}$-arylaminocarbonyl, heteroarylaminocarbonyl, heteroarylcarbonylamino, $C_1$-$C_6$-alkylsulphonylamino, $C_1$-$C_6$-alkylsulphonyl and $C_1$-$C_6$-alkylthio are optionally substituted by one to three radicals independently of one another selected from the group of hydroxy, cyano, halogen, and a group of the formula —$NR^3R^4$,
X
independently of each other being selected from $C_2$-$C_6$-alkyl or $C_1$-$C_6$-alkoxy, where $C_2$-$C_6$-alkyl and $C_1$-$C_6$-alkoxy are at least dihalogenated up to perhalogenated and the halogen atoms being selected from the group of fluoro, chloro and bromo, preferably fluoro, whereby at least the C-atom which constitutes the beta position with respect to the link to the phenyl or pyridyl is at least one fold or more preferably at least twofold halogenated;

R²
being phenyl or heteroaryl, where phenyl is substituted by 1 to 3 radicals and heteroaryl is optionally substituted by 1 to 3 radicals in each case independently of one another selected from the group of $C_1$-$C_6$-alkyl, $C_1$-$C_6$-alkoxy, hydroxycarbonyl, cyano, trifluoromethyl, amino, nitro, hydroxy, $C_1$-$C_6$-alkylamino, halogen, $C_1$-$C_6$-alkylcarbonylamino, $C_1$-$C_6$-alkylaminocarbonyl, $C_1$-$C_6$-alkylsulphonylamino, $C_1$-$C_6$-alkylsulphonyl and $C_1$-$C_6$-alkylthio, where each of $C_1$-$C_6$-alkyl, $C_1$-$C_6$-alkoxy, $C_1$-$C_6$-alkylamino, $C_6$-$C_{10}$-arylcarbonylamino, $C_1$-$C_6$-alkylcarbonylamino, $C_1$-$C_6$-alkylaminocarbonyl, $C_1$-$C_6$-alkylsulphonylamino, $C_1$-$C_6$-alkylsulphonyl and $C_1$-$C_6$-alkylthio are optionally substituted by one to three radicals independently of one another selected from the group of hydroxy, cyano, halogen, and a group of the formula —$NR^3R^4$, and the remaining characteristics as defined for embodiment EA and/or pharmaceutically acceptable salts thereof and/or solvates thereof.

Yet a specific and independent embodiment EC according to the present invention refers to a compound characterised by general formula I:

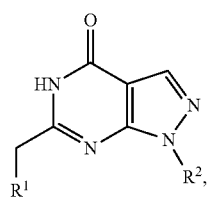

with
R¹
being phenyl or pyridyl, any of which is substituted with one to three substituents X;
and with the option that each of phenyl or pyridyl in addition may be substituted by up to 3 radicals independently of one another selected from the group of $C_1$-$C_6$-alkyl, trifluoromethyl, halogen, X
independently of each other being selected from $C_2$-$C_6$-alkyl or $C_1$-$C_6$-alkoxy, where $C_2$-$C_6$-alkyl and $C_1$-$C_6$-alkoxy are at least dihalogenated up to perhalogenated and the halogen atoms being selected from the group of fluoro, chloro and bromo, preferably fluoro, whereby at least the C-atom which constitutes the beta position with respect to the link to the phenyl or pyridyl is a least one fold or more preferably at least twofold halogenated;

R²
being phenyl or pyridyl, where phenyl is substituted by 1 to 3 radicals and heteroaryl is optionally substituted by 1 to 3 radicals in each case independently of one another selected from the group of $C_1$-$C_6$-alkyl, $C_1$-$C_6$-alkoxy, trifluoromethyl, halogen and $C_1$-$C_6$-alkylthio,
where each of $C_1$-$C_6$-alkyl, $C_1$-$C_6$-alkoxy and $C_1$-$C_6$-alkylthio, are optionally substituted by one to three halogen radicals,
and the remaining characteristics as defined for embodiment EA and/or pharmaceutically acceptable salts thereof and/or solvates thereof.

Yet a specific and independent embodiment ED according to the present invention refers to a compound characterised by general formula I:

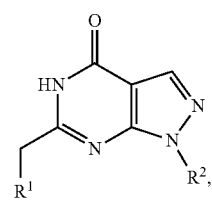

with
R¹ being phenyl or pyridyl any of which being substituted with 1 to 3X whereas X being $C_2$-$C_6$-alkyl, preferably $C_2$-alkyl, with the further optional substitution pattern for $C_2$-$C_6$-alkyl and/or phenyl or $C_2$-$C_6$-alkyl and/or pyridyl and the remaining features as defined in any of the embodiments EA, EB or EC and/or pharmaceutically acceptable salts thereof and/or solvates thereof.

Yet a specific and independent embodiment EE according to the present invention refers to a compound characterised by general formula I:

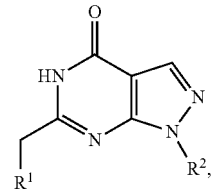

with
R¹ being phenyl or pyridyl, any of which being substituted with 1 to 3X, whereas X being $C_1$-$C_6$-alkoxy, preferably $C_1$-alkoxy with the further optional substitution pattern for $C_1$-$C_6$-alkoxy and/or phenyl or $C_1$-$C_6$-alkoxy and/or pyridyl and the remaining features as defined for any of embodiments EA or EB and/or pharmaceutically acceptable salts thereof and/or solvates thereof.

Yet a specific and independent embodiment EF according to the present invention refers to a compound characterised by general formula I:

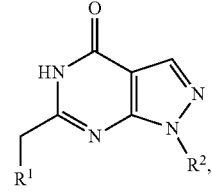

with
R¹
being phenyl or pyridyl, any of which must be substituted with 1 to 3X, whereas X being $C_1$-$C_6$-alkoxy, substituted by at least 2, preferably 2 to 6 halogen atoms, selected from the group of fluoro, chloro and bromo, preferably fluoro substitutents, whereby preferably at least the C-atom which constitutes the beta position with respect to the link to the phenyl or pyridyl is at least one fold or more preferred at least twofold halogenated;
and with the option that each of phenyl or pyridyl in addition may be substituted by up to 3 radicals independently of one another selected from the group of $C_1$-$C_6$-alkyl, trifluoromethyl, halogen,
and the remaining characteristics as defined in claim EA, EB, EC or EE and/or pharmaceutically acceptable salts thereof and/or solvates thereof.

Yet a specific and independent embodiment EG according to the present invention refers to a compound characterised by general formula I:

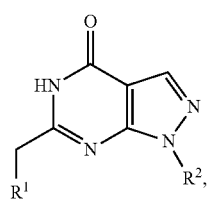
(I)

with
$R^1$ and $R^2$ as defined for any of the aforementioned embodiments EA, EB, EC, ED, EE or EF and for $R^1$ the substitution pattern at the one to 3 mandatory substituents X are at least 2, more preferably 3 fluoro substituents, whereby preferably at least the C-atom which constitutes the beta position with respect to the link to the phenyl or pyridyl is at least one fold or more preferred at least twofold halogenated and/or pharmaceutically acceptable salts thereof and/or solvates thereof.

Yet a specific and independent embodiment EH according to the present invention refers to a compound characterised by general formula I:

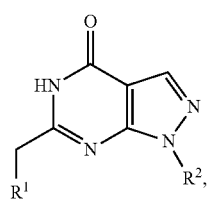
(I)

with
$R^1$ and $R^2$ as defined for any of the aforementioned embodiments EA, EB, EC, ED, EE, EF or EG with $R^1$ being phenyl substituted as defined in any of embodiments 1 to 5, preferably 2-trifluoromethoxyphenyl and/or pharmaceutically acceptable salts thereof and/or solvates thereof.

Preferred embodiments of the present invention are the following compounds, whereby each single compound is considered a specific and independent aspect of the present invention:

| Compund | Structure | Name |
|---|---|---|
| 1 | 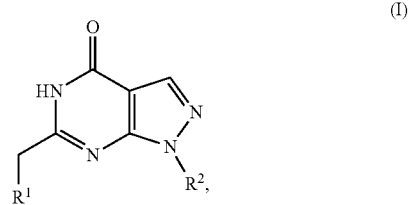 | 1-(4-Methyl-pyridin-3-yl)-6-(2-trifluoromethoxy-benzyl)-1,5-dihydro-pyrazolo[3,4-d]pyrimidin-4-one |
| 2 | 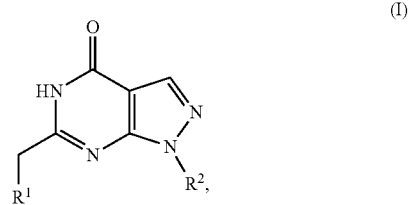 | 1-o-Tolyl-6-(2-trifluoromethoxy-benzyl)-1,5-dihydro-pyrazolo[3,4-d]pyrimidin-4-one |

-continued

| Compund | Structure | Name |
|---|---|---|
| 3 | 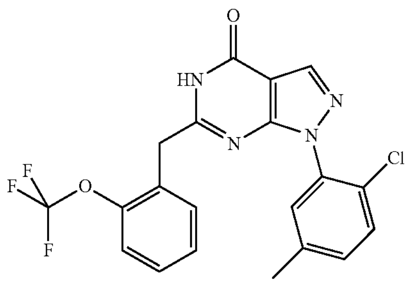 [SMILES: Cc1ccc(Cl)c(-n2ncc3c(=O)[nH]c(Cc4ccccc4OC(F)(F)F)nc32)c1] | 1-(2-Chloro-5-methyl-phenyl)-6-(2-trifluoromethoxy-benzyl)-1,5-dihydro-pyrazolo[3,4-d]pyrimidin-4-one |
| 4 | 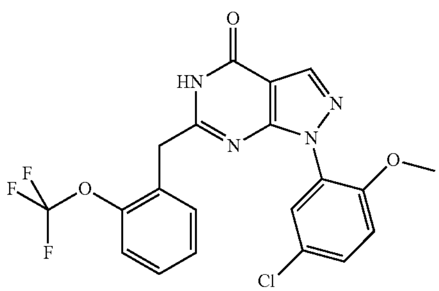 [SMILES: COc1ccc(Cl)cc1-n1ncc2c(=O)[nH]c(Cc3ccccc3OC(F)(F)F)nc21] | 1-(5-Chloro-2-methoxy-phenyl)-6-(2-trifluoromethoxy-benzyl)-1,5-dihydro-pyrazolo[3,4-d]pyrimidin-4-one |
| 5 | 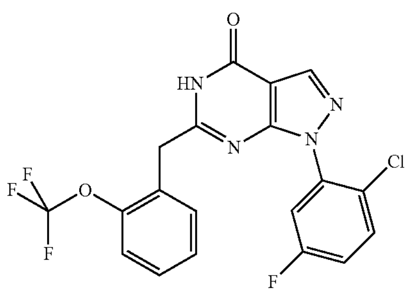 [SMILES: O=c1[nH]c(Cc2ccccc2OC(F)(F)F)nc2c1cnn2-c1cc(F)ccc1Cl] | 1-(2-Chloro-5-fluoro-phenyl)-6-(2-trifluoromethoxy-benzyl)-1,5-dihydro-pyrazolo[3,4-d]pyrimidin-4-one |
| 6 | 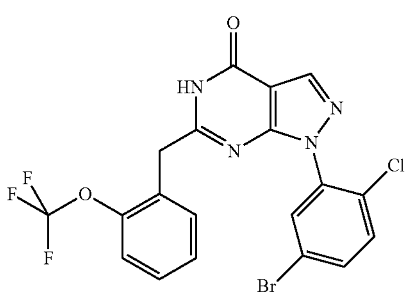 [SMILES: O=c1[nH]c(Cc2ccccc2OC(F)(F)F)nc2c1cnn2-c1cc(Br)ccc1Cl] | 1-(5-Bromo-2-chloro-phenyl)-6-(2-trifluoromethoxy-benzyl)-1,5-dihydro-pyrazolo[3,4-d]pyrimidin-4-one |
| 7 | 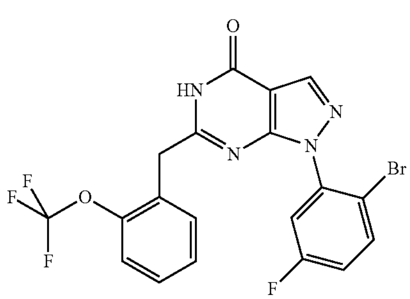 | 1-(2-Bromo-5-fluoro-phenyl)-6-(2-trifluoromethoxy-benzyl)-1,5-dihydro-pyrazolo[3,4-d]pyrimidin-4-one |

| Compund | Structure | Name |
|---|---|---|
| 8 | 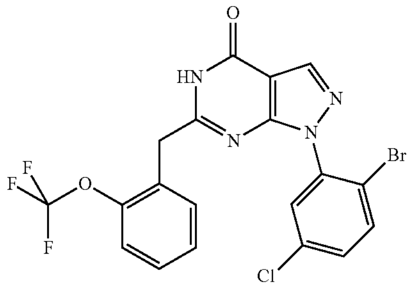 [SMILES: O=c1[nH]c(Cc2ccccc2OC(F)(F)F)nc2c1cnn2-c1cc(Cl)ccc1Br] | 1-(2-Bromo-5-chloro-phenyl)-6-(2-trifluoromethoxy-benzyl)-1,5-dihydro-pyrazolo[3,4-d]pyrimidin-4-one |
| 9 | 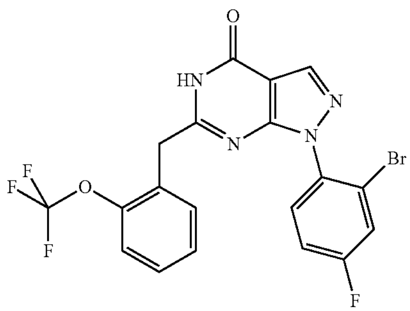 [SMILES: O=c1[nH]c(Cc2ccccc2OC(F)(F)F)nc2c1cnn2-c1ccc(F)cc1Br] | 1-(2-Bromo-4-fluoro-phenyl)-6-(2-trifluoromethoxy-benzyl)-1,5-dihydro-pyrazolo[3,4-d]pyrimidin-4-one |
| 10 | 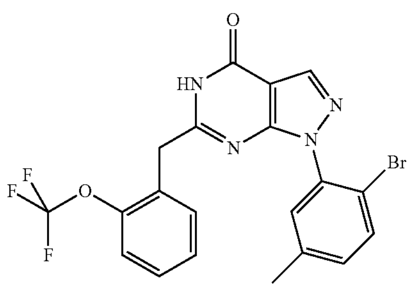 | 1-(2-Bromo-5-methyl-phenyl)-6-(2-trifluoromethoxy-benzyl)-1,5-dihydro-pyrazolo[3,4-d]pyrimidin-4-one |
| 11 | 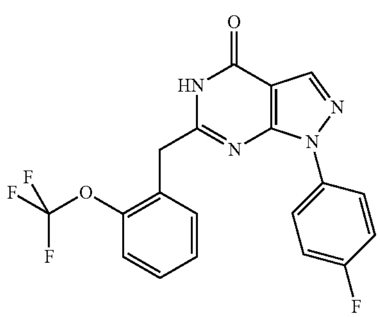 | 1-(4-Fluoro-phenyl)-6-(2-trifluoromethoxy-benzyl)-1,5-dihydro-pyrazolo[3,4-d]pyrimidin-4-one |
| 12 | 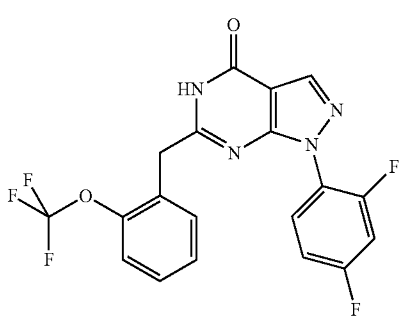 [SMILES: O=c1[nH]c(Cc2ccccc2OC(F)(F)F)nc2c1cnn2-c1ccc(F)cc1F] | 1-(2,4-Difluoro-phenyl)-6-(2-trifluoromethoxy-benzyl)-1,5-dihydro-pyrazolo[3,4-d]pyrimidin-4-one |

-continued

| Compund | Structure | Name |
|---|---|---|
| 13 | 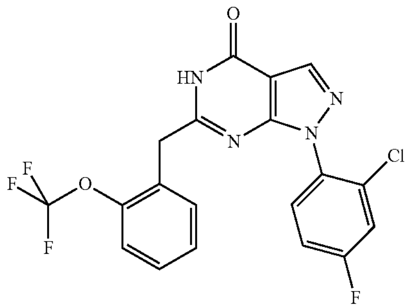 [SMILES: O=c1[nH]c(Cc2ccccc2OC(F)(F)F)nc2c1cnn2-c1ccc(F)cc1Cl] | 1-(2-Chloro-4-fluoro-phenyl)-6-(2-trifluoromethoxy-benzyl)-1,5-dihydro-pyrazolo[3,4-d]pyrimidin-4-one |
| 14 | 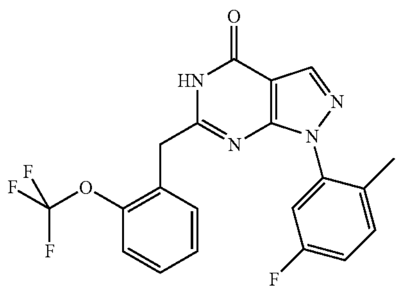 | 1-(5-Fluoro-2-methyl-phenyl)-6-(2-trifluoromethoxy-benzyl)-1,5-dihydro-pyrazolo[3,4-d]pyrimidin-4-one |
| 15 | 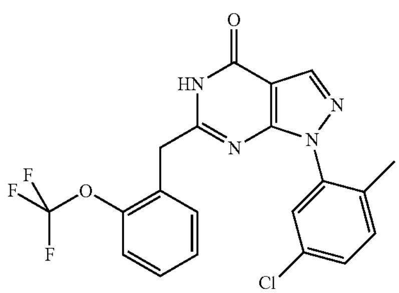 | 1-(5-Chloro-2-methyl-phenyl)-6-(2-trifluoromethoxy-benzyl)-1,5-dihydro-pyrazolo[3,4-d]pyrimidin-4-one |
| 16 | 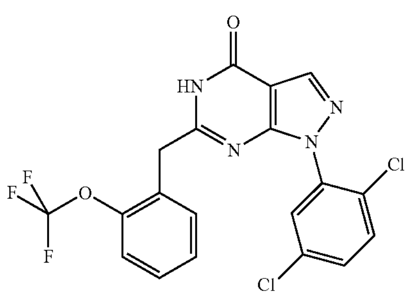 [SMILES: O=c1[nH]c(Cc2ccccc2OC(F)(F)F)nc2c1cnn2-c1cc(Cl)ccc1Cl] | 1-(2,5-Dichloro-phenyl)-6-(2-trifluoromethoxy-benzyl)-1,5-dihydro-pyrazolo[3,4-d]pyrimidin-4-one |
| 17 | 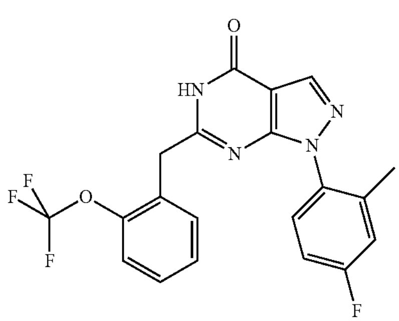 [SMILES: Cc1cc(F)ccc1-n1ncc2c(=O)[nH]c(Cc3ccccc3OC(F)(F)F)nc21] | 1-(4-Fluoro-2-methyl-phenyl)-6-(2-trifluoromethoxy-benzyl)-1,5-dihydro-pyrazolo[3,4-d]pyrimidin-4-one |

| Compund | Structure | Name |
|---|---|---|
| 18 | 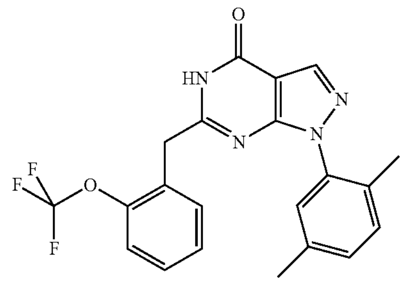 [SMILES: Cc1ccc(C)c(-n2ncc3c(=O)[nH]c(Cc4ccccc4OC(F)(F)F)nc32)c1] | 1-(2,5-Dimethyl-phenyl)-6-(2-trifluoromethoxy-benzyl)-1,5-ihydro-pyrazolo[3,4-d]pyrimidin-4-one |
| 19 | 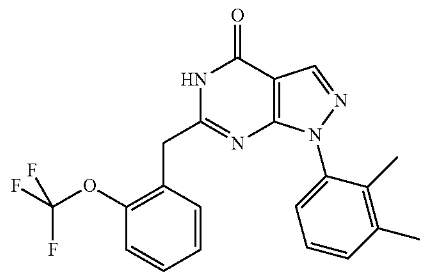 [SMILES: Cc1cccc(-n2ncc3c(=O)[nH]c(Cc4ccccc4OC(F)(F)F)nc32)c1C] | 1-(2,3-Dimethyl-phenyl)-6-(2-trifluoromethoxy-benzyl)-1,5-dihydro-pyrazolo[3,4-d]pyrimidin-4-one |
| 20 | 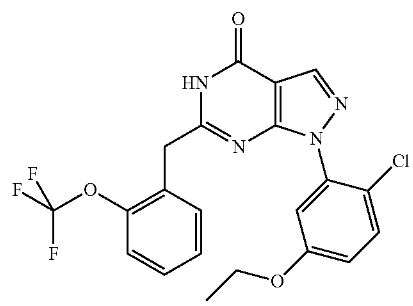 [SMILES: CCOc1ccc(Cl)c(-n2ncc3c(=O)[nH]c(Cc4ccccc4OC(F)(F)F)nc32)c1] | 1-(2-Chloro-5-ethoxy-phenyl)-6-(2-trifluoromethoxy-benzyl)-1,5-dihydro-pyrazolo[3,4-d]pyrimidin-4-one |
| 21 | 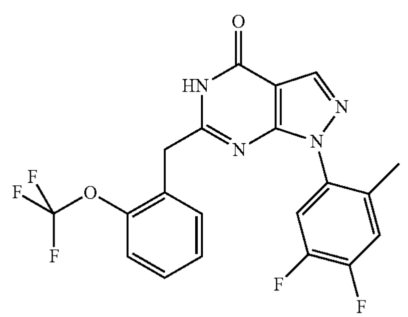 [SMILES: Cc1cc(F)c(F)cc1-n1ncc2c(=O)[nH]c(Cc3ccccc3OC(F)(F)F)nc21] | 1-(4,5-Difluoro-2-methyl-phenyl)-6-(2-trifluoromethoxy-benzyl)-1,5-dihydro-pyrazolo[3,4-d]pyrimidin-4-one |
| 22 | 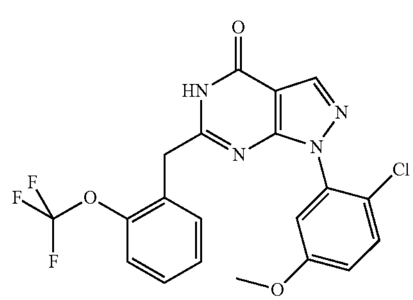 [SMILES: COc1ccc(Cl)c(-n2ncc3c(=O)[nH]c(Cc4ccccc4OC(F)(F)F)nc32)c1] | 1-(2-Chloro-5-methoxy-phenyl)-6-(2-trifluoromethoxy-benzyl)-1,5-dihydro-pyrazolo[3,4-d]pyrimidin-4-one |

-continued

| Compund | Structure | Name |
|---|---|---|
| 23 | 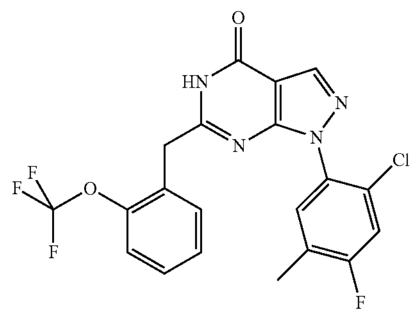 [SMILES: Cc1cc(-n2ncc3c(=O)[nH]c(Cc4ccccc4OC(F)(F)F)nc32)c(Cl)cc1F] | 1-(2-Chloro-4-fluoro-5-methyl-phenyl)-6-(2-trifluoromethoxy-benzyl)-1,5-dihydro-pyrazolo[3,4-d]pyrimidin-4-one |
| 24 | 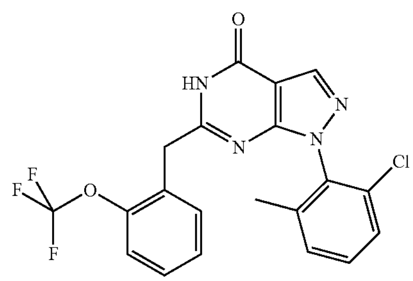 [SMILES: Cc1cccc(Cl)c1-n1ncc2c(=O)[nH]c(Cc3ccccc3OC(F)(F)F)nc21] | 1-(2-Chloro-6-methyl-phenyl)-6-(2-trifluoromethoxy-benzyl)-1,5-dihydro-pyrazolo[3,4-d]pyrimidin-4-one |
| 25 | 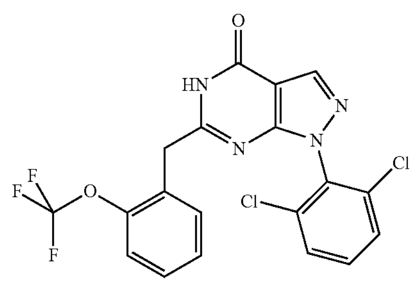 [SMILES: O=c1[nH]c(Cc2ccccc2OC(F)(F)F)nc2c1cnn2-c1c(Cl)cccc1Cl] | 1-(2,6-Dichloro-phenyl)-6-(2-trifluoromethoxy-benzyl)-1,5-dihydro-pyrazolo[3,4-d]pyrimidin-4-one |
| 26 | 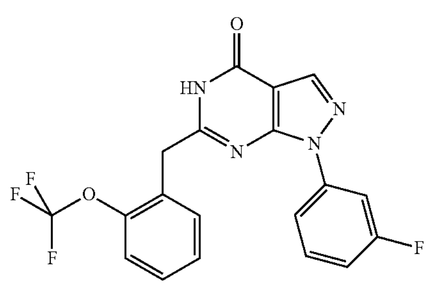 [SMILES: O=c1[nH]c(Cc2ccccc2OC(F)(F)F)nc2c1cnn2-c1cccc(F)c1] | 1-(3-Fluoro-phenyl)-6-(2-trifluoromethoxy-benzyl)-1,5-dihydro-pyrazolo[3,4-d]pyrimidin-4-one |
| 27 | 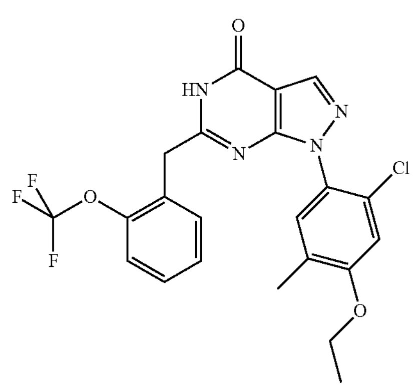 [SMILES: CCOc1cc(Cl)c(-n2ncc3c(=O)[nH]c(Cc4ccccc4OC(F)(F)F)nc32)cc1C] | 1-(2-Chloro-4-ethoxy-5-methyl-phenyl)-6-(2-trifluoromethoxy-benzyl)-1,5-dihydro-pyrazolo[3,4-d]pyrimidin-4-one |

| Compund | Structure | Name |
|---|---|---|
| 28 | 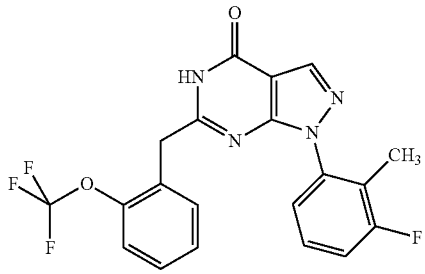 [SMILES: Cc1c(F)cccc1-n1ncc2c(=O)[nH]c(Cc3ccccc3OC(F)(F)F)nc21] | 1-(3-Fluoro-2-methyl-phenyl)-6-(2-trifluoromethoxy-benzyl)-1,5-dihydro-pyrazolo[3,4-d]pyrimidin-4-one |
| 29 | 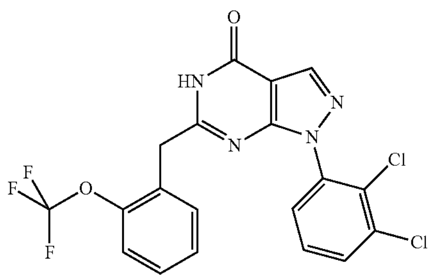 [SMILES: O=c1[nH]c(Cc2ccccc2OC(F)(F)F)nc2c1cnn2-c1cccc(Cl)c1Cl] | 1-(2,3-Dichloro-phenyl)-6-(2-trifluoromethoxy-benzyl)-1,5-dihydro-pyrazolo[3,4-d]pyrimidin-4-one |
| 30 | 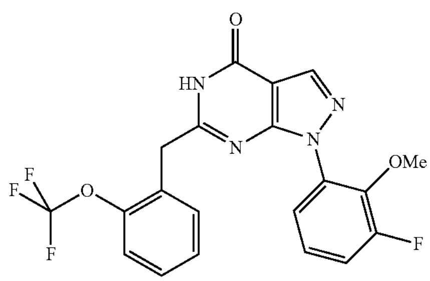 [SMILES: COc1c(F)cccc1-n1ncc2c(=O)[nH]c(Cc3ccccc3OC(F)(F)F)nc21] | 1-(2-Methoxy,3-fluoro-phenyl)-6-(2-trifluoromethoxy-benzyl)-1,5-dihydro-pyrazolo[3,4-d]pyrimidin-4-one |
| 30-1 | 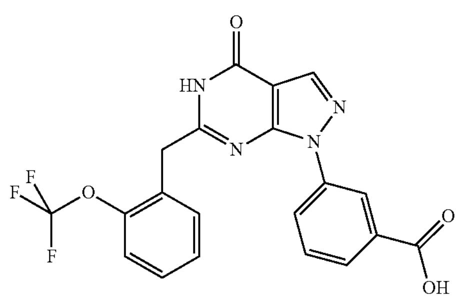 [SMILES: O=C(O)c1cccc(-n2ncc3c(=O)[nH]c(Cc4ccccc4OC(F)(F)F)nc32)c1] | 1-(3-Carbox-phenyl)-6-(2-trifluoromethoxy-benzyl)-1,5-dihydro-pyrazolo[3,4-d]pyrimidin-4-one |
| 30-2 | 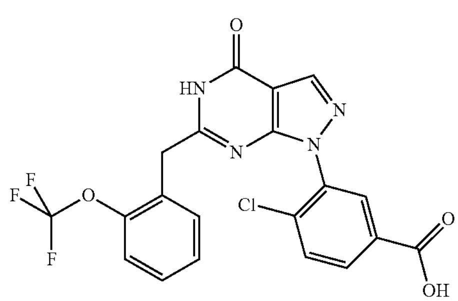 [SMILES: O=C(O)c1ccc(Cl)c(-n2ncc3c(=O)[nH]c(Cc4ccccc4OC(F)(F)F)nc32)c1] | 1-(2-Chloro-5-carbox-phenyl)-6-(2-trifluoromethoxy-benzyl)-1,5-dihydro-pyrazolo[3,4-d]pyrimidin-4-one |

| Compund | Structure | Name |
|---|---|---|
| 30-3 | 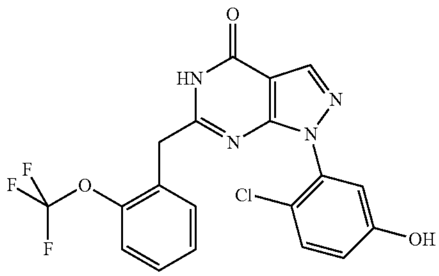 [SMILES: O=c1[nH]c(Cc2ccccc2OC(F)(F)F)nc2c1cnn2-c1cc(O)ccc1Cl] | 1-(2-Chloro-5-hydroxy-phenyl)-6-(2-trifluoromethoxy-benzyl)-1,5-dihydro-pyrazolo[3,4-d]pyrimidin-4-one |
| 30-4 | 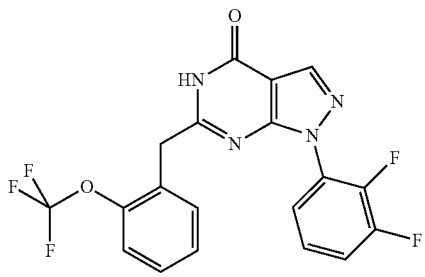 [SMILES: O=c1[nH]c(Cc2ccccc2OC(F)(F)F)nc2c1cnn2-c1cccc(F)c1F] | 1-(2,3-Difluoro-phenyl)-6-(2-trifluoromethoxy-benzyl)-1,5-dihydro-pyrazolo[3,4-d]pyrimidin-4-one |
| 30-5 | 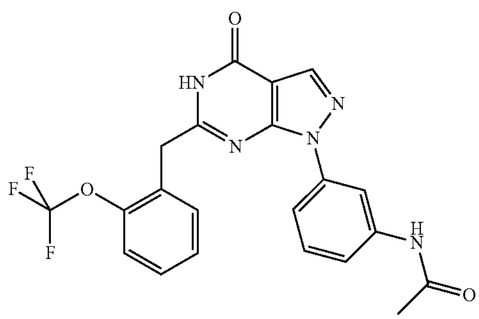 [SMILES: CC(=O)Nc1cccc(-n2ncc3c(=O)[nH]c(Cc4ccccc4OC(F)(F)F)nc32)c1] | 1-(3-Acetamido-phenyl)-6-(2-trifluoromethoxy-benzyl)-1,5-dihydro-pyrazolo[3,4-d]pyrimidin-4-one |
| 31 | 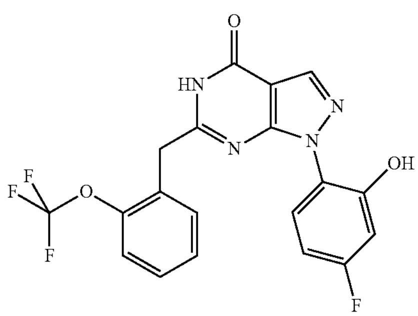 [SMILES: O=c1[nH]c(Cc2ccccc2OC(F)(F)F)nc2c1cnn2-c1ccc(F)cc1O] | 1-(2-Hydroxy,4-fluoro-phenyl)-6-(2-trifluoromethoxy-benzyl)-1,5-dihydro-pyrazolo[3,4-d]pyrimidin-4-one |
| 32 | 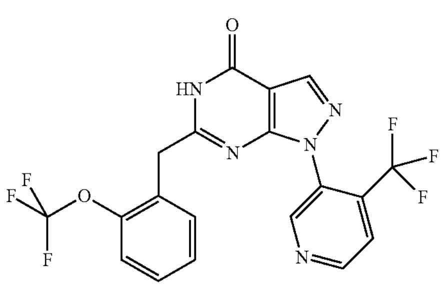 [SMILES: O=c1[nH]c(Cc2ccccc2OC(F)(F)F)nc2c1cnn2-c1cnccc1C(F)(F)F] | 6-(2-Trifluoromethoxy-benzyl)-1-(4-trifluoromethyl-pyridin-3-yl)-1,5-dihydro-pyrazolo[3,4-d]pyrimidin-4-one |

-continued

| Compund | Structure | Name |
|---|---|---|
| 33 | 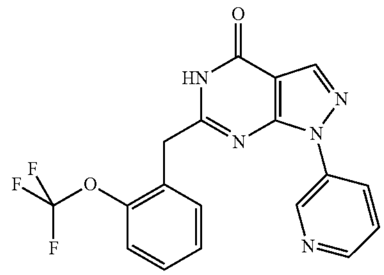 [SMILES: O=c1[nH]c(Cc2ccccc2OC(F)(F)F)nc2c1cnn2-c1cccnc1] | 6-(2-Trifluoromethoxy-benzyl)-1-(pyridin-3-yl)-1,5-dihydro-pyrazolo[3,4-d]pyrimidin-4-one |
| 34 | 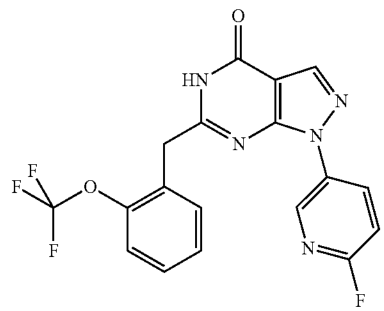 | 6-(2-Trifluoromethoxy-benzyl)-1-(4-fluoro-pyridin-3-yl)-1,5-dihydro-pyrazolo[3,4-d]pyrimidin-4-one |
| 35 | 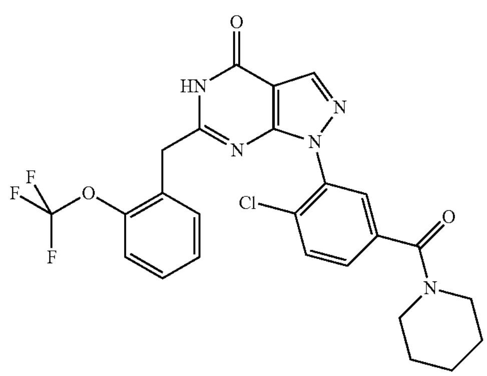 [SMILES: O=C(c1ccc(Cl)c(-n2ncc3c(=O)[nH]c(Cc4ccccc4OC(F)(F)F)nc32)c1)N1CCCCC1] | 1-[2-Chloro-5-(piperidine-1-carbonyl)-phenyl]-6-(2-trifluoromethoxy-benzyl)-1,5-dihydro-pyrazolo[3,4-d]pyrimidin-4-one |
| 36 | 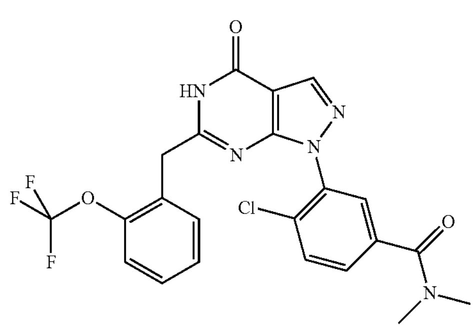 [SMILES: CN(C)C(=O)c1ccc(Cl)c(-n2ncc3c(=O)[nH]c(Cc4ccccc4OC(F)(F)F)nc32)c1] | 1-[2-Chloro-5-(dimethylamino-carbonyl)-phenyl]-6-(2-trifluoromethoxy-benzyl)-1,5-dihydro-pyrazolo[3,4-d]pyrimidin-4-one |

| Compund | Structure | Name |
|---|---|---|
| 37 | | 1-[2-Chloro-5-(N-morpholino-carbonyl)-phenyl]-6-(2-trifluoromethoxy-benzyl)-1,5-dihydro-pyrazolo[3,4-d]pyrimidin-4-one |
| 38 | | 1-[3-(N-morpholino-carbonyl)-phenyl]-6-(2-trifluoromethoxy-benzyl)-1,5-dihydro-pyrazolo[3,4-d]pyrimidin-4-one |
| 39 | | 6-(2-Trifluoromethoxy-benzyl)-1-(3,5-difluoro-pyridin-2-yl)-1,5-dihydro-pyrazolo[3,4-d]pyrimidin-4-one | and/or a pharmaceutically acceptable salt and/or a solvate thereof of each of the compounds where applicable.

Manufacture

The following scheme shall illustrate a process to manufacture the compounds of the present invention by way of example:

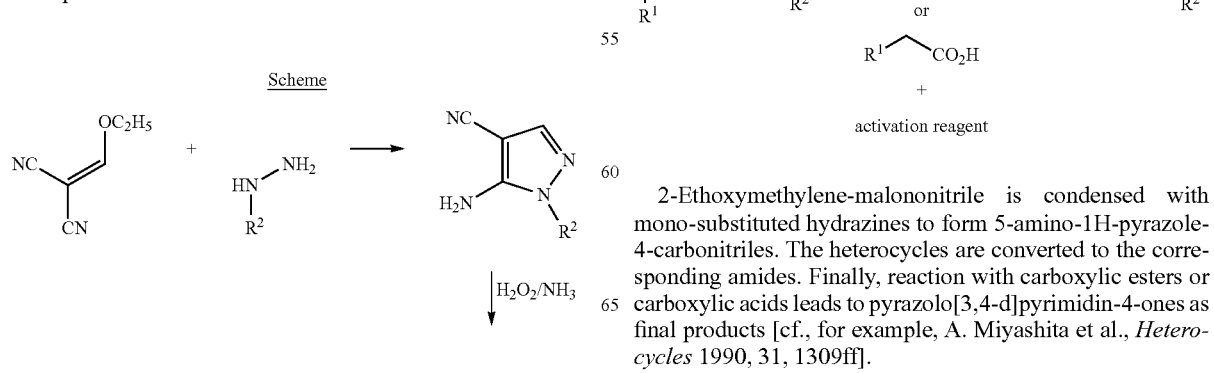

2-Ethoxymethylene-malononitrile is condensed with mono-substituted hydrazines to form 5-amino-1H-pyrazole-4-carbonitriles. The heterocycles are converted to the corresponding amides. Finally, reaction with carboxylic esters or carboxylic acids leads to pyrazolo[3,4-d]pyrimidin-4-ones as final products [cf., for example, A. Miyashita et al., *Heterocycles* 1990, 31, 1309ff].

Mono-substituted hydrazine derivatives can be prepared either by formation of the diazonium salt and consequent reduction or, alternatively, by nucleophilic displacement on the corresponding halide derivative [cf., for example, I. Hunsberger et al., *Journal of Organic Chemistry* 1956, 21, 394-399; T. J. Fleck et al., *Organic Process Research & Development* 2006, 10(2), 334-338].

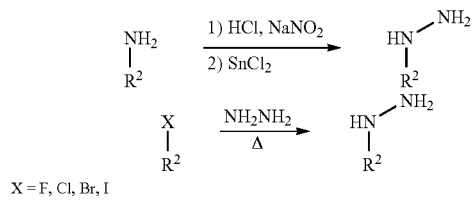

Further processes for preparing pyrazolo[3,4-d]pyrimidin-4-ones are known and can likewise be employed for synthesizing the compounds of the invention (see, for example: P. Schmidt et al., *Helvetica Chimica Acta* 1962, 189, 1620ff.).

Method of Treatment

The compounds of the invention show a valuable range of pharmacological effects which could not have been predicted. They are characterised in particular by inhibition of PDE9A.

In particular the compounds according to the present invention show a good selectivity profile in view of inhibiting or modulating specific members within the PDE9 family or other PDE families, with a preference (selectivity) towards PDE9A inhibition.

To exemplify, but not meant to be limited, it now shall be referred to the selectivity of the PDE 9A inhibiting compounds according the present invention against PDE1C. Bingham et al. (*Biochem. Biophys. Res. Commun.*, 2006, 350, 25-32) described the expression pattern of PDE1C in human tissue. PDE1C shows highest expression in heart tissue followed by testis and vena cava.

Taken together the physiological role of PDE1C and the aspect of the present invention, namely to find compounds that can be used to treat conditions for which the inhibition of PDE9 is considered to be of advantage or that can be taken for the treatment of cognitive impairment, in particular Alzheimer's Disease, it will be appreciated that efficacy weighted against safety appears to be a feature to characterise the compounds of the invention.

It also will be acknowledged that the compounds of the present invention are supposed to show a good safety profile.

As mentioned before, the present invention refers to compounds, which are considered effective and selective inhibitors of phosphodiesterase 9A and can be used for the development of medicaments. Such medicaments shall preferably be used for the treatment of diseases in which the inhibition of PDE9A can evolve a therapeutic, prophylactic or disease modifying effect to the benefit of the patient.

Independently on the mode of action of the compounds, preferably medicaments with a compound according to the invention as active ingredient shall be used to treat, prevent or improve perception, concentration, cognition, learning or memory, like those occurring in particular in situations/diseases/syndromes such as mild cognitive impairment, age-associated learning and memory impairments, age-associated memory losses, vascular dementia, craniocerebral trauma, stroke, dementia occurring after strokes (post stroke dementia), post-traumatic dementia, general concentration impairments, concentration impairments in children with learning and memory problems, Alzheimer's disease, Lewy body dementia, dementia with degeneration of the frontal lobes, including Pick's syndrome, Parkinson's disease, progressive nuclear palsy, dementia with corticobasal degeneration, amyotropic lateral sclerosis (ALS), Huntington's disease, multiple sclerosis, thalamic degeneration, Creutzfeld-Jacob dementia, HIV dementia, schizophrenia with dementia or Korsakoff's psychosis.

Another aspect of the present invention concerns the treatment of sleep disorders like insomnia or narcolepsy, bipolar disorder, metabolic syndrome, obesity, diabetes mellitus, including type 1 or type 2 diabetes, hyperglycemia, dyslipidemia, impaired glucose tolerance, or a disease of the testes, brain, small intestine, skeletal muscle, heart, lung, thymus or spleen or another disease which is accessible by PDE9A modulation.

A preferred condition, the course of which shall be influenced to the benefit of the patient by the use of the compounds according to the present invention is Alzheimer's Disease.

The use of the compounds of the present invention preferably is for the treatment, amelioration and/or prevention of the conditions as outlined herein, preferably for the treatment thereof, more preferably for the symptomatic treatment.

Pharmaceutical Compositions

Medicaments for administration comprise a compound of formula (I) in a therapeutically effective amount. By "therapeutically effective amount" it is meant that if the medicament is applied via the appropriate regimen adapted to the patient's condition, the amount of said compound of formula (I) will be sufficient to effectively treat, to prevent or to decelerate the progression of the corresponding disease, or otherwise to ameliorate the estate of a patient suffering from such a disease. It may be the case that the "therapeutically effective amount" in a mono-therapy will differ from the "therapeutically effective amount" in a combination therapy with another medicament.

The dose range of the compounds of general formula (I) applicable per day is usually from 0.1 to 5000 mg, preferably 0.1 to 1000 mg, preferably from 2 to 500 mg, more preferably from 5 to 250 mg, most preferably from 10 to 100 mg. A dosage unit (e.g. a tablet) preferably contains between 2 and 250 mg, particularly preferably between 10 and 100 mg of the compounds according to the invention.

The actual pharmaceutically effective amount or therapeutic dosage will of course depend on factors known by those skilled in the art such as age, weight, gender or other condition of the patient, route of administration, severity of disease, and the like.

The compounds according to the invention may be administered by oral, parenteral (intravenous, intramuscular etc.), intranasal, sublingual, inhalative, intrathecal, topical or rectal route. Suitable preparations for administering the compounds of formula (I) include for example patches, tablets, capsules, pills, pellets, dragees, powders, troches, suppositories, liquid preparations such as solutions, suspensions, emulsions, drops, syrups, elixirs, or gaseous preparations such as aerosols, sprays and the like. The content of the pharmaceutically active compound(s) should be in the range from 0.05 to 90 wt.-%, preferably 0.1 to 50 wt.-% of the composition as a whole. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions are prepared in the usual way, e.g. with the addition of isotonic agents, preservatives such as p-hydroxybenzoates or stabilisers such as alkali metal salts of ethylenediaminetetraacetic acid, optionally using emulsifiers and/or dispersants, while if water is used as diluent, for example, organic solvents may optionally be used as solubilisers or dissolving aids, and the solutions may be transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral use the tablets may obviously contain, in addition to the carriers specified, additives such as sodium citrate, calcium carbonate and dicalcium phosphate together with various additional substances such as starch, preferably potato starch, gelatin and the like. Lubricants such as magnesium stearate, sodium laurylsulphate and talc may also be used to produce the tablets. In the case of aqueous suspensions the active substances may be combined with various flavour enhancers or colourings in addition to the abovementioned excipients.

The dosage of the compounds according to the invention is naturally highly dependent on the method of administration and the complaint which is being treated. When administered by inhalation the compounds of formula (I) are characterised by a high potency even at doses in the microgram range. The compounds of formula (I) may also be used effectively above the microgram range. The dosage may then be in the gram range, for example.

Combinations with Other Active Substances

In another aspect the present invention relates to the above-mentioned pharmaceutical formulations as such which are characterised in that they contain a compound of formula I.

A further aspect of the present invention refers to a combination of at least one compound according to formula (I) with another compound selected from the group of for example beta-secretase inhibitors; gamma-secretase inhibitors; amyloid aggregation inhibitors such as e.g. alzhemed; directly or indirectly acting neuroprotective and/or disease-modifying substances; anti-oxidants, such as e.g. vitamin E or ginkolide; anti-inflammatory substances, such as e.g. Cox inhibitors, NSAIDs additionally or exclusively having Aβ lowering properties; HMG-CoA reductase inhibitors (statins); acetylcholinesterase inhibitors, such as donepezil, rivastigmine, tacrine, galantamine; NMDA receptor antagonists such as e.g. memantine; AMPA receptor agonists; AMPA receptor positive modulators, AMPkines, monoamine receptor reuptake inhibitors, substances modulating the concentration or release of neurotransmitters; substances inducing the secretion of growth hormone such as ibutamoren mesylate and capromorelin; CB-1 receptor antagonists or inverse agonists; antibiotics such as minocyclin or rifampicin; PDE2, PDE4, PDE5, PDE10 inhibitors, GABAA receptor inverse agonists, GABAA receptor antagonists, nicotinic receptor agonists or partial agonists or positive modulators, alpha4beta2 nicotinic receptor agonists or partial agonists or positive modulators, alpha7 nicotinic receptor agonists or partial agonists or positive modulators; histamine H3 antagonists, 5 HT-4 agonists or partial agonists, 5HT-6 antagonists, alpha2-adrenoreceptor antagonists, calcium antagonists, muscarinic receptor M1 agonists or partial agonists or positive modulators, muscarinic receptor M2 antagonists, muscarinic receptor M4 antagonists, metabotropic glutamate-receptor 5 positive modulators, and other substances that modulate receptors or enzymes in a manner such that the efficacy and/or safety of the compounds according to the invention is increased and/or unwanted side effects are reduced.

This invention further relates to pharmaceutical compositions containing one or more, preferably one active substance, which is selected from the compounds according to the invention and/or the corresponding salts, as well as one or more, preferably one active substance selected from among alzhemed, vitamin E, ginkolide, donepezil, rivastigmine, tacrine, galantamine, memantine, ibutamoren mesylate, capromorelin, minocyclin and/or rifampicin, optionally together with one or more inert carriers and/or diluents.

The compounds according to the invention may also be used in combination with immunotherapies such as e.g. active immunisation with Abeta or parts thereof or passive immunisation with humanised anti-Abeta antibodies or nanobodies for the treatment of the above-mentioned diseases and conditions.

The combinations according to the present invention may be provided simultaneously in one and the same dosage form, i.e. in form of a combination preparation, for example the two components may be incorporated in one tablet, e.g. in different layers of said tablet. The combination may be also provided separately, in form of a free combination, i.e. the compounds of the present invention are provided in one dosage form and one or more of the above mentioned combination partners is provided in another dosage form. These two dosage forms may be equal dosage forms, for example a co-administration of two tablets, one containing a therapeutically effective amount of the compound of the present invention and one containing a therapeutically effective amount of the above mentioned combination partner. It is also possible to combine different administration forms, if desired. Any type of suitable administration forms may be provided.

The compound according to the invention, or a physiologically acceptable salt thereof, in combination with another active substance may be used simultaneously or at staggered times, but particularly close together in time. If administered simultaneously, the two active substances are given to the patient together; if administered at staggered times the two active substances are given to the patient successively within a period of less than or equal to 12, particularly less than or equal to 6 hours.

The dosage or administration forms are not limited, in the frame of the present invention any suitable dosage form may be used. Exemplarily the dosage forms may be selected from solid preparations such as patches, tablets, capsules, pills, pellets, dragees, powders, troches, suppositories, liquid preparations such as solutions, suspensions, emulsions, drops, syrups, elixirs, or gaseous preparations such as aerosols, sprays and the like.

The dosage forms are advantageously formulated in dosage units, each dosage unit being adapted to supply a single dose of each active component being present. Depending from the administration route and dosage form the ingredients are selected accordingly.

The dosage for the above-mentioned combination partners is expediently 1/5 of the normally recommended lowest dose up to 1/1 of the normally recommended dose.

The dosage forms are administered to the patient 1, 2, 3, or 4 times daily. It is preferred that the compounds of the invention be administered either three or fewer times, more preferably once or twice daily.

In accordance with this paragraph, one particular aspect of the invention is a medication consisting of—or the use of—a compound according to the invention, in particular in view of any of the aforementioned embodiments of matrix I, II or III, or any of the embodiments EA, EB, EC, ED, EF, EG, EH or the individually specified compounds, in combination with another therapeutically effective compound, preferably selected from the group of beta-secretase inhibitors; gamma-secretase inhibitors; amyloid aggregation inhibitors; directly or indirectly acting neuroprotective and/or disease-modifying substances; anti-oxidants; anti-inflammatory substances; HMG-CoA reductase inhibitors, statins; acetylcholinesterase inhibitors, NMDA receptor antagonists; AMPA receptor agonists; AMPA receptor positive modulators, AMPkines, monoamine receptor reuptake inhibitors, substances modulating the concentration or release of neurotransmitters; substances modulating the secretion of growth hormone; CB-1 receptor antagonists or inverse agonists; antibiotics; PDE2, PDE4, PDE5, PDE10 inhibitors, GABAA receptor inverse agonists, GABAA receptor antagonists, nicotinic receptor agonists or partial agonists or positive modulators, alpha4beta2 nicotinic receptor agonists or partial agonists or positive modulators, alpha7 nicotinic receptor agonists or partial agonists or positive modulators; histamine H3 antagonists, 5 HT-4 agonists or partial agonists, 5HT-6 antagonists, alpha2-adrenoreceptor antagonists, calcium antagonists, muscarinic receptor M1 agonists or partial agonists or positive modulators, muscarinic receptor M2 antagonists, muscarinic receptor M4 antagonists, metabotropic glutamate-receptor 5 positive modulators, and/or other substances that modulate receptors or enzymes in a manner such that the efficacy and/or safety of the compounds according to the invention is increased and/or unwanted side effects are reduced for the preparation of a medication for the treatment of a disease, in particular as herein described.

EXAMPLES

Pharmaceutical Compositions

The following examples of pharmaceutical formulations illustrate the present invention without restricting its scope:

Some examples of formulations will now be described, wherein the term "active substance" denotes one or more compounds according to the invention including the salts thereof. In the case of one of the aforementioned combinations with one or more other active substances the term "active substance" also includes the additional active substances.

Example A

Tablets Containing 100 mg of Active Substance

Composition:
1 tablet contains:

| | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Example B

Tablets Containing 150 mg of Active Substance

Composition:
1 tablet contains:

| | |
|---|---|
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Example C

Hard Gelatine Capsules Containing 150 mg of Active Substance 1 capsule contains:

| | |
|---|---|
| active substance | 150.0 mg |
| corn starch (dried) | approx. 80.0 mg |
| lactose (powdered) | approx. 87.0 mg |
| magnesium stearate | 3.0 mg |
| | approx. 320.0 mg |

Capsule shell: size 1 hard gelatine capsule.

Example D

Suppositories Containing 150 mg of Active Substance 1 suppository contains:

| active substance | 150.0 mg |
|---|---|
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Example E

Ampoules Containing 10 mg Active Substance

Composition:

| active substance | 10.0 mg |
|---|---|
| 0.01 N hydrochloric acid | q.s. |
| double-distilled water | ad 2.0 ml |

Example F

Ampoules Containing 50 mg of Active Substance

Composition:

| active substance | 50.0 mg |
|---|---|
| 0.01 N hydrochloric acid | q.s. |
| double-distilled water | ad 10.0 ml |

The preparation of any the above mentioned formulations can be done following standard procedures.
Biological Assay
The in vitro effect of the compounds of the invention can be shown with the following biological assays.
PDE Assay Protocol:
The PDE enzymatic activity assays were run as SPA, in general according to the protocol of the manufacturer (Amersham Biosciences, product number: TRKQ 7100). As enzyme source, lysate (PBS with 1% Triton X-100 supplemented with protease inhibitors, cell debris removed by centrifugation at 13.000 rpm for 30 min) of SF 9 cell expressing the human PDE of interest was used. The total protein amount included in the assay varied upon infection and production efficacy of the SF9 cells and lay in the range of 0.1-100 ng.
In general, the assay conditions were as follows:
total assay volume: 40 µl
protein amount: 0.1-50 ng
substrate concentration (cGMP or cAMP): 20 nM; ~1 mCi/l
incubation time: 60 min at room temperature
final DMSO concentration: 1%
The assays were run in 384-well format. The test reagents as well as the enzyme and the substrate were diluted in assay buffer. The assay buffer contained 50 mM Tris, 8.3 mM MgCl2, 1.7 mM EGTA, 0.1% BSA, 0.05% Tween 20; the pH of assay buffer was adjusted to 7.5. In case activity of PDE1C was analysed, 50 nM Calmodulin and 3 mM CaCl2 were included in the assay buffer. In case PDE9 activity was analyzed, the reaction was stopped by applying a PDE9 specific inhibitor (e.g. compounds according to WO2004/099210). PDE1C was analysed with cAMP as substrate, and PDE9 was analyzed with cGMP as substrate.
Calculation of % Inhibition:
The activity of the positive control (minus the negative control=background) is set to 100% and activity in the presence of test compound is expressed relative to these 100%.
Within this setting, an inhibition above 100% might be possible due to the nature of the variation of the positive control within the assay, however, in this case the reported % inhibition had been adjusted to 100%.
Calculation of IC50:
IC50 can be calculated in a conventional way, eventually with the help of GraphPadPrism or other suited software setting the positive control as 100 and the negative control as 0. For calculation of IC50 usually 8 dilutions of the test compound (substrates) are to be selected and tested following the aforementioned protocol.

For to illustrate the pharmacological properties of the compounds according to the present invention in the following are given some illustrative and representative examples thereof, which are not considered to be limiting.

| Example No. | % inhibition PDE9A at 10 micromolar* | IC50 PDE9A (nanomolar)* | Selectivity* = IC 50 PDE 1C/IC 50 PDE9A (both nanomolar) |
|---|---|---|---|
| 1 | 99 | between 10 and 500 | 39 |
| 2 | 98 | between 10 and 500 | 14 |
| 3 | 95 | between 10 and 500 | 4 |
| 4 | 102 | between 10 and 500 | 88 |
| 5 | 96 | between 10 and 500 | 7 |
| 6 | 88 | between 10 and 500 | 112 |
| 7 | 91 | between 10 and 500 | 9 |
| 8 | 93 | between 10 and 500 | 21 |
| 9 | 90 | between 10 and 500 | 6 |
| 10 | 88 | more than 500 | 7 |
| 11 | 47 | more than 500 | 21 |
| 12 | 102 | between 10 and 500 | 8 |
| 13 | 96 | between 10 and 500 | 10 |
| 14 | 95 | between 10 and 500 | 14 |
| 15 | 94 | between 10 and 500 | 271 |
| 16 | 93 | between 10 and 500 | 71 |
| 17 | 98 | between 10 and 500 | 9 |
| 18 | 86 | between 10 and 500 | 28 |
| 19 | 74 | between 10 and 500 | 5 |
| 20 | 87 | between 10 and 500 | 4 |
| 21 | 91 | between 10 and 500 | 93 |
| 22 | 98 | between 10 and 500 | 14 |
| 23 | 85 | more than 500 | 46 |
| 24 | 87 | more than 500 | 49 |
| 25 | 58 | more than 500 | 24 |
| 26 | 51 | more than 500 | 24 |
| 27 | 67 | more than 500 | 14 |
| 28 | 96 | between 10 and 500 | 8 |
| 29 | 89 | between 10 and 500 | 9 |
| 30 | 95 | between 10 and 500 | 8 |
| 30-1 | 101 | between 10 and 500 | 55 |
| 30-2 | 100 | between 10 and 500 | 55 |
| 30-3 | 100 | between 10 and 500 | 14 |
| 30-4 | 99 | between 10 and 500 | 3 |
| 30-5 | 97 | between 10 and 500 | 26 |
| 31 | 82 | more than 500 | 8 |
| 32 | 91 | between 10 and 500 | 11 |
| 33 | 89 | between 10 and 500 | 4 |
| 34 | 60 | more than 500 | 19 |

-continued

| Example No. | % inhibition PDE9A at 10 micromolar* | IC50 PDE9A (nanomolar)* | Selectivity* = IC 50 PDE 1C/IC 50 PDE9A (both nanomolar) |
|---|---|---|---|
| 35 | 93 | between 10 and 500 | 10 |
| 36 | 98 | between 10 and 500 | 54 |
| 37 | 99 | between 10 and 500 | 27 |
| 38 | 92 | more than 500 | 9 |
| 39 | 97 | between 10 and 500 | 4 |

*for illustrative purposes

The in vivo effect of the compounds of this invention can be tested in the Novel Object Recognition test according to the procedure of Prickaerts et al. (*Neuroscience*, 2002, 113, 351-361).

Chemical Manufacture

Abbreviations:

DIPEA di-isopropyl-ethylamine
DMSO dimethyl sulphoxide
ESI electrospray ionization (in MS)
h hour(s)
HPLC high performance liquid chromatography
HPLC-MS coupled high performance liquid chromatography-mass spectroscopy
MPLC medium pressure liquid chromatography
min minutes
MS mass spectroscopy
Psi pounds per square inch
$R_f$ retention factor
RT retention time (in HPLC)
TBTU 2-(1H-Benzotriazole-1-yl)-1,1,3,3-tetramethyluronium-tetrafluoroborate
TFA trifluoroacetic acid
TLC thin-layer chromatography LC-MS Methods:

Method 1

MS apparatus type: Waters Micromass ZQ; HPLC apparatus type: Waters Alliance 2695, Waters 2996 diode array detector; column: Varian Microsorb 100 C18, 30×4.6 mm, 3.0 µm; eluent A: water+0.13% TFA, eluent B: acetonitrile; gradient: 0.0 min 5% B→0.18 min 5% B→2.0 min 98% B→2.2 min 98% B→2.3 min 5% B→2.5 min 5% B; flow rate: 3.5 ml/min; UV detection: 210-380 nm.

Method 2

MS apparatus type: Waters Micromass ZQ; HPLC apparatus type: Waters Alliance 2695, Waters 2996 diode array detector; column: Merck Chromolith Performance RP18e, 100×1 mm; eluent A: water+0.13% TFA, eluent B: acetonitrile; gradient: 0.0 min 5% B→0.2 min 5% B→1.6 min 98% B→1.9 min 98% B→2.0 min 5% B→2.2 min 5% B; flow rate: 3.5 ml/min; UV detection: 210-380 nm.

Method 3

Instrument: LC/MS ThermoFinnigan. Hplc Surveyor DAD, LCQduo Ion trap; column: Sunryse MS-C18, 5 um, 4.6×100 mm; eluent A: 95% water+5% acetonitrile+20 mM ammonium formate; eluent B: 95% acetonitrile+5% water+20 mM ammonium formate; gradient: A/B (95:5) for 1 min, then to A/B (5:95) in 7 min for 1.5 min; flow rate: 0.85 ml/min; UV detection: 254 nm; Ion source: ESI.

Method Grad_C8_Acidic

Instrument: LC/MS Waters. Hplc Alliance 2695 DAD, ZQ Quadrupole; column: Xterra MS-C8, 3.5 um, 4.6×50 mm; eluent A: water+0.1% TFA+10% acetonitrile; eluent B: acetonitrile; gradient: A/B (80:20), then to A/B (10:90) in 3.25 min for 0.75 min; flow rate: 1.3 ml/min; UV Detection: 254 nm; Ion source: ESI.

Method Grad_C8_NH4COOH

Instrument: LC/MS Waters. Hplc Alliance 2695 DAD, ZQ Quadrupole. Column: Xterra MS-C8, 3.5 um, 4.6×50 mm; eluent A: water+ammonium formate 5 mM+10% acetonitrile; eluent B: acetonitrile; gradient: A 100, then to A/B (10:90) in 3.25 min for 0.75 min; flow rate: 1.3 ml/min; UV Detection: 254 nm; Ion source: ESI.

Method Grad_C18_Acidic

Instrument: LC/MS Waters. Hplc Alliance 2695 DAD, ZQ Quadrupole; column: Sunfire MS-C18, 3.5 um, 4.6×50 mm; eluent A: water+0.1% TFA+10% acetonitrile; eluent B: acetonitrile; gradient: A/B (80:20), then to A/B (10:90) in 3.25 min for 0.75 min; flow rate: 1.3 ml/min; UV Detection: 254 nm; Ion source: ESI.

Method 1D

Instrument: LC/MS ThermoFinnigan. Hplc Surveyor DAD, MSQ Quadrupole; column: Sunfire MS-C18, 5 um, 4.6×100 mm; eluent A: 90% water+10% acetonitrile+ammonium formate 10 mM; eluent B: acetonitrile 90%+10% water+ammonium formate 10 mM; gradient: A (100) for 1 min, then to B (100) in 7 min for 1 min; flow rate: 1.2 mL/min; UV Detection: 254 nm; Ion source: APCI.

Method 1E

Instrument: LC/MS ThermoFinnigan. Hplc Surveyor DAD, MSQ Quadrupole; column: Symmetry C8, 5 um, 3×150 mm; eluent A: 90% water+10% acetonitrile+ammonium formate 10 mM; eluent B=acetonitrile 90%+10% $H_2O$+$NH_4COOH$ 10 mM; gradient: A (100) for 1.5 min, then to B (100) in 10 min for 1.5 min; flow rate: 1.2 mL/min; UV Detection: 254 nm; Ion source: APCI.

Microwave Heating:

Microwave apparatus type: Biotage Initiator Sixty.
Discover® CEM instruments, equipped with 10 and 35 mL vessels;

Starting Compounds

Example 1A

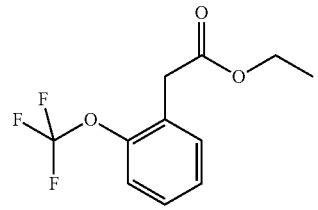 [SMILES: CCOC(=O)Cc1ccccc1OC(F)(F)F]

20.0 g (90.9 mmol) of (2-trifluoromethoxy-phenyl)-acetic acid were dissolved in 150 ml of absolute ethanol. At 0° C. 10.0 ml (138 mmol) of thionylchloride were slowly added. The solution was heated to 50° C. for 12 h. Cooling to room temperature was followed by evaporation of the solvent under reduced pressure. The remaining residue was dissolved in 10 ml of ethyl acetate and filtered through a pad of activated basic alumina. The ester was obtained as a colourless oil (18.4 g, 81% of theory).

HPLC-MS (Method 1): RT: 1.64 min

MS (ESI pos): m/z=249 (M+H)+.

Example 1B

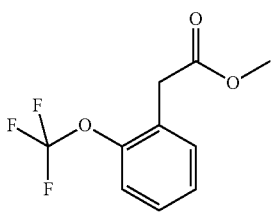 [SMILES: COC(=O)Cc1ccccc1OC(F)(F)F]

In analogy to the preparation of example 1A, the methyl ester was obtained using absolute methanol instead of ethanol.

Example 2A

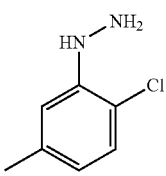

10.0 g (70.6 mmol) of 2-chloro-5-methyl-aniline were dissolved in 38 ml hydrochloric acid (20% in water). At −5° C. a solution of 5.36 g (77.7 mmol) of sodium nitrite in 70 ml water was added drop wise within 40 min and kept at this temperature for further 30 min. The cold solution was added drop wise to a solution of 40.2 g (178 mmol) of tin(II)-chloride dihydrate in 48 ml of hydrochloric acid (32% in water), maintaining the temperature at −10° C. The resulting suspension was heated to 25° C. and stirred for 12 h. The suspension was cooled to 0° C. and 350 ml sodium hydroxide (40% in water) were added. The solution was extracted with ethyl acetate three times. The organic layers were collected, extracted with water and dried over magnesium sulphate. Filtration and evaporation of the solvent under reduced pressure yielded the hydrazine as a solid. (9.6 g, 87% of theory).

HPLC-MS (Method 1): RT: 0.90 min

MS (ESI pos): m/z=157/159 (Cl) (M+H)$^+$ and 140/142 (Cl) (M—NH$_3$+H)$^+$.

The following examples were synthesized in analogy to the preparation of example 2A, using the corresponding anilines as starting materials:

| | structure | starting material | RT [min] | MS (ESI pos, m/z) |
|---|---|---|---|---|
| Example 2B | 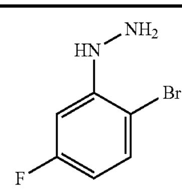 | 2-Bromo-5-fluoro-phenylamine | 0.83 (Method 1) | 205/207 (Br) (M + H)$^+$ and 188/190 (Br) (M - NH$_3$ + H)$^+$ |
| Example 2C | 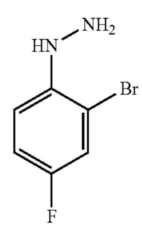 | 2-Bromo-4-fluoro-phenylamine | 0.81 (Method 1) | 205/207 (Br) (M + H) and 188/190 (Br) (M - NH$_3$ + H)$^+$ |
| Example 2D | | 2-Bromo-5-methyl-phenylamine (commercial from Anichem, North Brunswick, USA) | 0.96 (Method 1) | 201/203 (Br) (M + H)$^+$ and 184/186 (Br) (M - NH$_3$ + H)$^+$ |
| Example 2D | | 5-Chloro-2-methyl-phenylamine | 0.86 (Method 1) | |

-continued

| | structure | starting material | RT [min] | MS (ESI pos, m/z) |
|---|---|---|---|---|
| Example 2E | (4-fluoro-2-methylphenyl)hydrazine | 4-Fluoro-2-methyl-phenylamine | 0.81 (Method 1) | 141 (M + H)+ |
| Example 2F | (2-chloro-5-ethoxyphenyl)hydrazine | 2-Chloro-5-ethoxy-phenylamine | 0.99 (Method 1) | 187 (M + H)+ |
| Example 2G | (4,5-difluoro-2-methylphenyl)hydrazine | 4,5-Difluoro-2-methyl-phenylamine | 0.88 (Method 1) | 159 (M + H)+ |
| Example 2H | (2-chloro-5-methoxyphenyl)hydrazine | 2-Chloro-5-methoxy-phenylamine | 0.86 (Method 1) | 173/175 (Cl) (M + H)+ |
| Example 2I | (2-chloro-4-fluoro-5-methylphenyl)hydrazine | 2-Chloro-4-fluoro-5-methyl-phenylamine | 0.97 (Method 1) | |
| Example 2J | (4-fluoro-2-isopropoxyphenyl)hydrazine | 4-Fluoro-2-isopropoxy-phenylamine | 1.03 (Method 1) | |
| Example 2K | (2-chloro-6-methylphenyl)hydrazine | 2-Chloro-6-methyl-phenylamine | 0.76 (Method 1) | 158/160 (Cl) (M + H)+ |

| | structure | starting material | RT [min] | MS (ESI pos, m/z) |
|---|---|---|---|---|
| Example 2L | 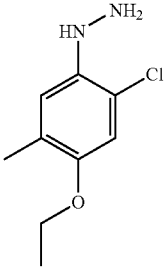 | 2-Chloro-4-ethoxy-5-methyl-phenylamine | 0.97 (Method 1) | |
| Example 2M | 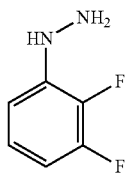 | 2,3-Difluoro-phenylamine | | |

Example 3A

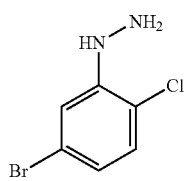

5.0 g (23.9 mmol) of 4-bromo-1-chloro-2-fluoro-benzene and 4.64 ml (95.5 mmol) of hydrazine hydrate were dissolved in 8 ml DMSO. The solution was stirred for 48 h at 70° C. The mixture was cooled to 25° C. and water was added. The precipitate formed was collected by filtration and washed with water. After drying under reduced pressure the hydrazine was obtained as a solid. (2.6 g, 49% of theory).

HPLC-MS (Method 1): RT: 0.93 min

MS (ESI pos): m/z=221/223/225 (Br, Cl) (M+H)$^+$ and 204/206/208 (Br, Cl) (M—NH$_3$+H)$^+$.

The following example was synthesized in analogy to the preparation of example 3A, using the corresponding aryl fluoride as starting material:

| | structure | starting material | RT [min] | MS (ESI pos, m/z) |
|---|---|---|---|---|
| Example 3B | 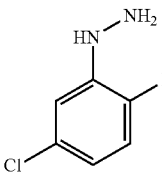 | 1-bromo-4-chloro-2-fluoro-benzene | 0.92 (Method 1) | 221/223/225 (Br, Cl) (M + H)$^+$ |

Example 4A

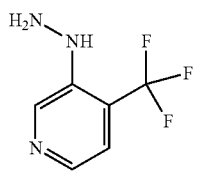

3.0 g (18.5 mmol) of 3-amino-4-(trifluoromethyl)-pyridine were dissolved in 15 ml hydrochloric acid (12N). The reaction mixture was cooled at −20° C.; and then a solution of sodium nitrite (1.4 g; 20.35 mmol) in 15 ml of water was added dropwise, keeping the temperature at −15° C. After 1 hour, the reaction mixture was added drop wise to a solution of tin(II)-chloride dihydrate (12.53 g; 55.53 mmol) in 7.5 ml hydrochloric acid (12N) keeping the temperature at −15° C. After 1 hour the reaction was complete; the pH of the reaction mixture was adjusted to 10-11 by addition of 40% KOH at −20° C.; the product was extracted by ethyl acetate. After drying under reduced pressure the hydrazine was obtained as a red solid. (2.5 g; 14.11 mmol; yield 76%).

HPLC-MS (Method 1E): RT: 4.48 min

MS (APCI): m/z=178 (M+H)$^+$.

The following examples were synthesized in analogy to the preparation of example 4A, using the corresponding aminopyridines as starting materials:

| | structure | starting material | RT [min] | MS (ESI pos, m/z) |
|---|---|---|---|---|
| Example 4B | (structure) | 6-Fluoro-pyridin-3-ylamine | 0.45 (Method: Grad_C8_acidic) | 128 (M + H) |
| Example 4C | (structure) | Pyridin-3-ylamine | 2.6 (Method 3) | 110 (M + H)⁺ |

Example 5A

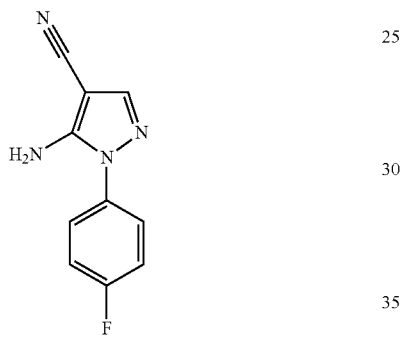

8.7 g (53.5 mmol) of 4-fluorphenylhydrazine hydrochloride was suspended with 6.5 g (53.5 mmol) of ethoxymethylenemalononitrile in 13 ml of ethanol, and 22.2 ml (160 mmol) of triethylamine were added. The reaction mixture was heated to 50° C. for 2 h. After cooling to room temperature the solvent was removed under reduced pressure. The remaining residue was treated with water (25 ml) and extracted three times with ethyl acetate. The organic layer was dried over sodium sulphate, filtered and the filtrate was concentrated under reduced pressure. The remaining residue was purified by preparative MPLC (SiO$_2$, eluent CH$_2$Cl$_2$). 5.0 g (46% of theory) of the product were obtained as an oil, that solidifies over night.

LC-MS (Method 1): RT=1.06 min

MS (ESI pos): m/z=203 (M+H)⁺.

The following examples were synthesized in analogy to the preparation of example 5A, using the corresponding hydrazines as starting materials:

| | structure | starting material | RT [min] | MS (ESI pos, m/z) |
|---|---|---|---|---|
| Example 5B | (structure) | (5-Chloro-2-methoxy-phenyl)-hydrazine hydrochloride (commercial from ACB Blocks Ltd., Moscow, Russia) | 1.27 (Method 1) | 249/251 (Cl) (M + H)⁺ |
| Example 5C | (structure) | (2-Chloro-5-fluoro-phenyl)-hydrazine hydrochloride (commercial from Apollo Scientific, Cheshire, UK) | 1.13 (Method 1) | 237/239 (Cl) (M + H)⁺ |

| | structure | starting material | RT [min] | MS (ESI pos, m/z) |
|---|---|---|---|---|
| Example 5D | 5-amino-1-(2,4-difluorophenyl)-1H-pyrazole-4-carbonitrile | (2,4-Difluoro-phenyl)hydrazine hydrochloride | 1.05 (Method 1) | 221 (M + H)⁺ |
| Example 5E | 5-amino-1-(5-fluoro-2-methylphenyl)-1H-pyrazole-4-carbonitrile | (5-Fluoro-2-methyl-phenyl)-hydrazine hydrochloride | 1.18 (Method 1) | 217 (M + H)⁺ |
| Example 5F | 5-amino-1-(2-chloro-4-fluorophenyl)-1H-pyrazole-4-carbonitrile | (2-Chloro-5-fluoro-phenyl)-hydrazine hydrochloride | 1.15 (Method 1) | 237/239 (Cl) (M + H)⁺ |
| Example 5G | 5-amino-1-(2,5-dichlorophenyl)-1H-pyrazole-4-carbonitrile | (2,5-Dichloro-phenyl)-hydrazine hydrochloride | 1.28 (Method 1) | 254/256/258 (2Cl) (M + H)⁺ |
| Example 5H | 5-amino-1-(2,5-dimethylphenyl)-1H-pyrazole-4-carbonitrile | (2,5-Dimethyl-phenyl)-hydrazine hydrochloride | 1.02 (Method 1) | 231 (M + H)⁺ |

-continued

| | structure | starting material | RT [min] | MS (ESI pos, m/z) |
|---|---|---|---|---|
| Example 5I | 5-amino-1-(2,3-dimethylphenyl)-1H-pyrazole-4-carbonitrile | (2,3-Dimethyl-phenyl)-hydrazine hydrochloride | 1.23 (Method 1) | 213 (M + H)+ |
| Example 5J | 5-amino-1-(2,6-dichlorophenyl)-1H-pyrazole-4-carbonitrile | (2,6-Dichloro-phenyl)-hydrazine hydrochloride | 1.23 (Method 1) | 254/256/258 (2 Cl) (M + H)+ |
| Example 5K | 5-amino-1-(3-fluorophenyl)-1H-pyrazole-4-carbonitrile | (3-Fluoro-phenyl)-hydrazine hydrochloride | 1.16 (Method 1) | 203 (M + H)+ |
| Example 5L | 5-amino-1-(3-fluoro-2-methylphenyl)-1H-pyrazole-4-carbonitrile | (3-Fluoro-2-methyl-phenyl)-hydrazine hydrochloride (commercial from Matrix Scientific, Columbia, USA), US2002/169163 | 1.08 (Method 1) | 215 (M + H)+ |
| Example 5M | 5-amino-1-(2,3-dichlorophenyl)-1H-pyrazole-4-carbonitrile | (2,3-Dichloro-phenyl)-hydrazine hydrochloride | 1.24 (Method 1) | 251/253 (2Cl) (M + H)+ |

| | structure | starting material | RT [min] | MS (ESI pos, m/z) |
|---|---|---|---|---|
| Example 5N | 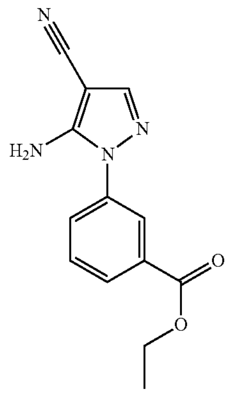 [SMILES: CCOC(=O)c1cccc(-n2ncc(C#N)c2N)c1] | 3-Hydrazino-benzoic acid ethyl ester hydrochloride | 1.25 (Method 1) | 257 (M + H)⁺ |
| Example 5O | 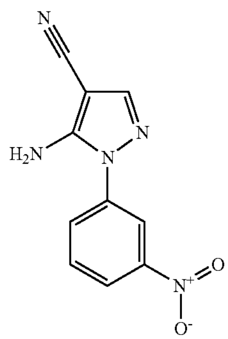 [SMILES: N#Cc1cnn(-c2cccc([N+](=O)[O-])c2)c1N] | 3-Nitrophenylhydrazine hydrochloride | 1.16 (Method 1) | |

Example 6A

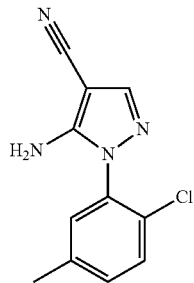 [SMILES: Cc1ccc(Cl)c(-n2ncc(C#N)c2N)c1]

9.6 g (61.3 mmol) of example 2A and 7.49 g (61.3 mmol) of ethoxymethylenemalononitrile in 15 ml of ethanol, and 17.0 ml (123 mmol) of triethylamine were added. The reaction mixture was heated to 50° C. for 3 h. After cooling to room temperature the solvent was removed under reduced pressure. The remaining residue was dissolved in ethyl acetate and extracted twice with a saturated aqueous solution of sodium hydrogen carbonate. The organic layer was dried over sodium sulphate, filtered and the filtrate was concentrated under reduced pressure. The remaining residue was purified by preparative MPLC (SiO₂, eluent CH₂Cl₂). 7.2 g (51% of theory) of the product were obtained as an oil, that solidifies over night.

LC-MS (Method 1): RT=1.26 min

MS (ESI pos): m/z=233/235 (Cl) (M+H)⁺.

The following examples were synthesized in analogy to the preparation of example 6A, using the corresponding hydrazines as starting materials:

| | structure | starting material | RT [min] | MS (ESI pos, m/z) |
|---|---|---|---|---|
| Example 6B | 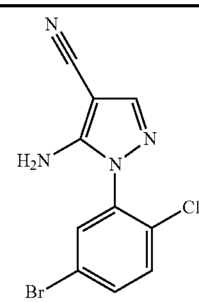 | Example 3A | 1.32 (Method 1) | 297/299/301 (Br, Cl) (M + H)⁺ |
| Example 6C | 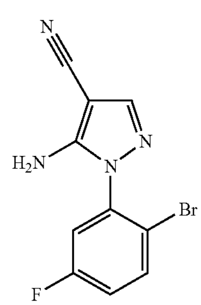 [SMILES: N#Cc1cnn(-c2cc(Cl)ccc2Br)c1N] | Example 2B | 1.31 (Method 1) | 281/283 (Br) (M + H)⁺ |

| | structure | starting material | RT [min] | MS (ESI pos, m/z) |
|---|---|---|---|---|
| Example 6D | 5-amino-1-(2-bromo-5-chlorophenyl)-1H-pyrazole-4-carbonitrile | Example 3B | 1.34 (Method 1) | 297/299/301 (Br, Cl) (M + H)+ |
| Example 6E | 5-amino-1-(2-bromo-4-fluorophenyl)-1H-pyrazole-4-carbonitrile | Example 2C | 1.18 (Method 1) | 281/283 (Br) (M + H)+ |
| Example 6F | 5-amino-1-(2-bromo-5-methylphenyl)-1H-pyrazole-4-carbonitrile | Example 2D | 1.25 (Method 1) | 277/279 (Br) (M + H)+ |
| Example 6G | 5-amino-1-(5-chloro-2-methylphenyl)-1H-pyrazole-4-carbonitrile | Example 2D | 1.32 (Method 1) | 234/236 (Cl) (M + H)+ |
| Example 6H | 5-amino-1-(4-fluoro-2-methylphenyl)-1H-pyrazole-4-carbonitrile | Example 2E | 1.17 (Method 1) | 217 (M + H)+ |
| Example 6I | 5-amino-1-(2-chloro-5-ethoxyphenyl)-1H-pyrazole-4-carbonitrile | Example 2F | 1.33 (Method 1) | 263/265 (Cl) (M + H)+ |
| Example 6J | 5-amino-1-(4,5-difluoro-2-methylphenyl)-1H-pyrazole-4-carbonitrile | Example 2G | 1.23 (Method 1) | 235 (M + H)+ |
| Example 6K | 5-amino-1-(2-chloro-5-methoxyphenyl)-1H-pyrazole-4-carbonitrile | Example 2H | 1.19 (Method 1) | 249/251 (Cl) (M + H)+ |
| Example 6L | 5-amino-1-(2-chloro-4-fluoro-5-methylphenyl)-1H-pyrazole-4-carbonitrile | Example 2I | 1.31 (Method 1) | 251/253 (Cl) (M + H)+ |

| structure | starting material | RT [min] | MS (ESI pos, m/z) |
|---|---|---|---|
| Example 6M 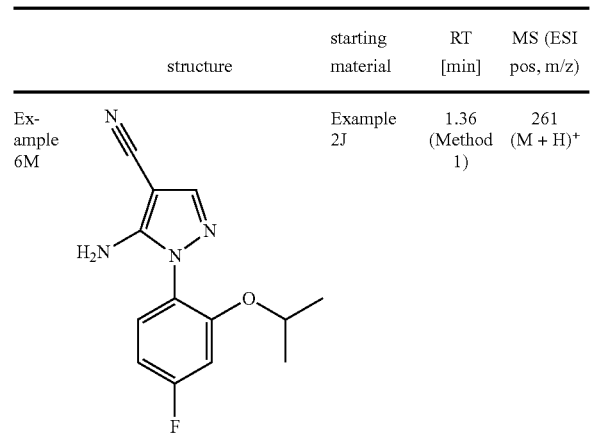 | Example 2J | 1.36 (Method 1) | 261 (M + H)+ |
| Example 6N | Example 2K | 1.23 (Method 1) | 233/235 (Cl) (M + H)+ |
| Example 6O | Example 2L | 1.31 (Method 1) | 251/253 (Cl) (M + H)+ |
| Example 6P 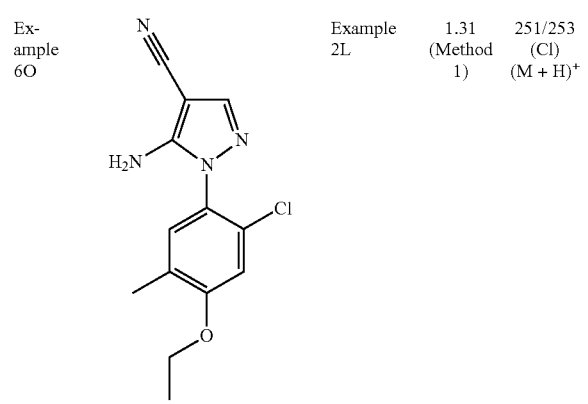 | (3-Fluoro-2-methoxyphenyl)-hydrazine (commercial from_Beta Pharma, Inc., New Haven, CT, USA) | 1.06 (Method 1) | 233 (M + H)+ |
| Example 6Q 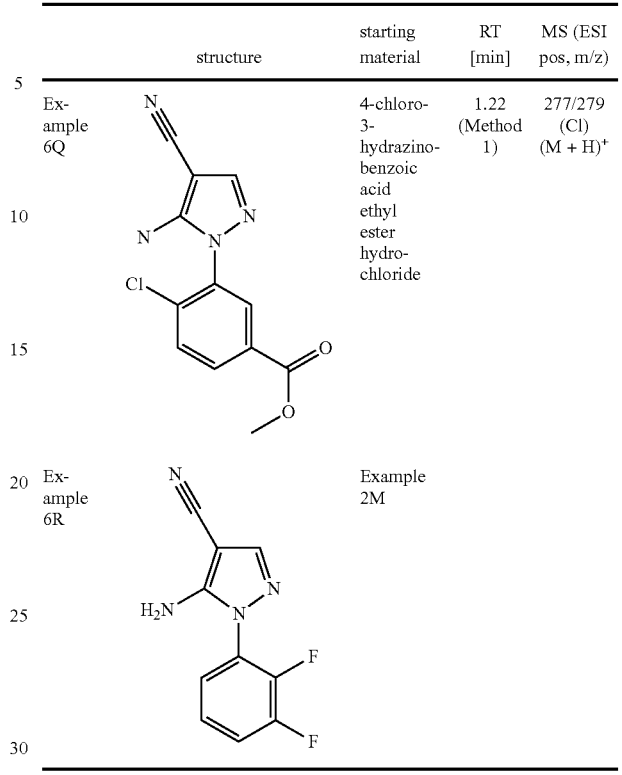 | 4-chloro-3-hydrazinobenzoic acid ethyl ester hydrochloride | 1.22 (Method 1) | 277/279 (Cl) (M + H)+ |
| Example 6R | Example 2M | | |

Example 7A

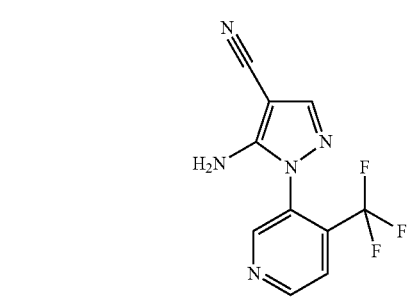 [SMILES: N#Cc1cnn(-c2cnccc2C(F)(F)F)c1N]

To a solution of example 4A (2.5 g; 14.11 mmol) in ethyl alcohol (170 ml) ethoxymethylenemalononitrile (1.72 g; 14.11 mmol) was added in portions and then the reaction mixture was refluxed during one hour. The reaction mixture was then allowed to reach room temperature observing the formation of a solid that was filtered off and purified by flash chromatography. 2.2 g of the desired compound were obtained (8.68 mmol; yield=61.6%).

LC-MS (Method Grad-C8-NH4COOH): RT=1.88 min
MS (ESI pos): m/z=254 (M+H)+.

The following examples were synthesized in analogy to the preparation of example 7A, using the corresponding hydrazines as starting materials:

| | structure | starting material | RT [min] | MS (m/z) |
|---|---|---|---|---|
| Example 7B | 5-amino-1-(6-fluoropyridin-3-yl)-1H-pyrazole-4-carbonitrile | Example 4B | 1.12 (Method Grad_C18_acidic) | 204 (M + H)⁺ ESI |
| Example 7C | 5-amino-1-(pyridin-3-yl)-1H-pyrazole-4-carbonitrile | Example 4C | 3.50 (Method 1E) | 186 (M + H)⁺ APCI |
| Example 7D | 5-amino-1-(3,5-difluoropyridin-2-yl)-1H-pyrazole-4-carbonitrile | 3,5-Difluoro-2hydrazinopyridine (Apollo Scientific Fluorine Chemicals) | 2.22 (Method Grad_C8_NH4COOH) | 221 (M + H)⁺ ESI |

Example 8A

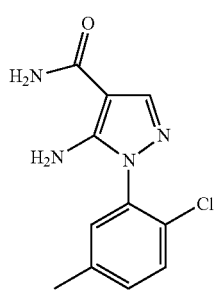 [SMILES: Cc1ccc(Br)c(-n2ncc(C(N)=O)c2N)c1]

7.2 g (31.0 mmol) of example 6A was dissolved in 250 ml of ethanol. At 25° C. a solution of 66.5 ml (0.77 mol) hydrogen peroxide (35% in water) in 300 ml ammonia (25% in water) was added slowly over a period of 10 min. The solution was carefully concentrated to a volume of 30 ml under reduced pressure. The precipitate formed was collected by filtration and purified by preparative HPLC (eluent A: water+ 0.13% TFA, eluent B: acetonitrile). 5.8 g (75% of theory) of the product were obtained as a colourless solid.

LC-MS (Method 1): RT=0.66 min

MS (ESI pos): m/z=251/253 (Cl) (M+H)⁺.

The following examples were synthesized in analogy to the preparation of example 8A, using the corresponding 5-amino-1H-pyrazole-4-carbonitriles as starting materials:

| | structure | starting material | RT [min] | MS (ESI pos, m/z) |
|---|---|---|---|---|
| Example 8B | 5-amino-1-(5-chloro-2-methoxyphenyl)-1H-pyrazole-4-carboxamide | Example 5B | 1.05 (Method 1) | 267/269 (Cl) (M + H)⁺ |
| Example 8C | 5-amino-1-(2-chloro-5-fluorophenyl)-1H-pyrazole-4-carboxamide | Example 5C | 0.94 (Method 1) | 255/257 (Cl) (M + H)⁺ |
| Example 8D | 5-amino-1-(5-bromo-2-chlorophenyl)-1H-pyrazole-4-carboxamide | Example 6B | 1.09 (Method 1) | 315/317/319 (Br, Cl) (M + H)⁺ |
| Example 8E | 5-amino-1-(2-bromo-5-fluorophenyl)-1H-pyrazole-4-carboxamide | Example 6C | 0.88 (Method 1) | 299/301 (Br) (M + H)⁺ |
| Example 8F | 5-amino-1-(2-bromo-5-chlorophenyl)-1H-pyrazole-4-carboxamide | Example 6D | 1.08 (Method 1) | 315/317/319 (Br, Cl) (M + H)⁺ |

-continued

| | structure | starting material | RT [min] | MS (ESI pos, m/z) |
|---|---|---|---|---|
| Example 8G | 5-amino-1-(2-bromo-4-fluorophenyl)-1H-pyrazole-4-carboxamide | Example 6E | 0.94 (Method 1) | 299/301 (Br) (M + H)+ |
| Example 8H | 5-amino-1-(2-bromo-5-methylphenyl)-1H-pyrazole-4-carboxamide | Example 6F | 1.06 (Method 1) | 295/297 (Br) (M + H)+ |
| Example 8I | 5-amino-1-(4-fluorophenyl)-1H-pyrazole-4-carboxamide | Example 5A | 0.89 (Method 1) | 221 (M + H)+ |
| Example 8J | 5-amino-1-(2,4-difluorophenyl)-1H-pyrazole-4-carboxamide | Example 5D | 0.86 (Method 1) | 239 (M + H)+ |

-continued

| | structure | starting material | RT [min] | MS (ESI pos, m/z) |
|---|---|---|---|---|
| Example 8K | 5-amino-1-(2-chloro-4-fluorophenyl)-1H-pyrazole-4-carboxamide | Example 5F | 0.94 (Method 1) | 255/257 (Cl) (M + H)+ |
| Example 8L | 5-amino-1-(5-fluoro-2-methylphenyl)-1H-pyrazole-4-carboxamide | Example 5E | 0.93 (Method 1) | 235 (M + H)+ |
| Example 8M | 5-amino-1-(5-chloro-2-methylphenyl)-1H-pyrazole-4-carboxamide | Example 6G | 1.08 (Method 1) | 251/253 (Cl) (M + H)+ |
| Example 8N | 5-amino-1-(2,5-dichlorophenyl)-1H-pyrazole-4-carboxamide | Example 5G | 1.06 (Method 1) | 272/274/276 (2Cl) (M + H)+ |
| Example 8O | 5-amino-1-(4-fluoro-2-methylphenyl)-1H-pyrazole-4-carboxamide | Example 6H | 0.96 (Method 1) | 235 (M + H)+ |

-continued

| | structure | starting material | RT [min] | MS (ESI pos, m/z) |
|---|---|---|---|---|
| Example 8P | 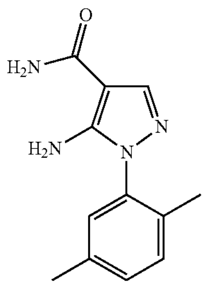 [SMILES: Cc1ccc(C)c(-n2ncc(C(N)=O)c2N)c1] | Example 5H | 1.02 (Method 1) | 231 (M + H)+ |
| Example 8Q | 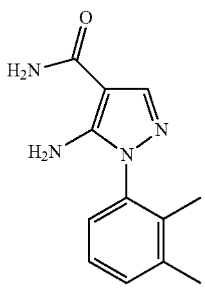 [SMILES: Cc1cccc(-n2ncc(C(N)=O)c2N)c1C] | Example 5I | 0.99 (Method 1) | 231 (M + H)+ |
| Example 8R | 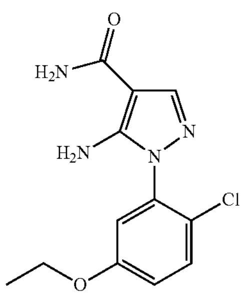 [SMILES: CCOc1ccc(Cl)c(-n2ncc(C(N)=O)c2N)c1] | Example 6I | 1.10 (Method 1) | 281/283 (Cl) (M + H)+ |
| Example 8S | 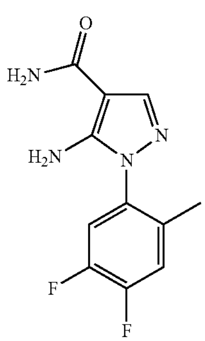 [SMILES: Cc1cc(F)c(F)cc1-n1ncc(C(N)=O)c1N] | Example 6J | 1.00 (Method 1) | 253 (M + H)+ |
| Example 8T | 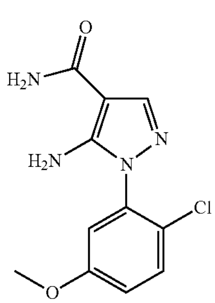 [SMILES: COc1ccc(Cl)c(-n2ncc(C(N)=O)c2N)c1] | Example 6K | 0.99 (Method 1) | 267/269 (Cl) (M + H)+ |

-continued

| | structure | starting material | RT [min] | MS (ESI pos, m/z) |
|---|---|---|---|---|
| Example 8U | 5-amino-1-(2-chloro-5-methyl-4-fluorophenyl)-1H-pyrazole-4-carboxamide | Example 6L | 1.08 (Method 1) | 269/271 (Cl) (M + H)+ |
| Example 8V | 5-amino-1-(4-fluoro-2-isopropoxyphenyl)-1H-pyrazole-4-carboxamide | Example 6M | 1.13 (Method 1) | 279 (M + H)+ |
| Example 8W | 5-amino-1-(2-chloro-6-methylphenyl)-1H-pyrazole-4-carboxamide | Example 6N | 0.96 (Method 1) | 251/253 (Cl) (M + H)+ |
| Example 8X | 5-amino-1-(2,6-dichloropyridin-3-yl)-1H-pyrazole-4-carboxamide | Example 5J | 0.94 (Method 1) | 271/273/275 (2Cl) (M + H)+ |
| Example 8Y | 5-amino-1-(3-fluorophenyl)-1H-pyrazole-4-carboxamide | Example 5K | 0.95 (Method 1) | 221 (M + H)+ |

-continued

| | structure | starting material | RT [min] | MS (ESI pos, m/z) |
|---|---|---|---|---|
| Example 8Z | 5-amino-1-(2-chloro-5-ethoxy-4-methylphenyl)-1H-pyrazole-4-carboxamide | Example 6O | 1.08 (Method 1) | 269/271 (Cl) (M + H)+ |
| Example 8AA | 5-amino-1-(3-fluoro-2-methylphenyl)-1H-pyrazole-4-carboxamide | Example 5L | 0.92 (Method 1) | 235 (M + H)+ |
| Example 8AB | 5-amino-1-(2,3-dichlorophenyl)-1H-pyrazole-4-carboxamide | Example 5M | 1.02 (Method 1) | 271/273 (2Cl) (M + H)+ |
| Example 8AC | 5-amino-1-(3-fluoro-2-methoxyphenyl)-1H-pyrazole-4-carboxamide | Example 6P | 0.86 (Method 1) | 251 (M + H)+ |

-continued

| | structure | starting material | RT [min] | MS (ESI pos, m/z) |
|---|---|---|---|---|
| Example 8AD | 5-amino-1-(3-(ethoxycarbonyl)phenyl)-1H-pyrazole-4-carboxamide | Example 5N | 1.08 (Method 1) | 275 (M + H)⁺ |
| Example 8AE | 5-amino-1-(3-nitrophenyl)-1H-pyrazole-4-carboxamide | Example 5O | 0.95 (Method 1) | |
| Example 8AF | 5-amino-1-(2-chloro-5-carboxyphenyl)-1H-pyrazole-4-carboxamide | Example 6Q | 0.86 (Method 1) | 281/283 (Cl) (M)⁺ |
| Example 8AJ | 5-amino-1-(2,3-difluorophenyl)-1H-pyrazole-4-carboxamide | Example 6R | | |

Example 8AG

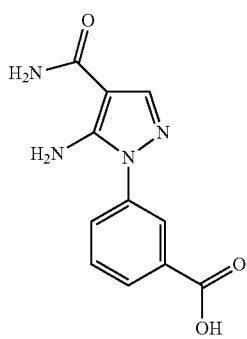 [SMILES: NC(=O)c1cnn(-c2cccc(C(=O)O)c2)c1N]

0.90 g of example 8 AD (3.50 mmol) were dissolved in 20 mL ethanol and 12 mL 2N NaOH solution was added. The mixture was stirred at room temperature for 2 h. The precipitate forming was filtered off and dried to give 0.60 g (70%) of example 8AG.

LC-MS (Method 1): RT=0.80 min

MS (ESI pos): m/z=245 (M−H)−.

Example 8AH

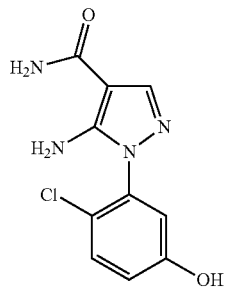 [SMILES: NC(=O)c1cnn(-c2cc(O)ccc2Cl)c1N]

0.25 g of example 8R (0.89 mmol) were dissolved in 2 mL dichloromethane and 2.5 mL BBr3 solution (1M in THF) was added. The mixture was stirred at room temperature for 48 h. Standard aqueous work up afforded 0.10 g (44%) of example 8AH.

LC-MS (Method 1): RT=0.82 min

MS (ESI pos): m/z=252/254 (Cl) (M)+.

Example 8AI

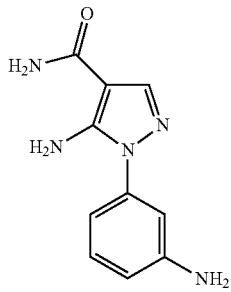 [SMILES: NC(=O)c1cnn(-c2cccc(N)c2)c1N]

4.79 g of example 8AE (19.0 mmol) were dissolved in 500 mL methanol and 1.0 g PD/C (10%) was added. The mixture was hydrogenated at room temperature for 4 h at 60 psi hydrogen pressure. Filtration and concentration afforded 4.06 g (98%) of example 8 AI.

LC-MS (Method 1): RT=0.36 min

Example 9A

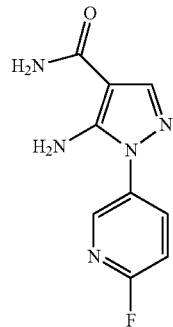

4.7 g of (23.13 mmol) of example 7B were dissolved in ethanol and then the temperature was lowered at 0°-5° C. A solution of 30% ammonium hydroxide (110 ml; 832 mmol) and 35% hydrogen peroxide (46 ml; 535 mmol) was then added drop wise. The reaction was heated to 20° C. and the reaction mixture stirred for two additional hours. The formed precipitate was filtered and dried under vacuum. 4.4 g of the desired compound were obtained (19.89 mmol; yield=86%).

LC-MS ((Method Grad-C18-Acidic): RT=0.6 min

MS (ESI pos): m/z=222 (M+H)+

The following examples were synthesized in analogy to the preparation of example 9A, using the corresponding 5-amino-1H-pyrazole-4-carbonitriles as starting materials:

|  | structure | starting material | RT [min] | MS (m/z) |
|---|---|---|---|---|
| Example 9B | 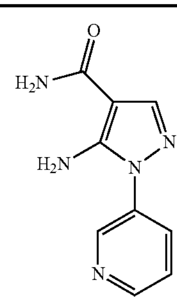 | Example 7C | 0.61 (Method GRAD_C8_NH4COOH) | 204 (M + H)+ ESI pos |

-continued

| structure | starting material | RT [min] | MS (m/z) |
|---|---|---|---|
| Example 9C <br> ![structure] | Example 7A | 3.72 (Method 1E) | 272 (M + H)+ APCI |
| Example 9D <br> ![structure] | Example 7D | 1.69 ((Method GRAD_C8_NH4COOH)) | 240 (M + H)+ ESI |

Example 10A

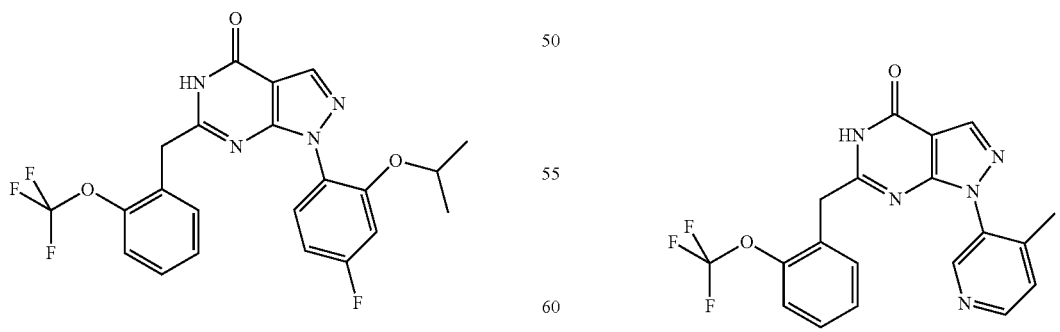

Example 10A was synthesized in analogy to example 3 using example 8V as starting material.
LC-MS (Method 1): RT=1.68 min
MS (ESI pos): m/z=463 (M+H)+

Exemplary Embodiments

Example 1

0.080 g (0.37 mmol) of 5-amino-1-(4-methyl-pyridin-3-yl)-1H-pyrazole-4-carboxylic acid amide (compare WO 04-099211) were dissolved in 1.5 ml of absolute ethanol and 0.31 g (1.3 mmol) of example 1B and 0.059 g (1.5 mmol) of sodium hydride (60% suspension in mineral oil) were added.

The reaction mixture was heated to reflux overnight. Cooling to room temperature was followed by evaporation of the solvent under reduced pressure. The remaining residue was treated with water (25 ml) and extracted three times with ethyl acetate. The organic layer was dried over sodium sulphate, filtered and the filtrate was concentrated under reduced pressure. The remaining residue was purified by preparative HPLC (eluent A: water, eluent B: acetonitrile). 106 mg (72% of theory) of the product were obtained.

TLC (CH$_2$Cl$_2$/MeOH; 10:1): R$_f$=0.44.

Example 2

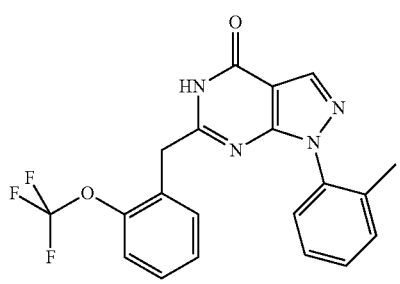 [SMILES: Cc1ccccc1-n1ncc2c(=O)[nH]c(Cc3ccccc3OC(F)(F)F)nc21]

In analogy to the preparation of example 1, 0.21 g (56% of theory) of the desired product were obtained from 0.20 g (0.92 mmol) of 5-amino-1-o-tolyl-1H-pyrazole-4-carboxylic acid amide (compare WO 04-099211) in 4.0 ml of absolute ethanol, 0.77 g (3.2 mmol) of example 1B, and 0.015 g (3.7 mmol) of sodium hydride (60% suspension in mineral oil).

TLC (CH$_2$Cl$_2$/MeOH; 10:1): R$_f$=0.6.

Example 3

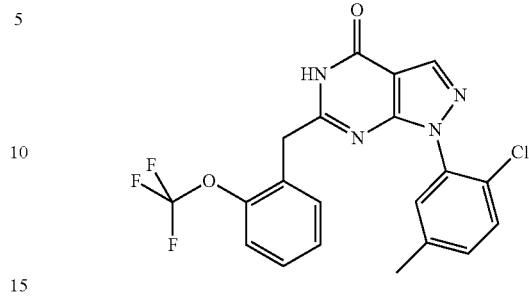

0.150 g (0.60 mmol) of example 8A were dissolved in 4.0 ml of absolute ethanol, 297 mg (1.20 mmol) of example 1A, and 71.8 mg (1.80 mmol) of sodium hydride (60% suspension in mineral oil) were added. The reaction mixture was heated to 150° C. for 30 min in a microwave oven. Cooling to room temperature was followed by evaporation of the solvent under reduced pressure. The remaining residue was treated with water (10 ml) and extracted three times with ethyl acetate. The organic layer was dried over sodium sulphate, filtered and the filtrate was concentrated under reduced pressure. The remaining residue was purified by preparative HPLC (eluent A: water+0.13% TFA, eluent B: acetonitrile). 131 mg (50% of theory) of the product were obtained as a colourless solid.

LC-MS (Method 1): RT=1.64 min
MS (ESI pos): m/z=435/437 (Cl) (M+H)$^+$.

The following examples were synthesized in analogy to the preparation of example 3, using the corresponding 5-amino-1H-pyrazole-4-carboxylic acid amides as starting materials:

| | structure | starting material | RT [min] | MS (ESI pos/neg, m/z) |
|---|---|---|---|---|
| Example 4 | 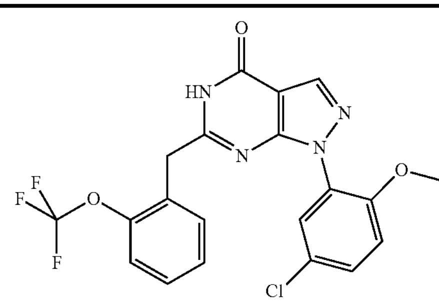 | Example 8B | 1.62 (Method 1) | 451/453 (Cl) (M + H)$^+$ |
| Example 5 | 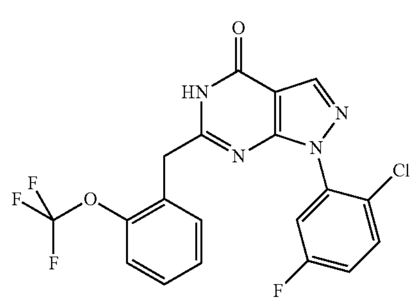 | Example 8C | 1.60 (Method 1) | 439/441 (Cl) (M + H)$^+$ |

| | structure | starting material | RT [min] | MS (ESI pos/neg, m/z) |
|---|---|---|---|---|
| Example 6 | 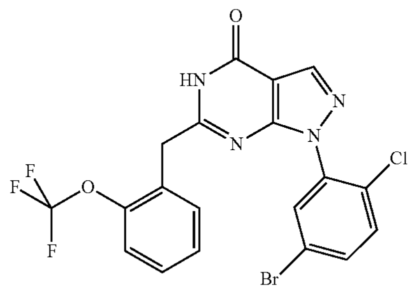 | Example 8D | 1.72 (Method 1) | 499/501/503 (Br, Cl) (M + H)+ |
| Example 7 | 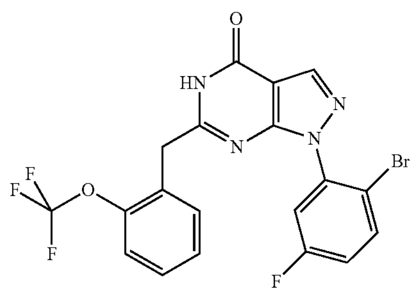 [SMILES: O=c1[nH]c(Cc2ccccc2OC(F)(F)F)nc2c1cnn2-c1cc(F)ccc1Br] | Example 8E | 1.61 (Method 1) | 483/485 (Br) (M + H)+ |
| Example 8 | 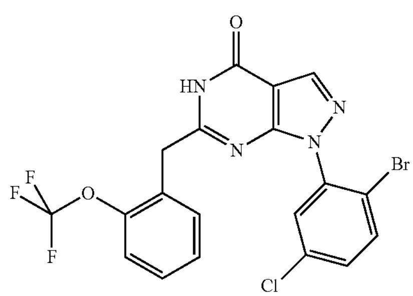 [SMILES: O=c1[nH]c(Cc2ccccc2OC(F)(F)F)nc2c1cnn2-c1cc(Cl)ccc1Br] | Example 8F | 1.68 (Method 1) | 499/501/503 (Br, Cl) (M + H)+ |
| Example 9 | 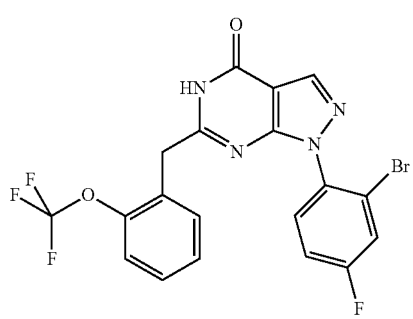 [SMILES: O=c1[nH]c(Cc2ccccc2OC(F)(F)F)nc2c1cnn2-c1ccc(F)cc1Br] | Example 8G | 1.68 (Method 1) | 483/485 (Br) (M + H)+ |
| Example 10 | 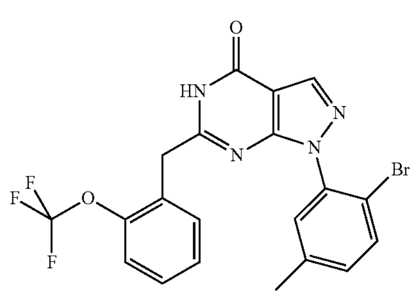 [SMILES: Cc1ccc(Br)c(-n2ncc3c(=O)[nH]c(Cc4ccccc4OC(F)(F)F)nc32)c1] | Example 8H | 1.65 (Method 1) | 479/481 (Br) (M + H)+ |

| | structure | starting material | RT [min] | MS (ESI pos/neg, m/z) |
|---|---|---|---|---|
| Example 11 | 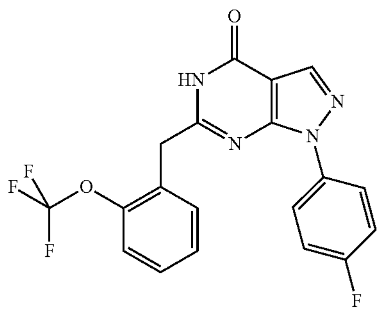 [SMILES: O=c1[nH]c(Cc2ccccc2OC(F)(F)F)nc2c1cnn2-c1ccc(F)cc1] | Example 8I | 1.66 (Method 1) | 405 (M + H)+ |
| Example 12 | 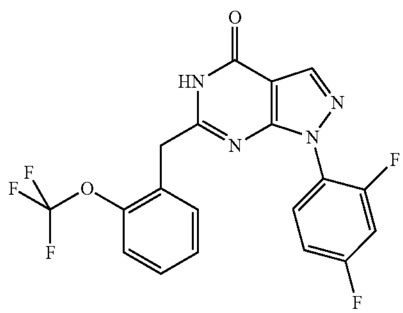 [SMILES: O=c1[nH]c(Cc2ccccc2OC(F)(F)F)nc2c1cnn2-c1ccc(F)cc1F] | Example 8J | 1.48 (Method 2) | 423 (M + H)+ |
| Example 13 | 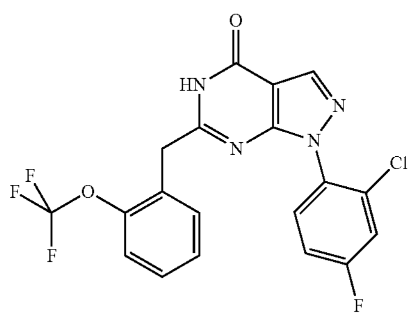 | Example 8K | 1.62 (Method 1) | 439/441 (Cl) (M + H)+ |
| Example 14 | 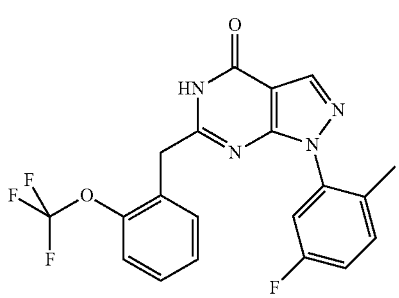 | Example 8L | 1.64 (Method 1) | 419 (M + H)+ |
| Example 15 | 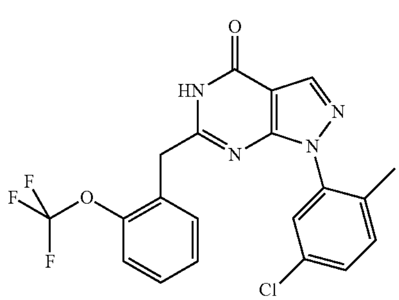 | Example 8M | 1.72 (Method 1) | 435/437 (Cl) (M + H)+ |

| | structure | starting material | RT [min] | MS (ESI pos/neg, m/z) |
|---|---|---|---|---|
| Example 16 | 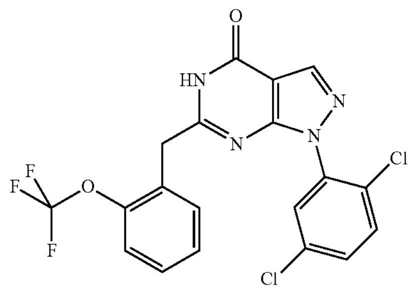 | Example 8N | 1.49 (Method 1) | 455/457/459 (2Cl) (M + H)+ |
| Example 17 | 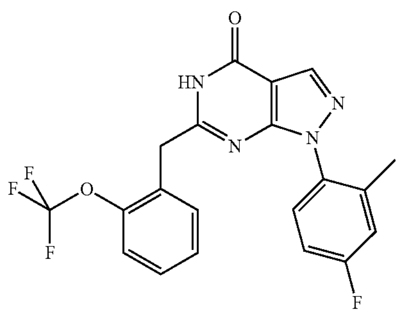 [SMILES: Cc1cc(F)ccc1-n1ncc2c(=O)[nH]c(Cc3ccccc3OC(F)(F)F)nc21] | Example 8O | 1.61 (Method 1) | 419 (M + H)+ |
| Example 18 | 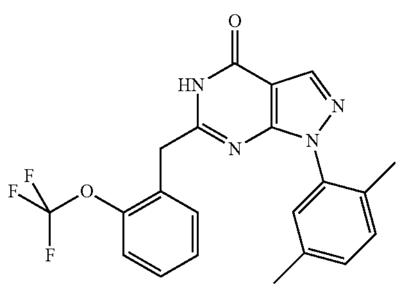 [SMILES: Cc1ccc(C)c(-n2ncc3c(=O)[nH]c(Cc4ccccc4OC(F)(F)F)nc32)c1] | Example 8P | 1.68 (Method 1) | 415 (M + H)+ |
| Example 19 | 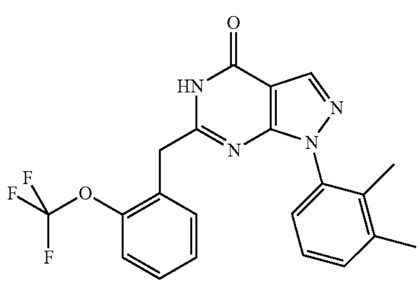 [SMILES: Cc1cccc(-n2ncc3c(=O)[nH]c(Cc4ccccc4OC(F)(F)F)nc32)c1C] | Example 8Q | 1.65 (Method 1) | 415 (M + H)+ |
| Example 20 | 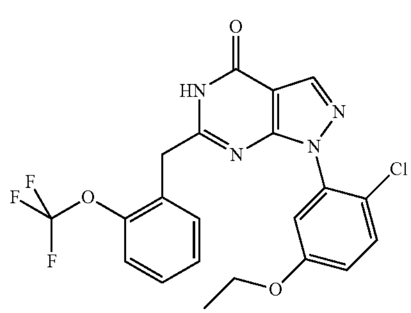 [SMILES: CCOc1ccc(Cl)c(-n2ncc3c(=O)[nH]c(Cc4ccccc4OC(F)(F)F)nc32)c1] | Example 8R | 1.68 (Method 1) | 465/467 (Cl) (M + H)+ |

-continued

| | structure | starting material | RT [min] | MS (ESI pos/neg, m/z) |
|---|---|---|---|---|
| Example 21 | 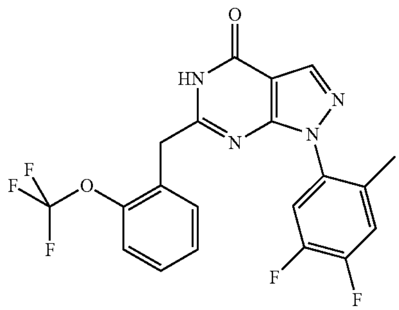 [SMILES: Cc1cc(F)c(F)cc1-n1ncc2c(=O)[nH]c(Cc3ccccc3OC(F)(F)F)nc21] | Example 8S | 1.67 (Method 1) | 437 (M + H)⁺ |
| Example 22 | 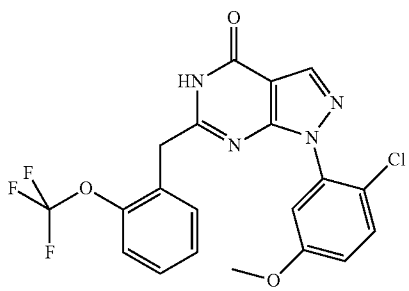 [SMILES: COc1ccc(Cl)c(-n2ncc3c(=O)[nH]c(Cc4ccccc4OC(F)(F)F)nc32)c1] | Example 8T | 1.59 (Method 1) | 451/453 (Cl) (M + H)⁺ |
| Example 23 | 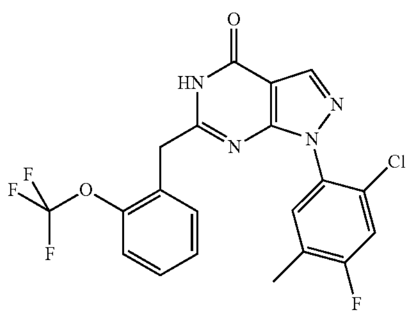 [SMILES: Cc1cc(-n2ncc3c(=O)[nH]c(Cc4ccccc4OC(F)(F)F)nc32)c(Cl)cc1F] | Example 8U | 1.70 (Method 1) | 453/455 (Cl) (M + H)⁺ |
| Example 24 | 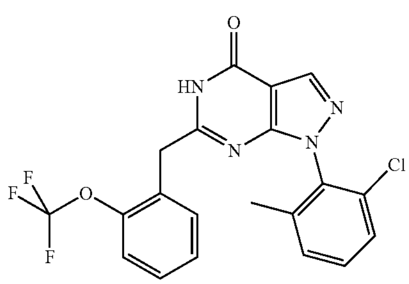 | Example 8W | 1.63 (Method 1) | 435/437 (Cl) (M + H)⁺ |
| Example 25 | 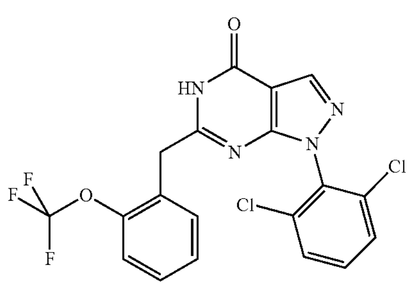 | Example 8X | 1.61 (Method 1) | 455/457/459 (2Cl) (M + H)⁺ |

-continued
| | structure | starting material | RT [min] | MS (ESI pos/neg, m/z) |
|---|---|---|---|---|
| Example 26 | 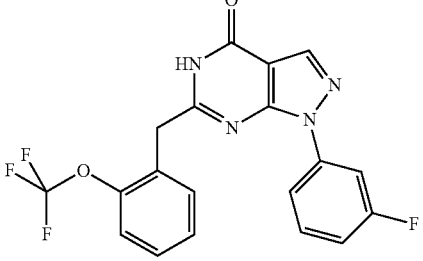 | Example 8Y | 1.70 (Method 1) | 405 (M + H)+ |
| Example 27 | 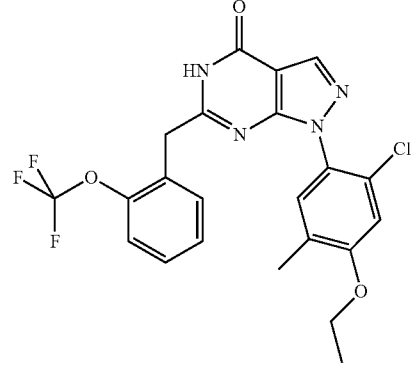 [SMILES: CCOc1cc(Cl)c(-n2ncc3c(=O)[nH]c(Cc4ccccc4OC(F)(F)F)nc32)cc1C] | Example 8Z | 1.77 (Method 1) | 479/481 (Cl) (M + H)+ |
| Example 28 | 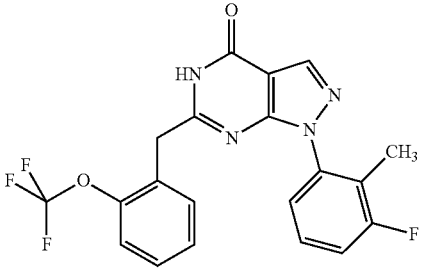 [SMILES: Cc1c(F)cccc1-n1ncc2c(=O)[nH]c(Cc3ccccc3OC(F)(F)F)nc21] | Example 8AA | 1.70 (Method 1) | 419 (Cl) (M + H)+ |
| Example 29 | 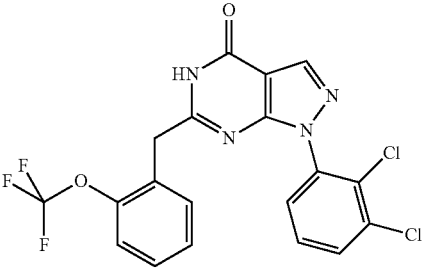 [SMILES: O=c1[nH]c(Cc2ccccc2OC(F)(F)F)nc2c1cnn2-c1cccc(Cl)c1Cl] | Example 8AB | 1.60 (Method 1) | 453/456 (2Cl) (M − H)+ |
| Example 30 | 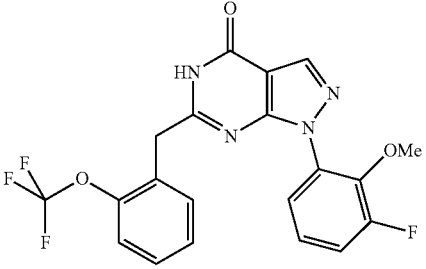 | Example 8AC | 1.57 (Method 1) | 435 (M + H)+ |

-continued
| structure | starting material | RT [min] | MS (ESI pos/neg, m/z) |
|---|---|---|---|
| Example 30-1 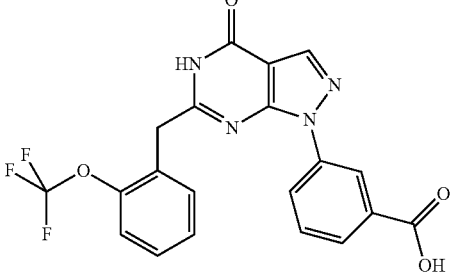 | Example 8 AG | 1.39 (Method 1) | 431 (M)+ |
| Example 30-2 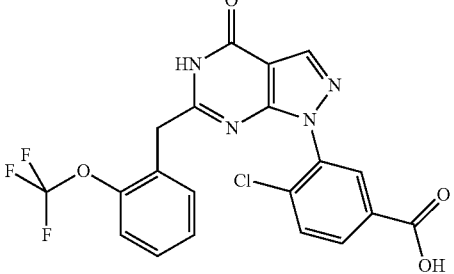 | Example 8 AF | 1.39 (Method 1) | 463/465 (Cl) (M −H)− |
| Example 30-3 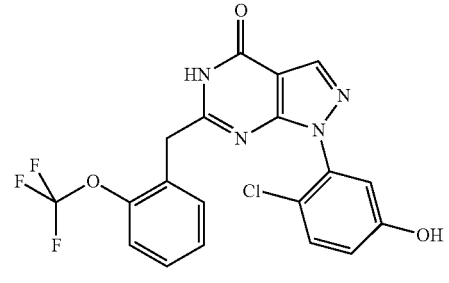 [SMILES: O=c1[nH]c(Cc2ccccc2OC(F)(F)F)nc2c1cnn2-c1cc(O)ccc1Cl] | Example 8 AH | 1.41 (Method 1) | 435/437 (Cl) (M − H)− |
| Example 30-4 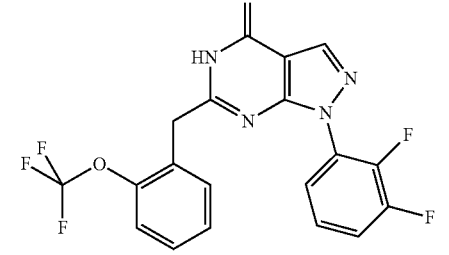 | | 1.53 (Method 1) | 423 (M + H)+ |

Example 30-5

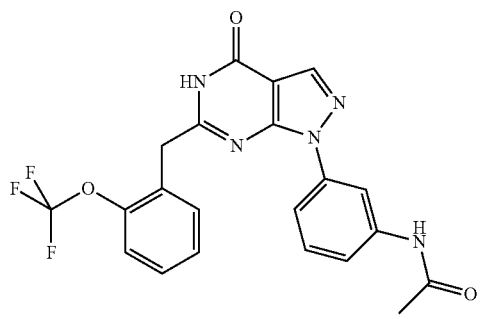 [SMILES: CC(=O)Nc1cccc(-n2ncc3c(=O)[nH]c(Cc4ccccc4OC(F)(F)F)nc32)c1]

a)

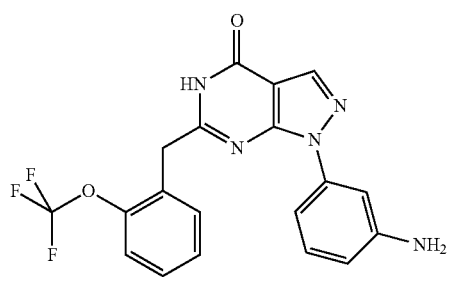 [SMILES: Nc1cccc(-n2ncc3c(=O)[nH]c(Cc4ccccc4OC(F)(F)F)nc32)c1]

The precursor to example 30-5 was synthesized in analogy to the preparation of example 3, using example 8AI as starting material.

LC-MS (Method 1): RT=1.23 min
MS (ESI pos): m/z=402 (M+H)+.

b)

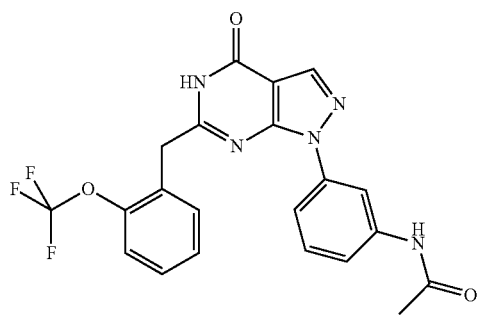 [SMILES: CC(=O)Nc1cccc(-n2ncc3c(=O)[nH]c(Cc4ccccc4OC(F)(F)F)nc32)c1]

0.10 g (0.20 mmol) of a) were dissolved in 5.0 ml of dichloromethane and 55.5 µL (0.40 mmol) triethylamine were added. The mixture was stirred at room temperature for 5 min followed by the addition of 29.9 µL (0.40 mmol) acetylchloride and further stirring at room temperature for 12 h. The reaction mixture was evaporated to dryness. Water was added and the resulting precipitate was filtered off and dried to afford 76.1 mg (86%) of example 30-4.

LC-MS (Method 1): RT=1.36 min
MS (ESI pos): m/z=444 (M+H)+.

Example 31

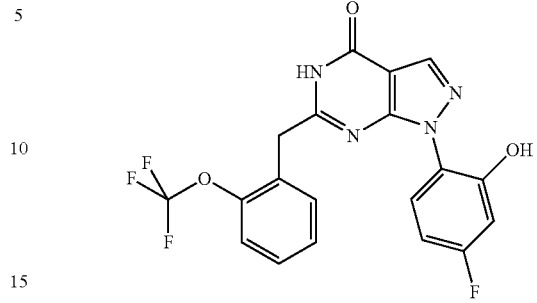

0.02 g (0.043 mmol) of example 10A were dissolved in 1.0 ml of BBr$_3$ and stirred at room temperature for 2 h. Water was added and the resulting slurry extracted with dichloromethane. The organic phase was separated, dried and evaporated to dryness to yield 18.2 mg (54% of theory) of the product as a colourless solid.

LC-MS (Method 1): RT=1.55 min
MS (ESI pos): m/z=421 (M+H)$^+$

Example 32

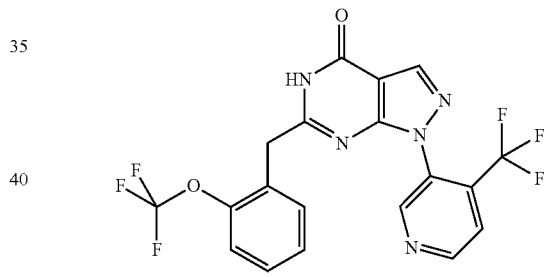

Example 9C (0.15 g; 0.65 mmol) was suspended in a 50 ml flask with polyphosphoric acid (1 g) and 2-(trifluoromethoxy)phenylacetic acid (428 mg; 1.94 mmol). The mixture, under mechanic stirring, was heated at 120° C. during 24 hours and the temperature was then lowered at room temperature, water was added (10 ml) and pH value was adjusted to 7 by addition of NH$_4$OH (30% solution). The aqueous phase was extracted with CH$_2$Cl$_2$ (2×20 ml) and the organic phase was dried over sodium sulphate. The crude product was purified by flash chromatography. Eluent: hexane/ethyl acetate 30/70.

Obtained 40 mg (0.09 mmol; yield=34%) of the desired compound

LC-MS (Method 1E): RT=8.35 min MS (APCI): m/z=456 (M+H)

The following examples were synthesized in analogy to the preparation of example 32, using the corresponding 5-amino-1H-pyrazole-4-carboxylic acid amides as starting materials:

| | structure | starting material | RT [min] | MS (APCI, m/z) |
|---|---|---|---|---|
| Example 33 | 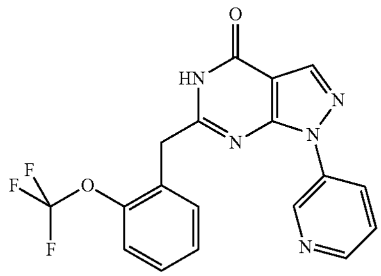 [SMILES: O=c1[nH]c(Cc2ccccc2OC(F)(F)F)nc2c1cnn2-c1cccnc1] | Example 9B | 7.35 (Method 1E) | 388 (M + H)+ |
| Example 34 | 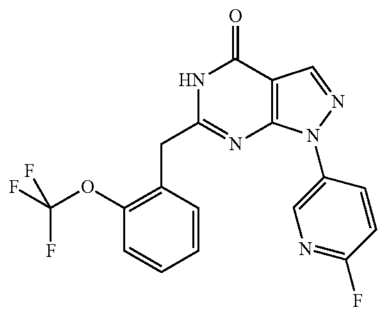 [SMILES: O=c1[nH]c(Cc2ccccc2OC(F)(F)F)nc2c1cnn2-c1ccc(F)nc1] | Example 9A | 6.93 (Method 1D) | 406 (M + H)+ |
| Example 39 | 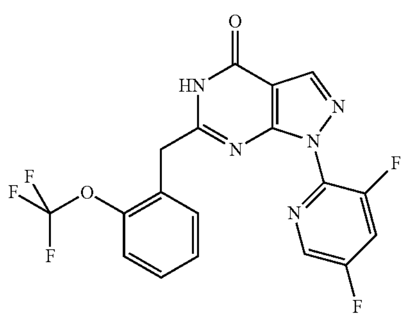 [SMILES: O=c1[nH]c(Cc2ccccc2OC(F)(F)F)nc2c1cnn2-c1ncc(F)cc1F] | Example 9D | 11, 59 (Method 2F) | 424 (M + H)+ |

Example 35

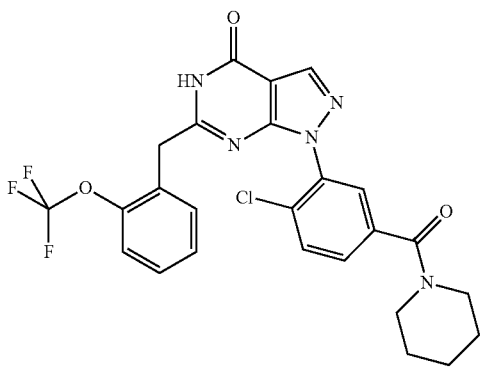 [SMILES: O=C(c1ccc(Cl)c(-n2ncc3c(=O)[nH]c(Cc4ccccc4OC(F)(F)F)nc32)c1)N1CCCCC1]

0.05 g (0.11 mmol) of example 30-2, 11.0 µL piperidine (0.11 mmol), 40.0 mg TBTU (0.13 mmol) and 40.0 µL DIPEA (0.23 mmol) were dissolved in 5 mL dichloromethane and stirred at room temperature over night. Standard aqueous work up and HPLC-separation (eluent A: water+0.13% TFA, eluent B: acetonitrile) afforded 35 mg (61%) of example 35.

LC-MS (Method 1): RT=1.54 min

MS (ESI pos): m/z=532/534 (Cl) (M+H)+

The following examples were synthesized in analogy to the preparation of example 35, using the corresponding amines:

| | structure | starting material | RT [min] | MS (ESI pos, m/z) |
|---|---|---|---|---|
| Example 36 | 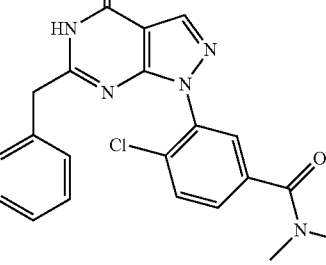 | Example 30-2 | 1.38 (Method 1) | 492/494 (Cl) (M + H)+ |
| Example 37 | 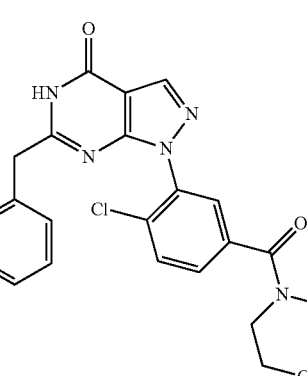 | Example 30-2 | 1.37 (Method 1) | 534/536 (Cl) (M + H)+ |
| Example 38 | 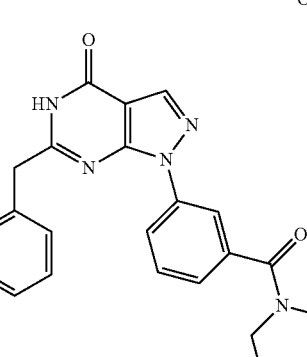 | Example 30-1 | 1.37 (Method 1) | 500 (M + H)+ |

The invention claimed is:

1. A compound of formula I:

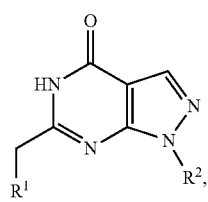

(I)

with

R[1] being phenyl or pyridyl, any of which is substituted with 1 to 4 substituents X;

and with the option that each of phenyl or pyridyl in addition may be substituted by up to 3 radicals independently of one another selected from the group of $C_1$-$C_6$-alkyl, $C_1$-$C_6$-alkoxy, hydroxycarbonyl, cyano, trifluoromethyl, amino, nitro, hydroxy, $C_1$-$C_6$-alkylamino, halogen, $C_6$-$C_{10}$-arylcarbonylamino, $C_1$-$C_6$-alkylcarbonylamino, $C_1$-$C_6$-alkylaminocarbonyl, $C_1$-$C_6$-alkoxycarbonyl, $C_6$-$C_{10}$-arylaminocarbonyl, heteroarylamino-carbonyl, heteroarylcarbonylamino, $C_1$-$C_6$-alkylsulphonylamino, $C_1$-$C_6$-alkylsulphonyl, or $C_1$-$C_6$-alkylthio, where each of $C_1$-$C_6$-alkyl, $C_1$-$C_6$-alkoxy, $C_1$-$C_6$-alkylamino, $C_6$-$C_{10}$-arylcarbonylamino, $C_1$-$C_6$-alkylcarbonylamino, $C_1$-$C_6$-alkylaminocarbonyl, $C_1$-$C_6$-alkoxycarbonyl, $C_6$-$C_{10}$-arylaminocarbonyl, heteroarylaminocarbonyl, heteroarylcarbonylamino, $C_1$-$C_6$-alkylsulphonylamino, $C_1$-$C_6$-alkylsulphonyl and $C_1$-$C_6$-alkylthio are optionally substituted by 1 to 3 radicals independently of one another selected from the group of hydroxy, cyano, halogen, hydroxycarbonyl and a group of the formula —$NR^3R^4$, X
independently of each other being selected from $C_1$-$C_6$-alkoxy, where the $C_1$-$C_6$-alkoxy is substituted with 2 to 6 halogen substituents, and the halogen substituents are selected from the group of fluoro, chloro and bromo, whereby the C-atom directly attached to the O-atom, which constitutes the beta position with respect to the link to the phenyl or pyridyl, is substituted with at least one halogen atom;

$R^2$
being phenyl or heteroaryl, where phenyl is substituted by 1 to 3 radicals and heteroaryl is optionally substituted by 1 to 3 radicals in each case independently of one another selected from the group of $C_1$-$C_6$-alkyl, $C_1$-$C_6$-alkoxy, hydroxycarbonyl, cyano, trifluoromethyl, amino, nitro, hydroxy, $C_1$-$C_6$-alkylamino, halogen, $C_6$-$C_{10}$-arylcarbonylamino, $C_1$-$C_6$-alkylcarbonylamino, $C_1$-$C_6$-alkylaminocarbonyl, $C_1$-$C_6$-alkoxycarbonyl, $C_6$-$C_{10}$-arylaminocarbonyl, heteroarylaminocarbonyl, heteroarylcarbonylamino, $C_1$-$C_6$-alkylsulphonylamino, $C_1$-$C_6$-alkylsulphonyl and $C_1$-$C_6$-alkylthio, where each of $C_1$-$C_6$-alkyl, $C_1$-$C_6$-alkoxy, $C_1$-$C_6$-alkylamino, $C_6$-$C_{10}$-arylcarbonylamino, $C_1$-$C_6$-alkylcarbonylamino, $C_1$-$C_6$-alkylaminocarbonyl, $C_1$-$C_6$-alkoxycarbonyl, $C_6$-$C_{10}$-arylaminocarbonyl, heteroarylaminocarbonyl, heteroarylcarbonylamino, $C_1$-$C_6$-alkylsulphonylamino, $C_1$-$C_6$-alkylsulphonyl and $C_1$-$C_6$-alkylthio are optionally substituted by one to three radicals independently of one another selected from the group of hydroxy, cyano, halogen, hydroxycarbonyl and a group of the formula —$NR^3R^4$, $R^3$
being hydrogen or $C_1$-$C_6$-alkyl,
and $R^4$
being hydrogen or $C_1$-$C_6$-alkyl,
or $R^3$ and $R^4$ together with the nitrogen atom to which they are bonded are 5- to 8-membered heterocyclyl.

2. A compound according to claim 1, characterized in that $R^1$
being phenyl or pyridyl, any of which is substituted with 1 to 3 substituents X;
and with the option that each of phenyl or pyridyl in addition may be substituted by up to 3 radicals independently of one another selected from the group of $C_1$-$C_6$-alkyl, $C_1$-$C_6$-alkoxy, cyano, trifluoromethyl, nitro, halogen, $C_6$-$C_{10}$-arylcarbonylamino, $C_1$-$C_6$-alkyl-carbonylamino, $C_1$-$C_6$-alkylaminocarbonyl, $C_6$-$C_{10}$-arylaminocarbonyl, heteroarylamino-carbonyl, heteroarylcarbonylamino, $C_1$-$C_6$-alkylsulphonylamino, $C_1$-$C_6$-alkylsulphonyl, or $C_1$-$C_6$-alkylthio, where each of $C_1$-$C_6$-alkyl, $C_1$-$C_6$-alkoxy, $C_6$-$C_{10}$-arylcarbonylamino, $C_1$-$C_6$-alkyl-carbonylamino, $C_1$-$C_6$-alkylaminocarbonyl, $C_6$-$C_{10}$-arylaminocarbonyl, heteroarylamino-carbonyl, heteroarylcarbonylamino, $C_1$-$C_6$-alkylsulphonylamino, $C_1$-$C_6$-alkylsulphonyl and $C_1$-$C_6$-alkylthio are optionally substituted by one to three radicals independently of one another selected from the group of hydroxy, cyano, halogen, and a group of the formula —$NR^3R^4$, $R^2$
being phenyl or heteroaryl, where phenyl is substituted by 1 to 3 radicals and heteroaryl is optionally substituted by 1 to 3 radicals in each case independently of one another selected from the group of $C_1$-$C_6$-alkyl, $C_1$-$C_6$-alkoxy, hydroxycarbonyl, cyano, trifluoromethyl, amino, nitro, hydroxy, $C_1$-$C_6$-alkylamino, halogen, $C_1$-$C_6$-alkyl-carbonylamino, $C_1$-$C_6$-alkylaminocarbonyl, $C_1$-$C_6$-alkylsulphonylamino, $C_1$-$C_6$-alkyl-sulphonyl and $C_1$-$C_6$-alkylthio, where each of $C_1$-$C_6$-alkyl, $C_1$-$C_6$-alkoxy, $C_1$-$C_6$-alkylamino, $C_1$-$C_6$-alkylcarbonylamino, $C_1$-$C_6$-alkylaminocarbonyl, $C_1$-$C_6$-alkylsulphonylamino, $C_1$-$C_6$-alkylsulphonyl and $C_1$-$C_6$-alkylthio are optionally substituted by one to three radicals independently of one another selected from the group of hydroxy, cyano, halogen, and a group of the formula —$NR^3R^4$, and the remaining characteristics as defined in claim 1.

3. A compound according to claim 1, characterized in that $R^1$
being phenyl or pyridyl, any of which is substituted with one to three substituents X;
and with the option that each of phenyl or pyridyl in addition may be substituted by up to 3 radicals independently of one another selected from the group of $C_1$-$C_6$-alkyl, trifluoromethyl, or halogen, $R^2$
being phenyl or pyridyl, where phenyl is substituted by 1 to 3 radicals and heteroaryl is optionally substituted by 1 to 3 radicals in each case independently of one another selected from the group of $C_1$-$C_6$-alkyl, $C_1$-$C_6$-alkoxy, trifluoromethyl, halogen and $C_1$-$C_6$-alkylthio, where each of $C_1$-$C_6$-alkyl, $C_1$-$C_6$-alkoxy and $C_1$-$C_6$-alkylthio, are optionally substituted by one to three halogen radicals, and the remaining characteristics as defined in claim 1.

4. A compound according to claim 1, characterized in that $R^1$
is phenyl or pyridyl, any of which is substituted with 1 to 3 X, and wherein X is $C_1$-$C_6$-alkoxy, substituted by 2 to 6 halogen atoms, selected from the group of fluoro, chloro and bromo, whereby the C-atom which constitutes the beta position with respect to the link to the phenyl or pyridyl is substituted with at least one halogen;
and with the option that each of phenyl or pyridyl in addition may be substituted by up to 3 radicals independently of one another selected from the group of $C_1$-$C_6$-alkyl, trifluoromethyl, halogen, and the remaining characteristics as defined in claim 1.

5. A compound according to claim 1, characterized in that for $R^1$ the substitution pattern at the one to 3 mandatory substituents X are at least 2 fluoro substituents, whereby the C-atom which constitutes the beta position with respect to the link to the phenyl or pyridyl is substituted with at least one halogen.

6. A compound according to claim 1, characterized in that $R^1$ is 2-trifluoromethoxyphenyl.

7. A compound selected from the group consisting of

| Compound No. | Structure |
|---|---|
| 1 | *pyrazolo[3,4-d]pyrimidin-4(5H)-one with 2-(trifluoromethoxy)benzyl and 4-methylpyridin-3-yl substituents* |
| 2 | *pyrazolo[3,4-d]pyrimidin-4(5H)-one with 2-(trifluoromethoxy)benzyl and o-tolyl substituents* |
| 3 | *pyrazolo[3,4-d]pyrimidin-4(5H)-one with 2-(trifluoromethoxy)benzyl and 2-chloro-5-methylphenyl substituents* |
| 4 | *pyrazolo[3,4-d]pyrimidin-4(5H)-one with 2-(trifluoromethoxy)benzyl and 5-chloro-2-methoxyphenyl substituents* |
| 5 | *pyrazolo[3,4-d]pyrimidin-4(5H)-one with 2-(trifluoromethoxy)benzyl and 2-chloro-5-fluorophenyl substituents* |
| 6 | *pyrazolo[3,4-d]pyrimidin-4(5H)-one with 2-(trifluoromethoxy)benzyl and 5-bromo-2-chlorophenyl substituents* |
| 7 | *pyrazolo[3,4-d]pyrimidin-4(5H)-one with 2-(trifluoromethoxy)benzyl and 2-bromo-5-fluorophenyl substituents* |
| 8 | *pyrazolo[3,4-d]pyrimidin-4(5H)-one with 2-(trifluoromethoxy)benzyl and 2-bromo-5-chlorophenyl substituents* |
| 9 | *pyrazolo[3,4-d]pyrimidin-4(5H)-one with 2-(trifluoromethoxy)benzyl and 2-bromo-4-fluorophenyl substituents* |
| 10 | *pyrazolo[3,4-d]pyrimidin-4(5H)-one with 2-(trifluoromethoxy)benzyl and 2-bromo-5-methylphenyl substituents* |

| Compound No. | Structure |
|---|---|
| 11 | 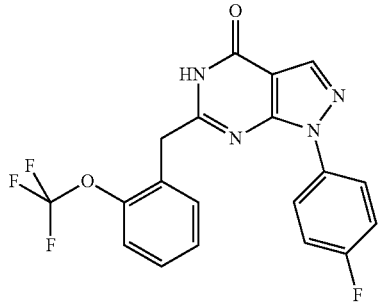 |
| 12 | 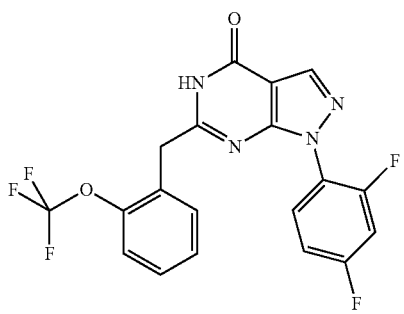 [SMILES: O=c1[nH]c(Cc2ccccc2OC(F)(F)F)nc2c1cnn2-c1ccc(F)cc1F] |
| 13 | 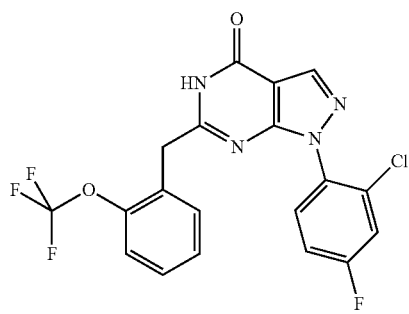 [SMILES: O=c1[nH]c(Cc2ccccc2OC(F)(F)F)nc2c1cnn2-c1ccc(F)cc1Cl] |
| 14 | 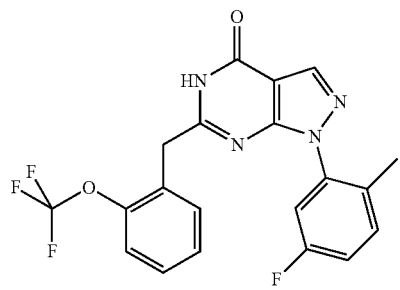 [SMILES: Cc1ccc(F)cc1-n1ncc2c(=O)[nH]c(Cc3ccccc3OC(F)(F)F)nc21] |
| 15 | 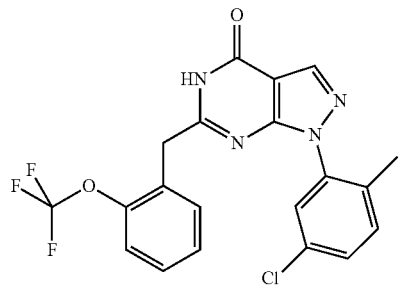 [SMILES: Cc1ccc(Cl)cc1-n1ncc2c(=O)[nH]c(Cc3ccccc3OC(F)(F)F)nc21] |
| Compound No. | Structure |
|---|---|
| 16 | 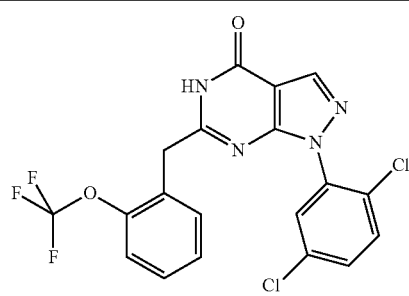 |
| 17 | 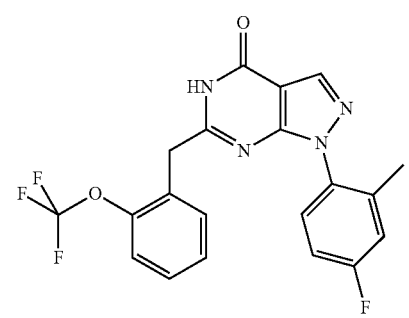 [SMILES: Cc1cc(F)ccc1-n1ncc2c(=O)[nH]c(Cc3ccccc3OC(F)(F)F)nc21] |
| 18 | 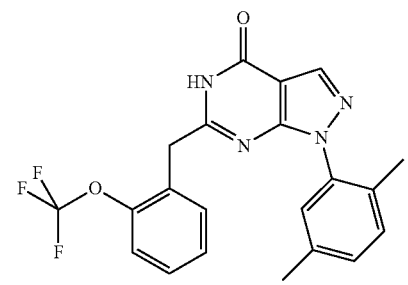 [SMILES: Cc1ccc(C)c(-n2ncc3c(=O)[nH]c(Cc4ccccc4OC(F)(F)F)nc32)c1] |
| 19 | 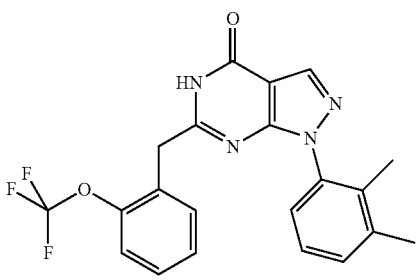 [SMILES: Cc1cccc(-n2ncc3c(=O)[nH]c(Cc4ccccc4OC(F)(F)F)nc32)c1C] |
| 20 | 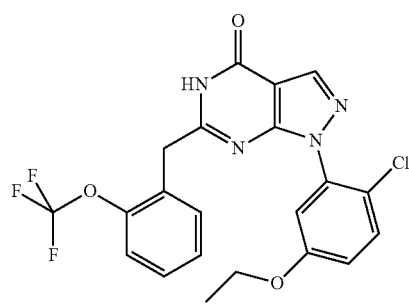 [SMILES: CCOc1ccc(Cl)c(-n2ncc3c(=O)[nH]c(Cc4ccccc4OC(F)(F)F)nc32)c1] |

| Compound No. | Structure |
|---|---|
| 21 | 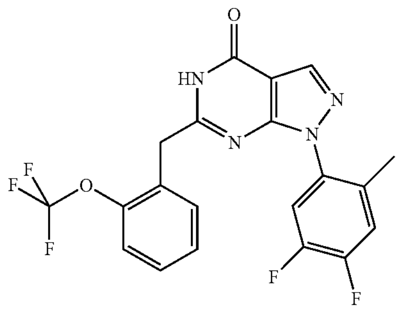 [SMILES: Cc1cc(F)c(F)cc1-n1ncc2c(=O)[nH]c(Cc3ccccc3OC(F)(F)F)nc21] |
| 22 | 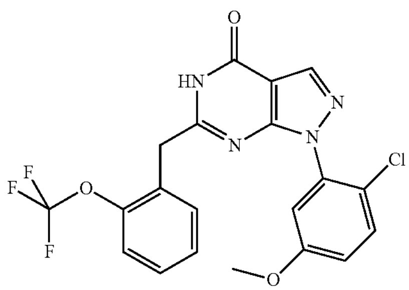 [SMILES: COc1ccc(Cl)c(-n2ncc3c(=O)[nH]c(Cc4ccccc4OC(F)(F)F)nc32)c1] |
| 23 | 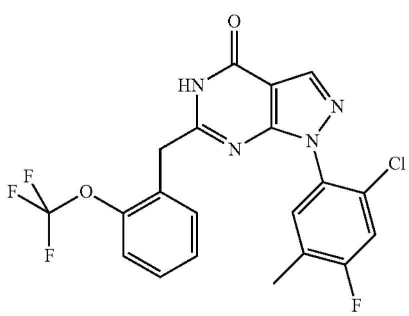 [SMILES: Cc1cc(-n2ncc3c(=O)[nH]c(Cc4ccccc4OC(F)(F)F)nc32)c(Cl)cc1F] |
| 24 | 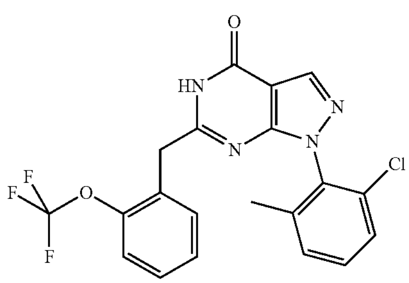 |
| 25 | 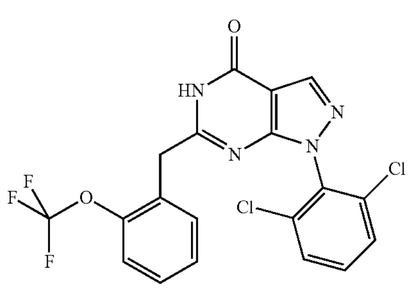 |

| Compound No. | Structure |
|---|---|
| 26 | 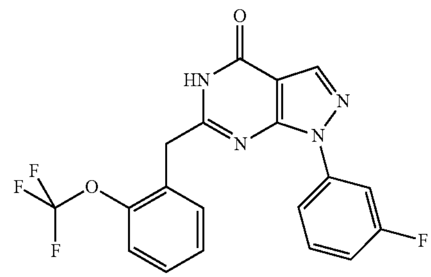 [SMILES: O=c1[nH]c(Cc2ccccc2OC(F)(F)F)nc2c1cnn2-c1cccc(F)c1] |
| 27 | 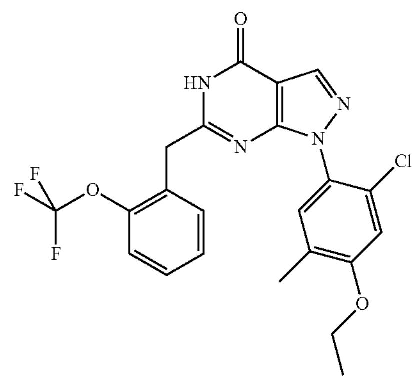 [SMILES: CCOc1cc(Cl)c(-n2ncc3c(=O)[nH]c(Cc4ccccc4OC(F)(F)F)nc32)cc1C] |
| 28 | 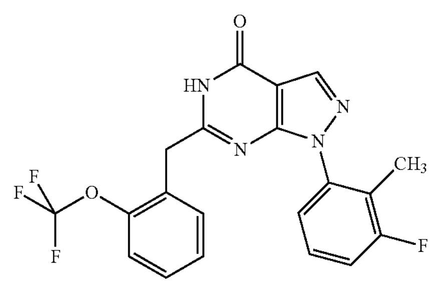 [SMILES: Cc1c(F)cccc1-n1ncc2c(=O)[nH]c(Cc3ccccc3OC(F)(F)F)nc21] |
| 29 | 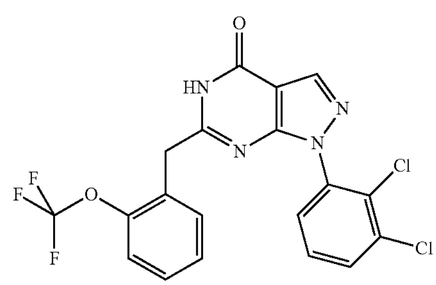 [SMILES: O=c1[nH]c(Cc2ccccc2OC(F)(F)F)nc2c1cnn2-c1cccc(Cl)c1Cl] |
| 30 | 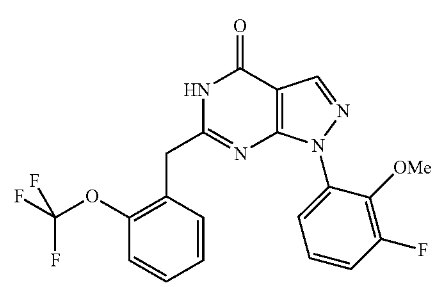 [SMILES: COc1c(F)cccc1-n1ncc2c(=O)[nH]c(Cc3ccccc3OC(F)(F)F)nc21] |

| Compound No. | Structure |
|---|---|
| 30-1 | 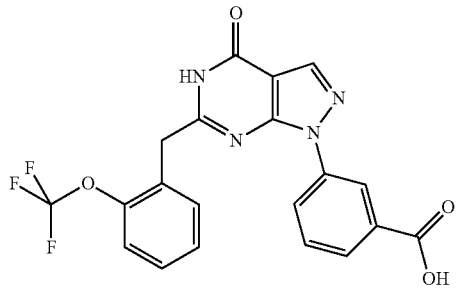 [SMILES: O=C(O)c1cccc(-n2ncc3c(=O)[nH]c(Cc4ccccc4OC(F)(F)F)nc32)c1] |
| 30-2 | 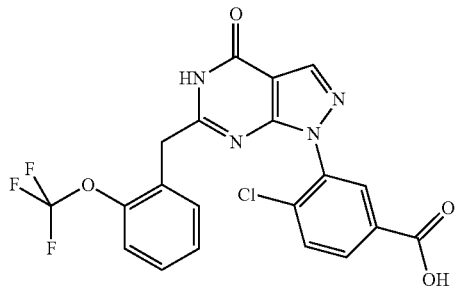 [SMILES: O=C(O)c1ccc(Cl)c(-n2ncc3c(=O)[nH]c(Cc4ccccc4OC(F)(F)F)nc32)c1] |
| 30-3 | 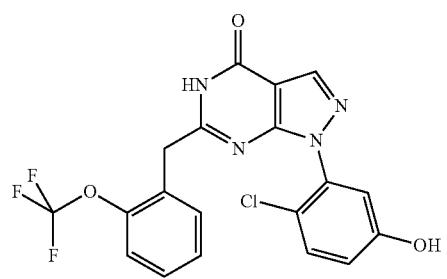 [SMILES: O=c1[nH]c(Cc2ccccc2OC(F)(F)F)nc2c1cnn2-c1cc(O)ccc1Cl] |
| 30-4 | 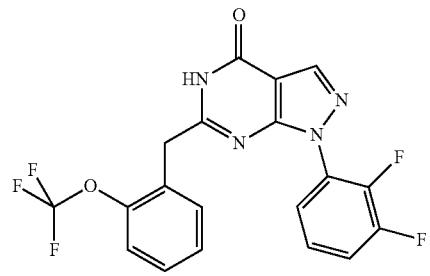 [SMILES: O=c1[nH]c(Cc2ccccc2OC(F)(F)F)nc2c1cnn2-c1cccc(F)c1F] |
| 30-5 | 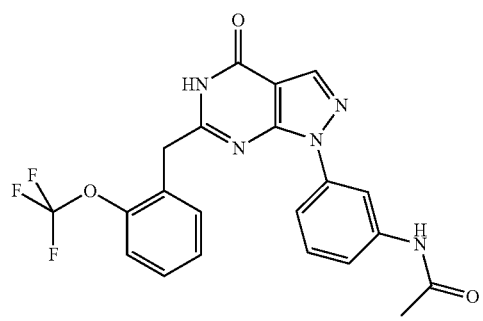 [SMILES: CC(=O)Nc1cccc(-n2ncc3c(=O)[nH]c(Cc4ccccc4OC(F)(F)F)nc32)c1] |
| Compound No. | Structure |
|---|---|
| 31 | 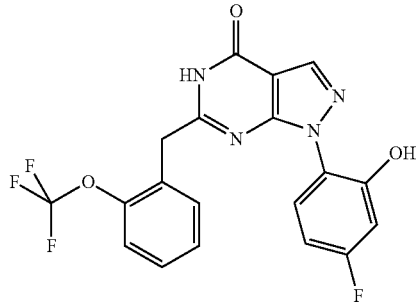 [SMILES: O=c1[nH]c(Cc2ccccc2OC(F)(F)F)nc2c1cnn2-c1ccc(F)cc1O] |
| 32 | 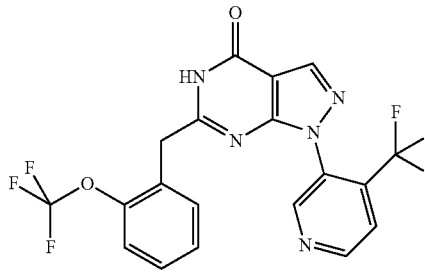 |
| 33 | 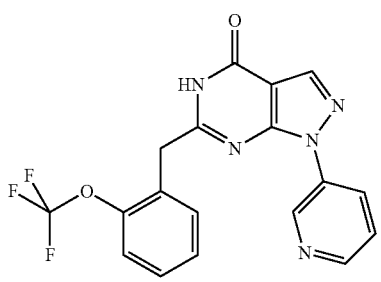 |
| 34 | 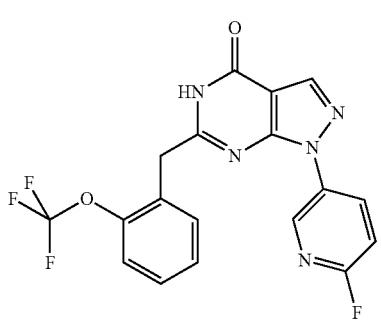 |

| Compound No. | Structure |
|---|---|
| 35 | 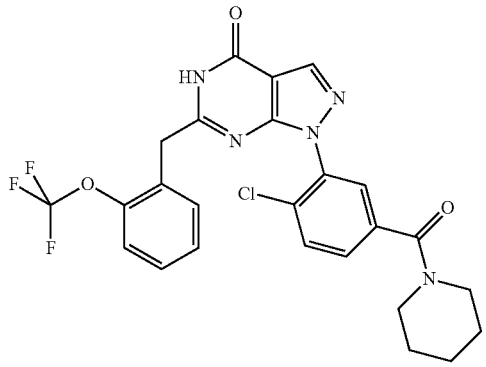 [SMILES: O=C(c1ccc(Cl)c(-n2ncc3c(=O)[nH]c(Cc4ccccc4OC(F)(F)F)nc32)c1)N1CCCCC1] |
| 36 | 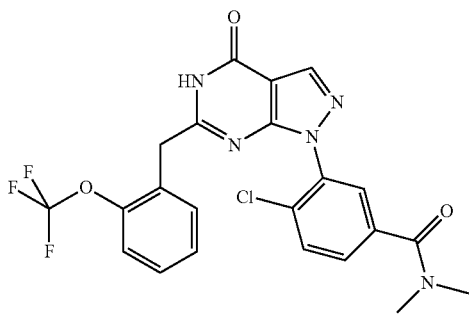 [SMILES: CN(C)C(=O)c1ccc(Cl)c(-n2ncc3c(=O)[nH]c(Cc4ccccc4OC(F)(F)F)nc32)c1] |
| 37 | 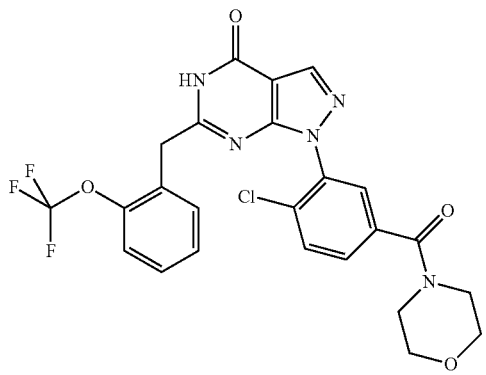 [SMILES: O=C(c1ccc(Cl)c(-n2ncc3c(=O)[nH]c(Cc4ccccc4OC(F)(F)F)nc32)c1)N1CCOCC1] |
| Compound No. | Structure |
|---|---|
| 38 | 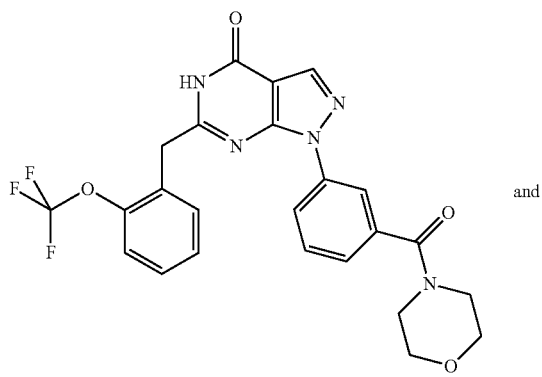 [SMILES: O=C(c1cccc(-n2ncc3c(=O)[nH]c(Cc4ccccc4OC(F)(F)F)nc32)c1)N1CCOCC1] and |
| 39 | 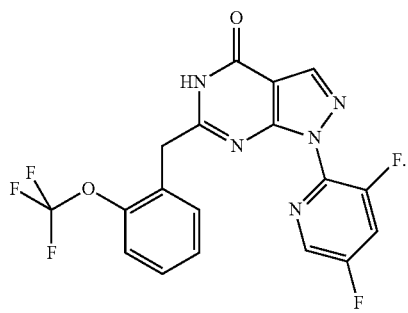 [SMILES: O=c1[nH]c(Cc2ccccc2OC(F)(F)F)nc2c1cnn2-c1ncc(F)cc1F] |
8. A pharmaceutically acceptable salt of a compound according to claim 1.
9. A pharmaceutical composition comprising a compound according to claim 1.
* * * * *

UNITED STATES PATENT AND TRADEMARK OFFICE
CERTIFICATE OF CORRECTION

| | |
|---|---|
| PATENT NO. | : 8,648,085 B2 |
| APPLICATION NO. | : 12/744750 |
| DATED | : February 11, 2014 |
| INVENTOR(S) | : Christian Eickmeier et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 657 days.

Signed and Sealed this
Twenty-first Day of April, 2015

Michelle K. Lee
*Director of the United States Patent and Trademark Office*